(12) United States Patent
Baker et al.

(10) Patent No.: US 11,298,435 B2
(45) Date of Patent: Apr. 12, 2022

(54) DEVICE AND METHOD FOR STERILIZING A CATHETER SYSTEM

(71) Applicant: Baker Group, LLP, Portland, OR (US)

(72) Inventors: Michael John Baker, Portland, OR (US); Sudeshna Dutta, Portland, OR (US); Christian Terry Proch McMechan, Victoria (CA); Nicholas David Allan, Victoria (CA); Nathan John Muller, Victoria (CA); Mark Sasha Drlik, Victoria (CA); Paul Yvon Charlebois, Victoria (CA)

(73) Assignee: Baker Group, LLP, Portland, OR (US)

( * ) Notice: Subject to any disclaimer, the term of this patent is extended or adjusted under 35 U.S.C. 154(b) by 22 days.

(21) Appl. No.: 16/358,152

(22) Filed: Mar. 19, 2019

(65) Prior Publication Data

US 2019/0290791 A1 Sep. 26, 2019

Related U.S. Application Data

(60) Provisional application No. 62/646,201, filed on Mar. 21, 2018.

(51) Int. Cl.
*A61L 2/10* (2006.01)
*A61M 39/16* (2006.01)
(Continued)

(52) U.S. Cl.
CPC ............ *A61L 2/10* (2013.01); *A61M 39/0208* (2013.01); *A61M 39/16* (2013.01);
(Continued)

(58) Field of Classification Search
CPC ...... A61L 2/10; A61L 2202/24; A61M 39/16; A61M 39/0208; A61M 39/20;
(Continued)

(56) References Cited

U.S. PATENT DOCUMENTS 9,056,147 B2 * 6/2015 Ma ...................... A61M 39/165
9,295,742 B2 * 3/2016 Rasooly .................... A61L 2/10
(Continued)

OTHER PUBLICATIONS

Maki, D. et al., "The Risk of Bloodstream Infection in Adults With Different Intravascular Devices: A Systematic Review of 200 Published Prospective Studies," Mayo Clinic Proceedings, vol. 81, No. 9, Sep. 2006, 13 pages.
(Continued)

*Primary Examiner* — Regina M Yoo
(74) *Attorney, Agent, or Firm* — McCoy Russell LLP

(57) ABSTRACT

Methods and systems for a catheter access port cleaning, disinfection or sterilization device are disclosed. The catheter access port cleaning, disinfection or sterilization device may comprise, a first housing having a power source and control circuit; a second housing shaped to mate with a catheter and having a first ultra-violet light source mounted therein, the first housing wired to the second housing to power the light source. When activated, the ultra-violet light source emits ultra-violet radiation that is transmitted from the second housing to the catheter attached to a patient. In this way, the device provides an efficient system for cleaning, disinfecting or sterilizing an access port in the second housing while reducing patient infections.

14 Claims, 31 Drawing Sheets

(51) Int. Cl.
*A61M 39/02* (2006.01)
*A61M 25/00* (2006.01)

(52) U.S. Cl.
CPC .. *A61L 2202/24* (2013.01); *A61M 2025/0019* (2013.01); *A61M 2039/167* (2013.01)

(58) Field of Classification Search
CPC .... A61M 2025/0019; A61M 2039/167; A61B 90/70; A61B 2090/701
See application file for complete search history.

(56) References Cited

U.S. PATENT DOCUMENTS

| | | | | |
|---|---|---|---|---|
| 10,610,609 | B2* | 4/2020 | Swaney | A61L 2/28 |
| 2008/0306454 | A1 | 12/2008 | Sikora | |
| 2013/0303996 | A1* | 11/2013 | Rasooly | A61L 2/10 |
| | | | | 604/264 |
| 2013/0323120 | A1* | 12/2013 | Ma | A61L 2/24 |
| | | | | 422/24 |
| 2015/0290347 | A1* | 10/2015 | Braden | A61L 2/10 |
| | | | | 422/24 |
| 2017/0028444 | A1* | 2/2017 | Rudser | H04N 5/23212 |
| 2017/0182305 | A1* | 6/2017 | Kermode | A61M 39/18 |
| 2019/0358387 | A1* | 11/2019 | Elbadry | A61M 1/3663 |
| 2020/0188543 | A1* | 6/2020 | Etter | A61B 50/22 |

OTHER PUBLICATIONS

"B Braun Medical—415119—Ultrasite Ag Antibacterial Luer Access Device, Needleless Connector," Stomabags Website, Available Online at https://www.stomabags.com/b-braun-medical-415119-ultrasite-ag-antibacterial-luer-access-device-needleless-connector, Website Available as Early as Nov. 6, 2010, 5 pages.

"Making Health Care Safer: Reducing bloodstream infections," CDC Website, Available Online at https://www.cdc.gov/vitalsigns/pdf/2011-03-vitalsigns.pdf, Mar. 2011, 4 pages.

"Preventing Central Line-Associated Bloodstream Infections: A Global Challenge, A Global Perspective," The Joint Commission Website, Available Online at https://www.jointcommission.org/assets/1/18/CLABSI_Monograph.pdf, May 2012, 152 pages.

"CSU100 Ultrasite Valve," Right Way Medical Website, Available Online at https://rightwaymed.com/product/csu100-ultrasite-valve/, Available as Early as Feb. 16, 2017, 2 pages.

* cited by examiner

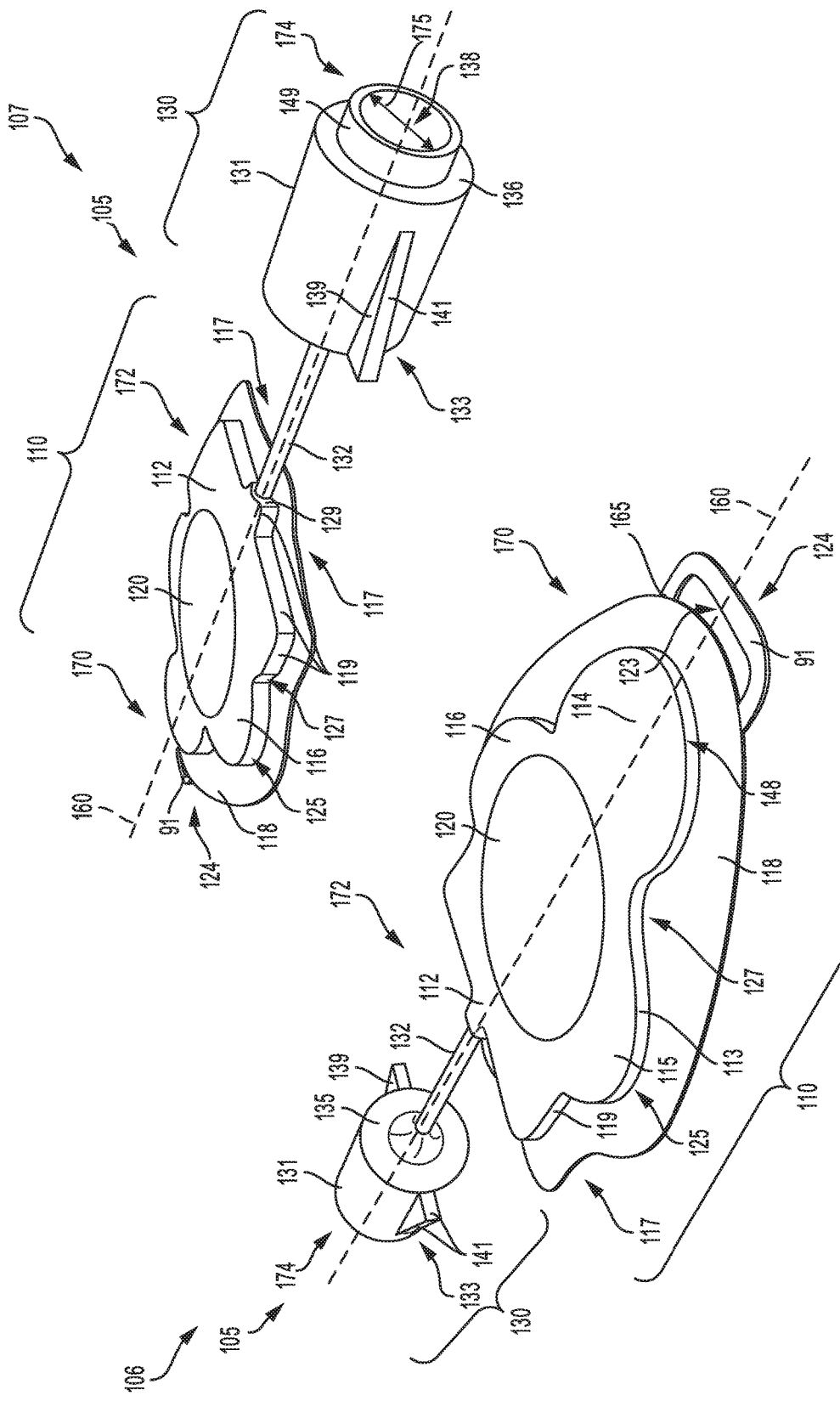

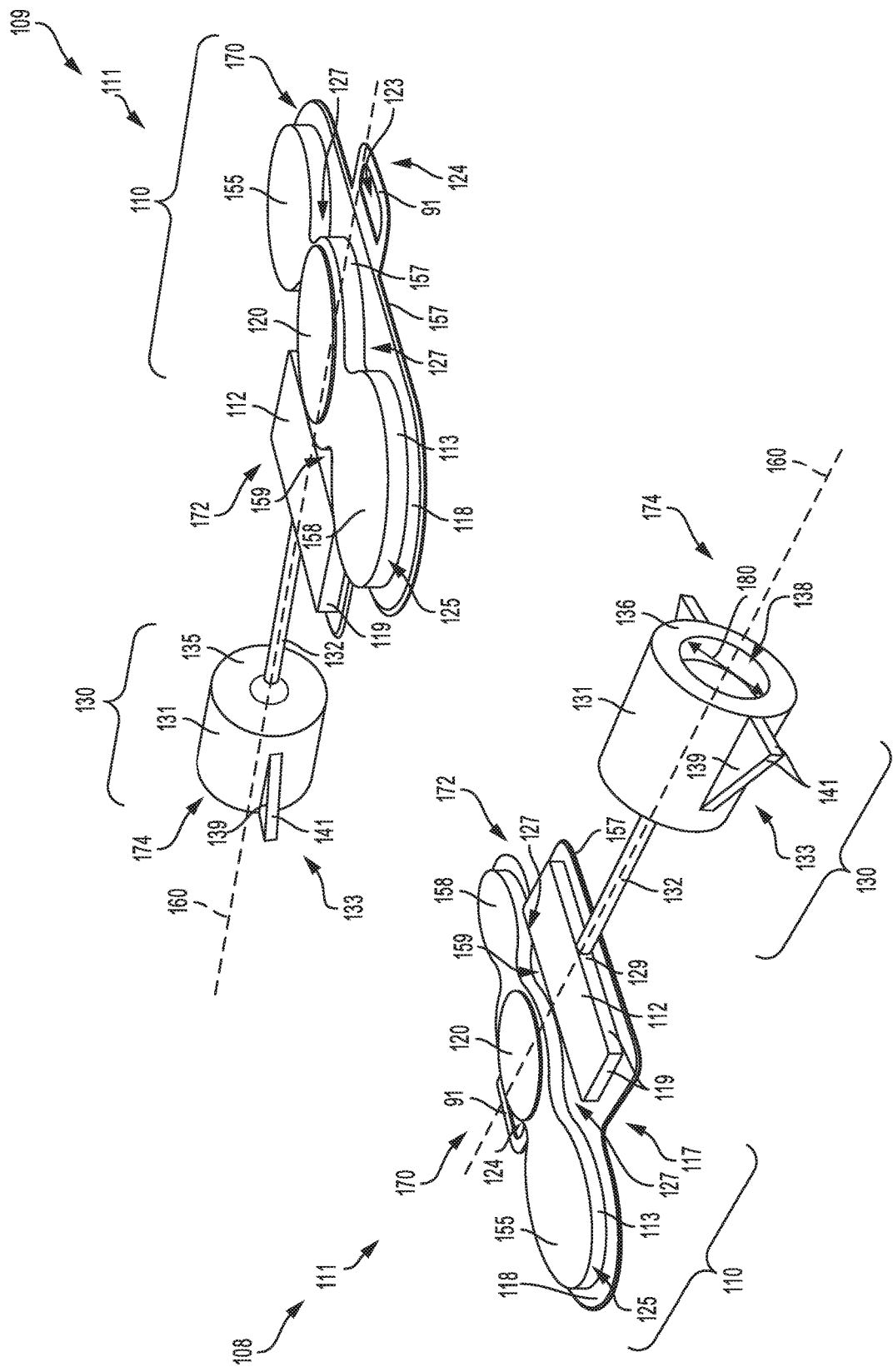

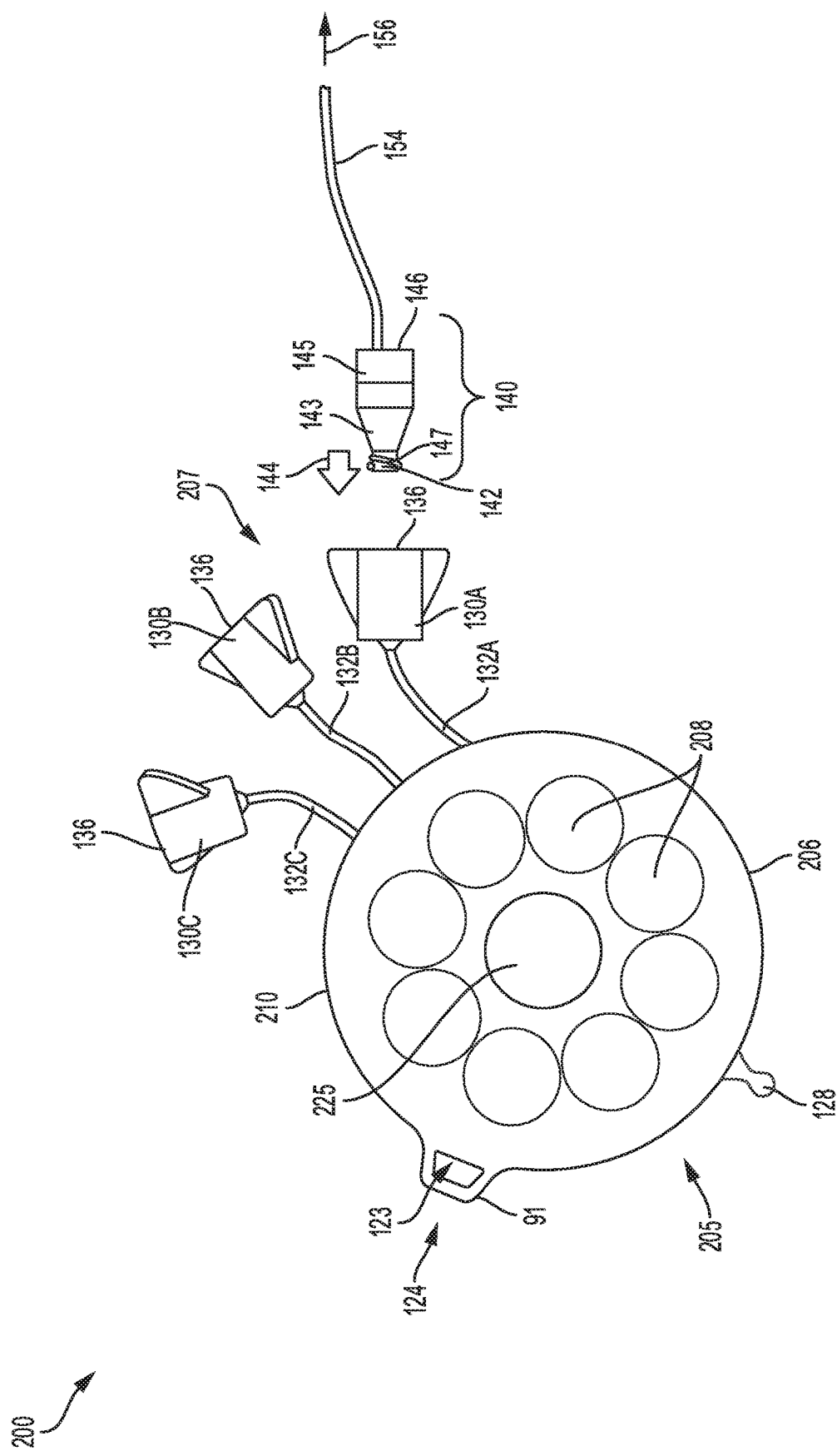

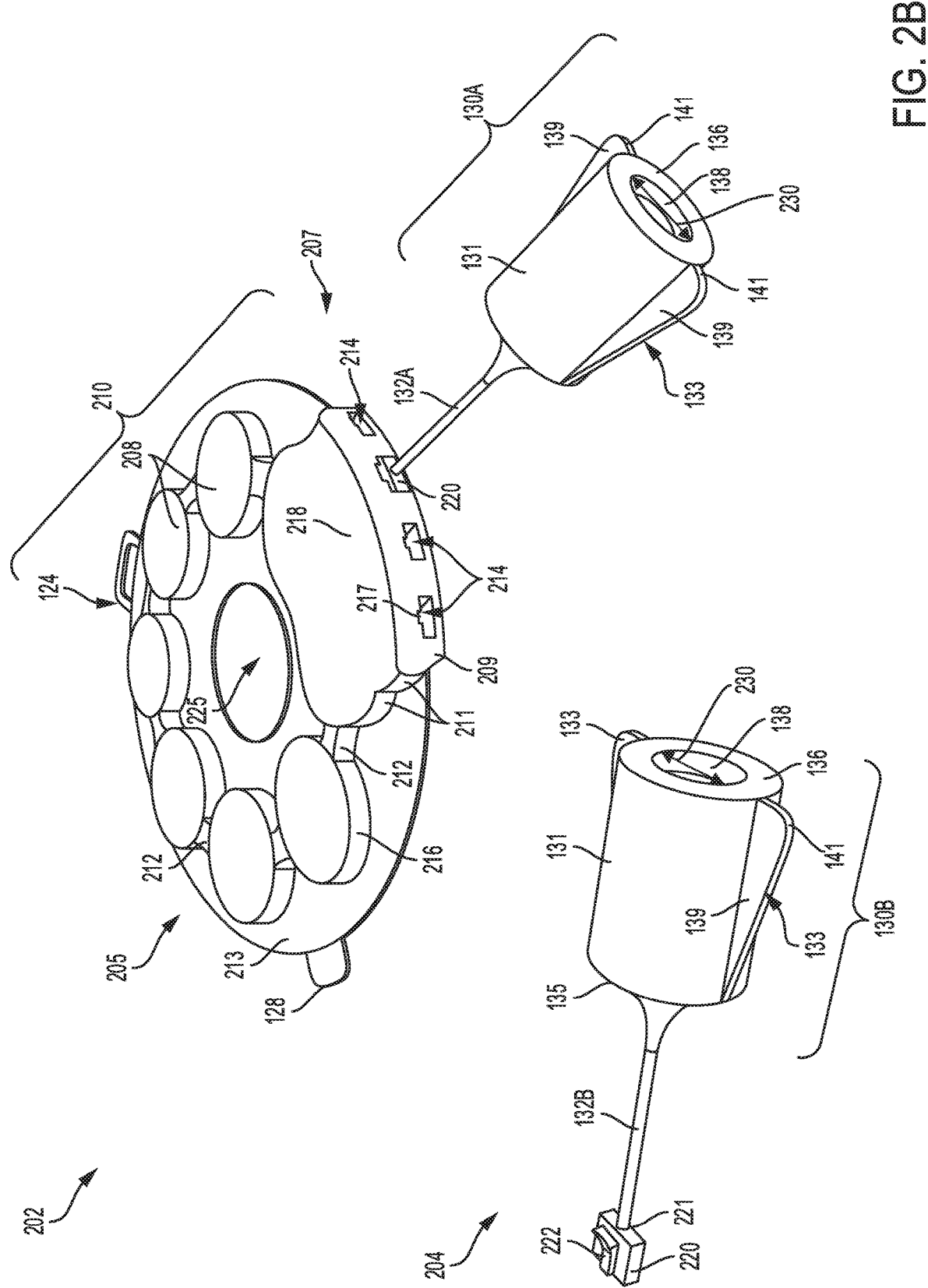

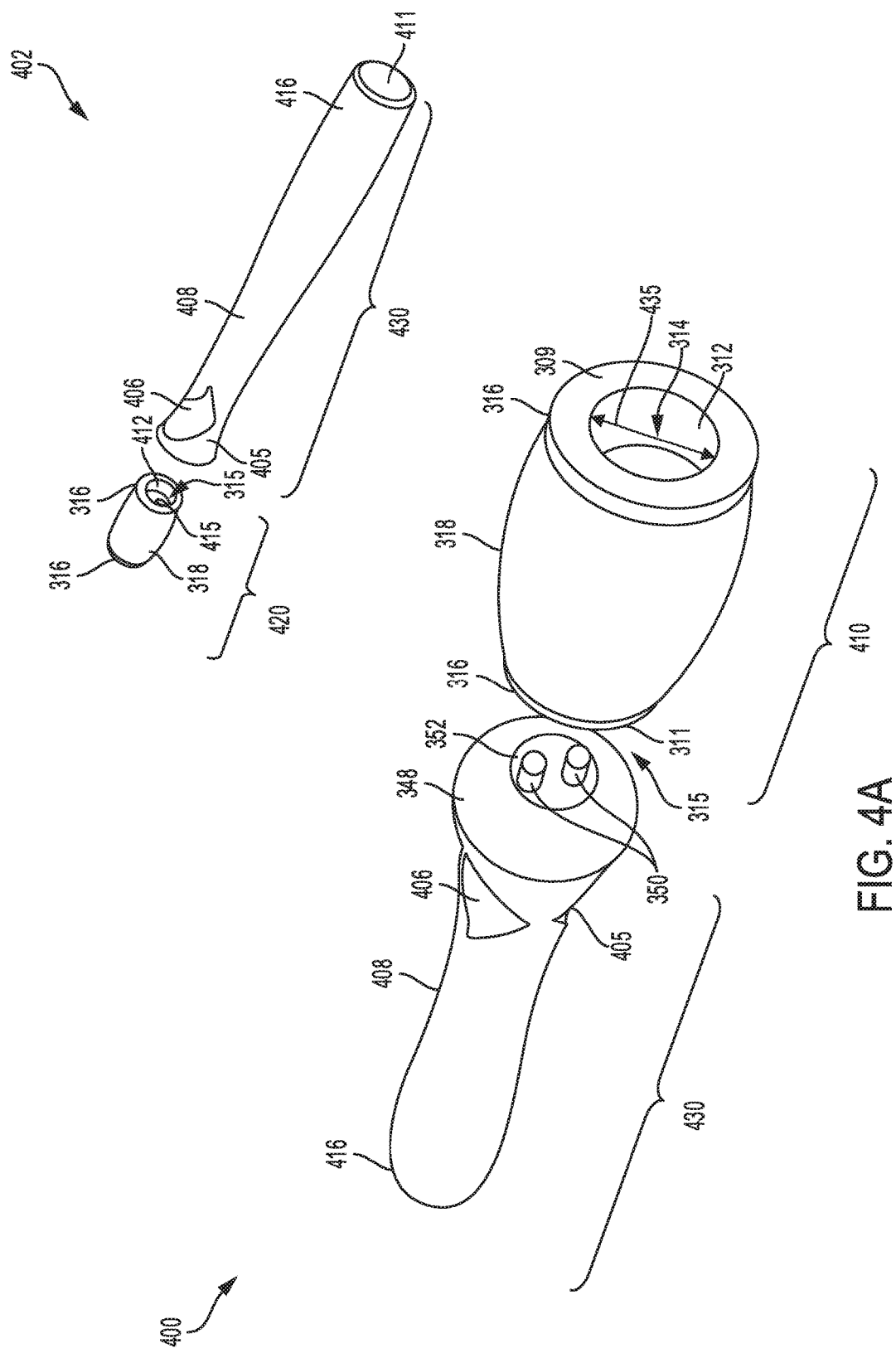

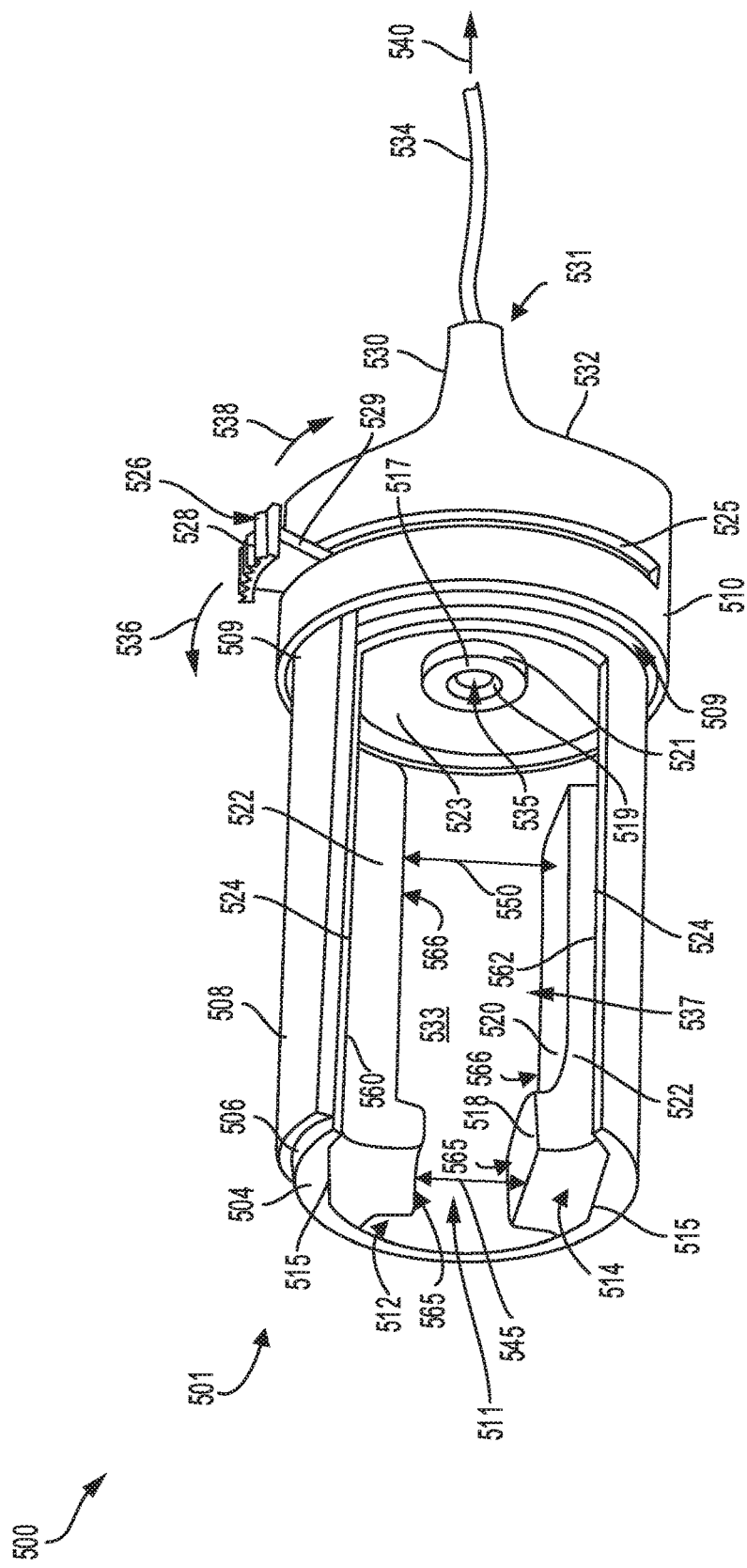

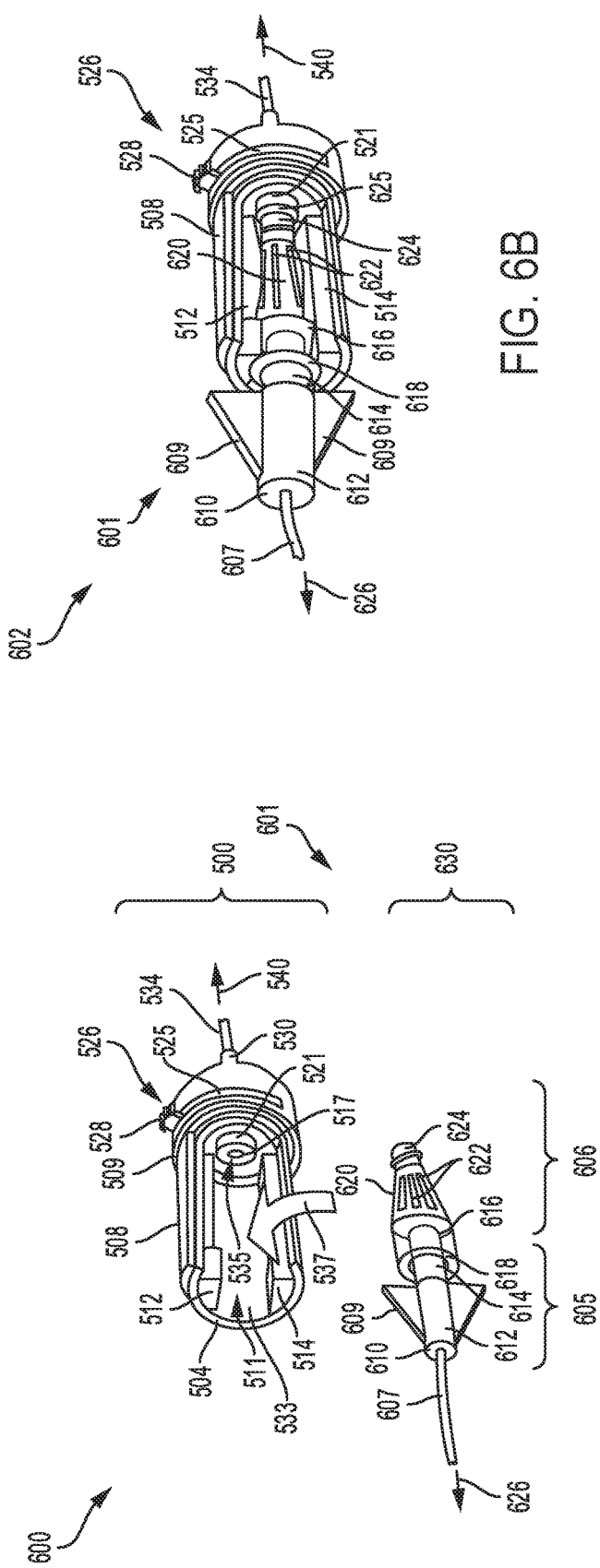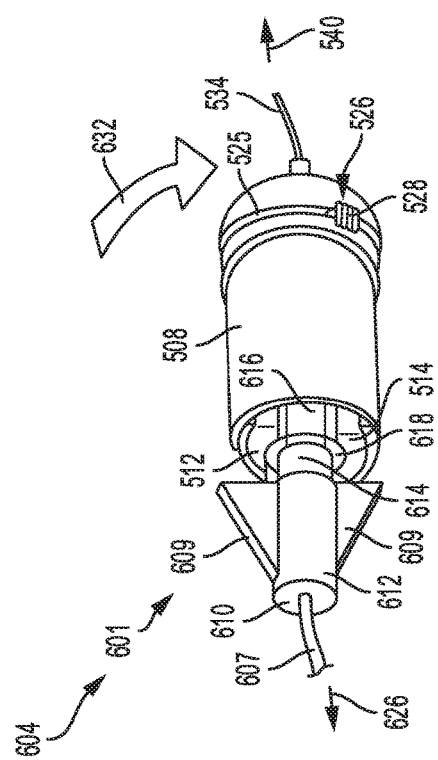

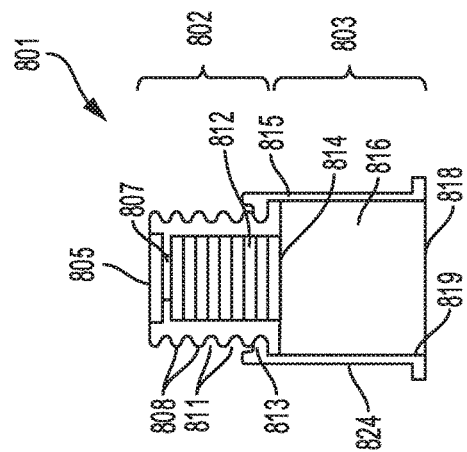
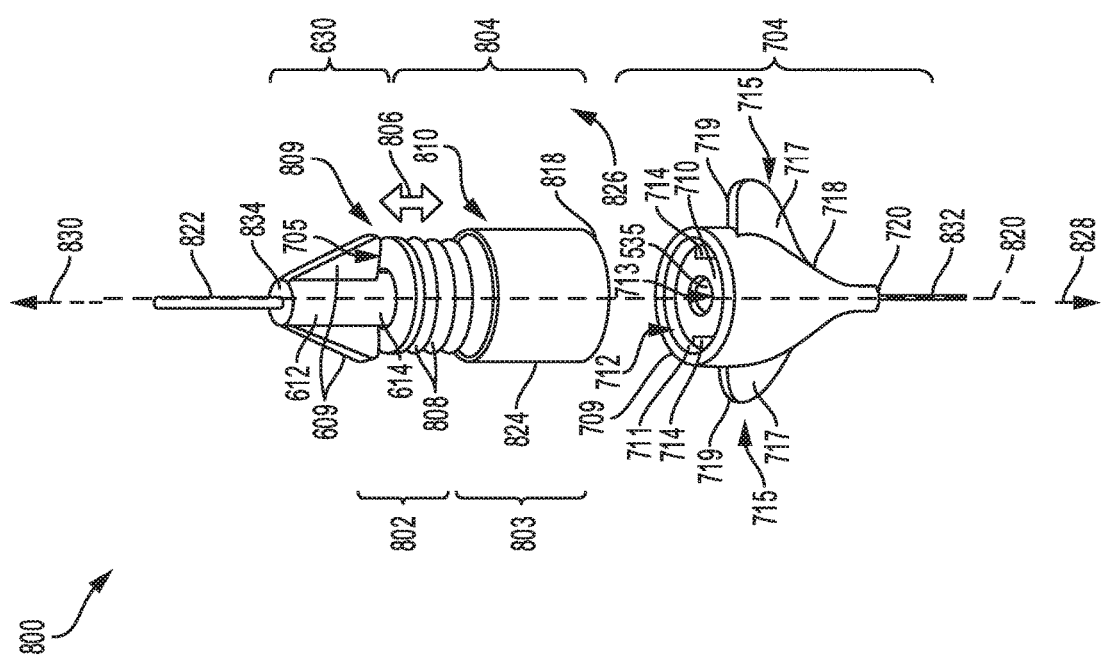
FIG. 8B
FIG. 8A

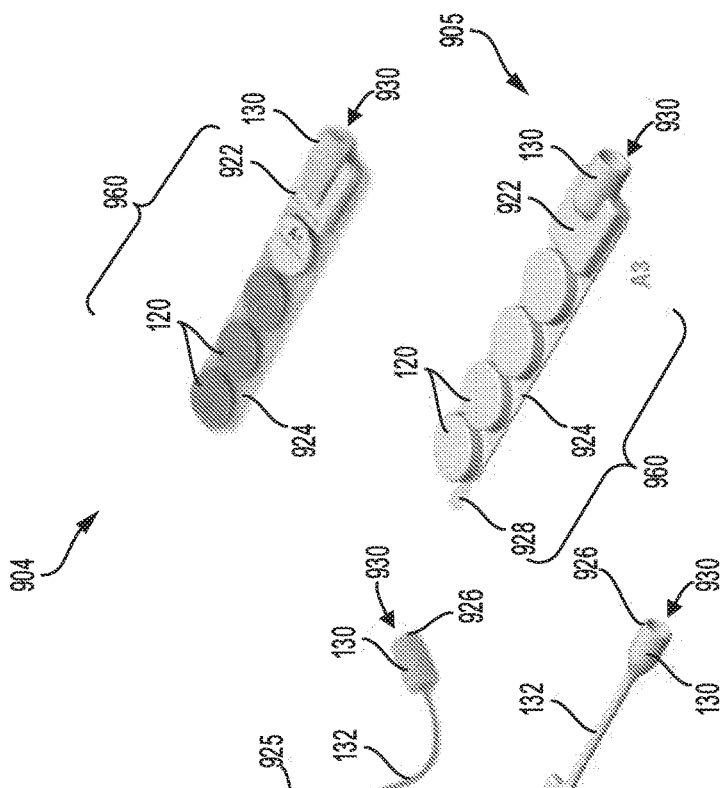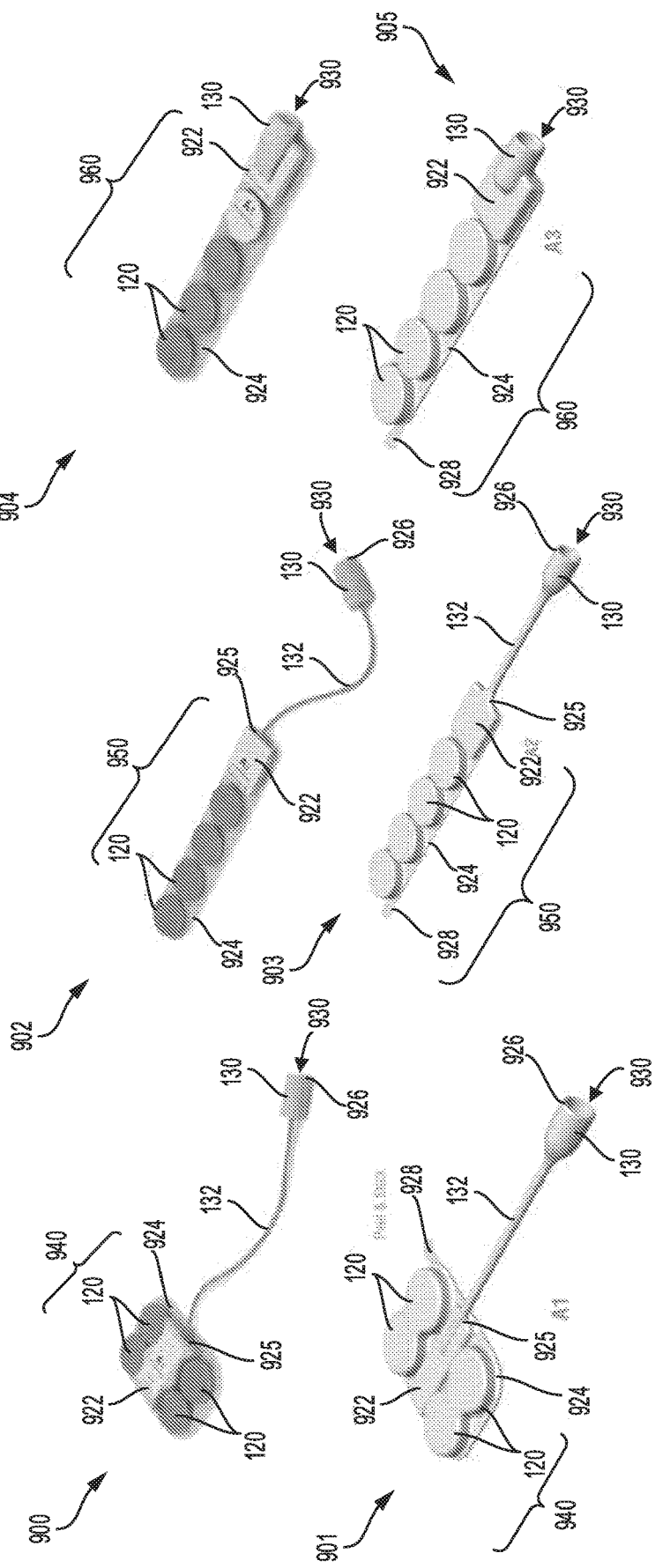

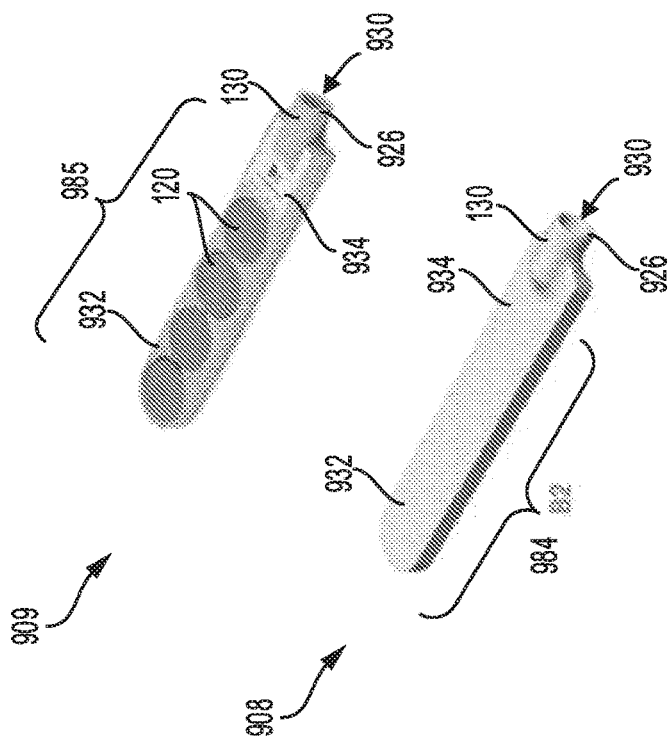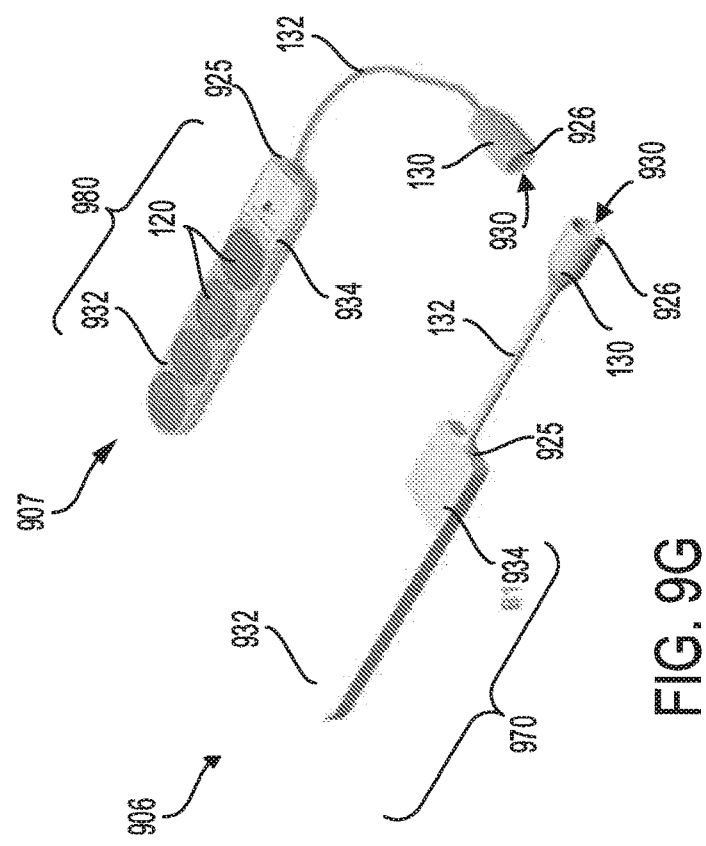

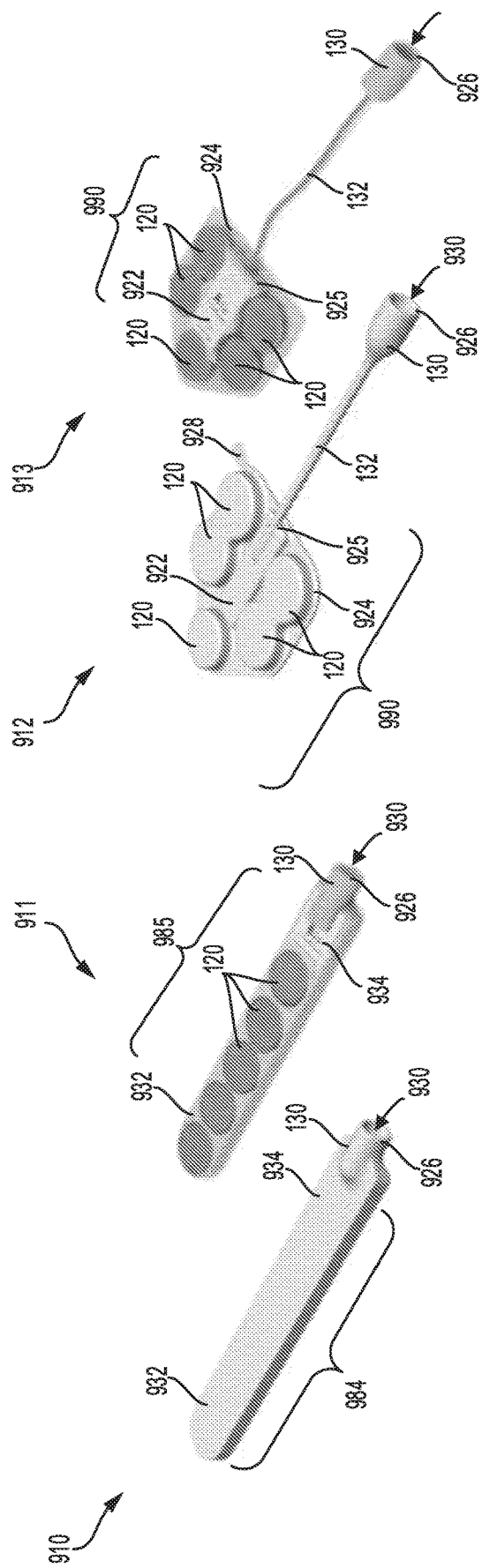

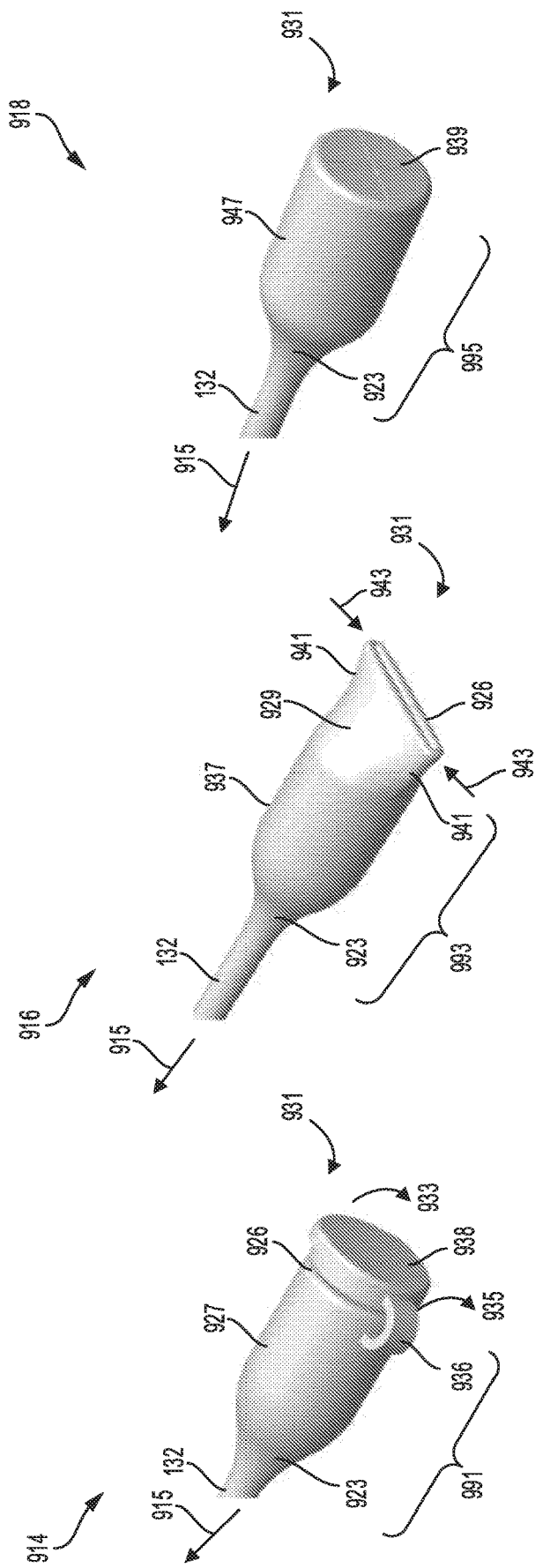

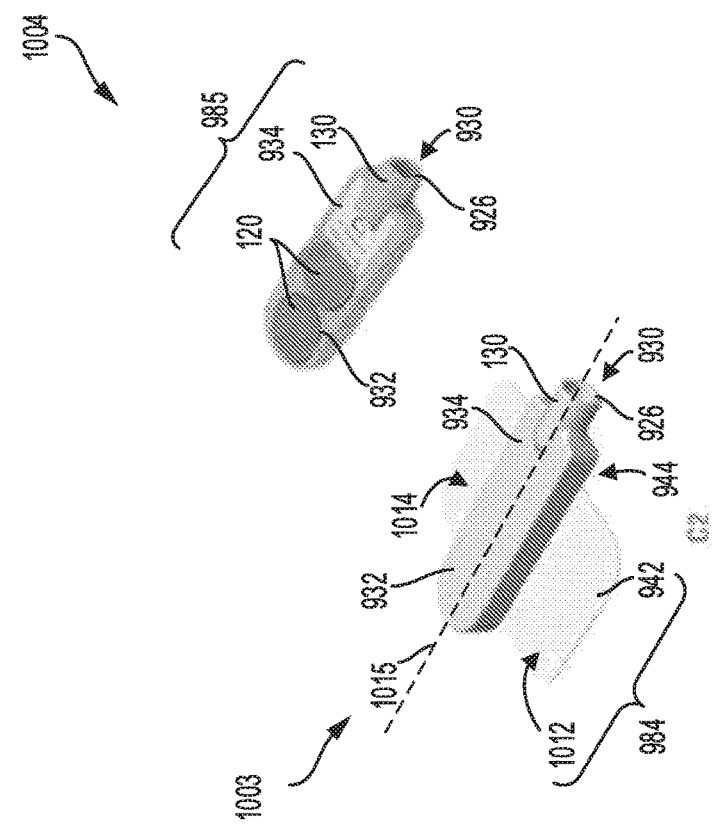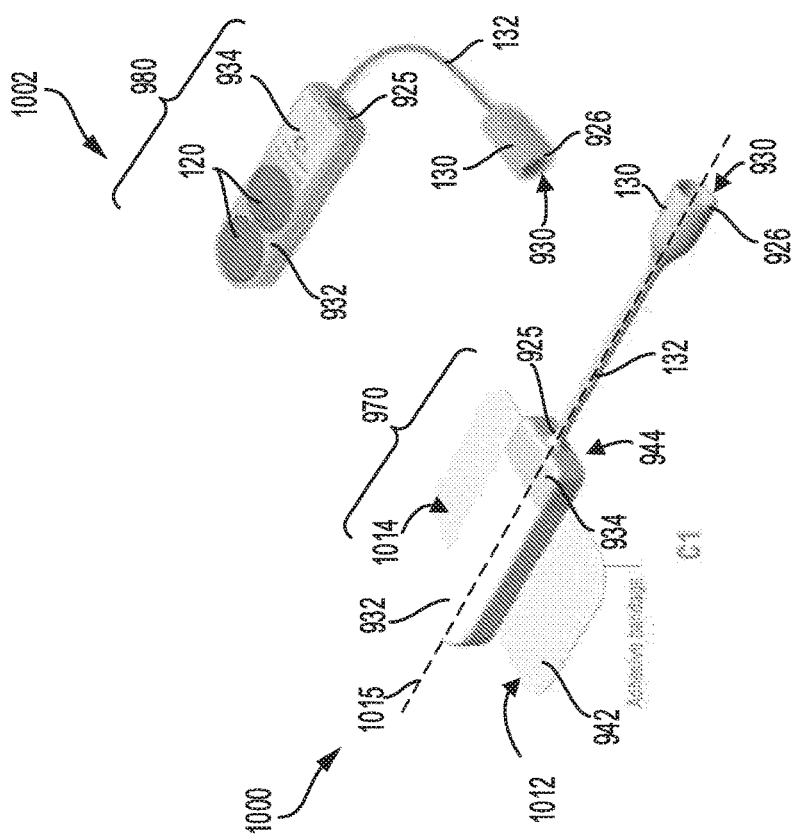

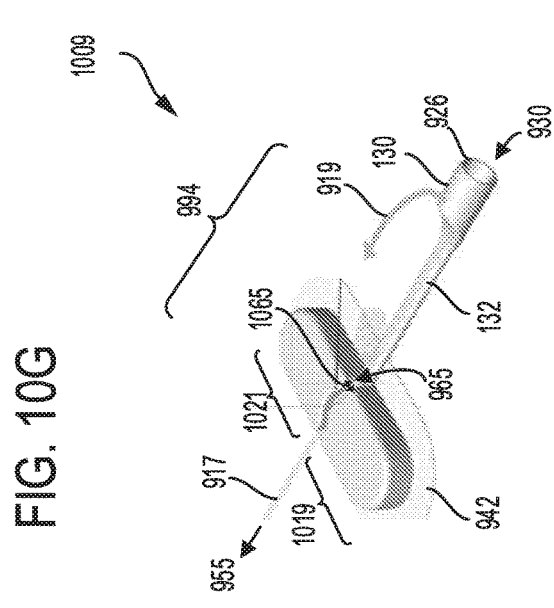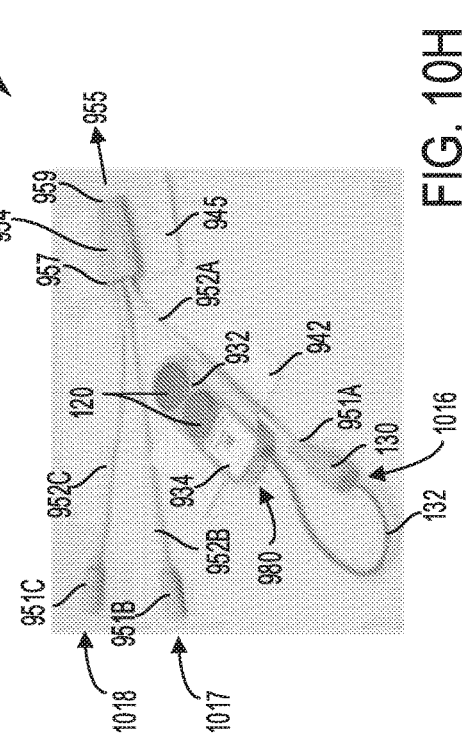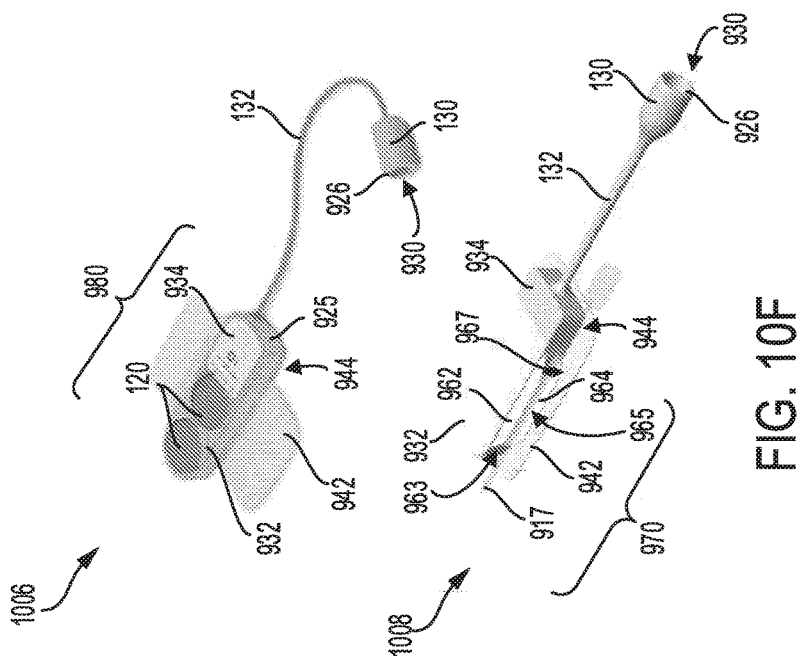

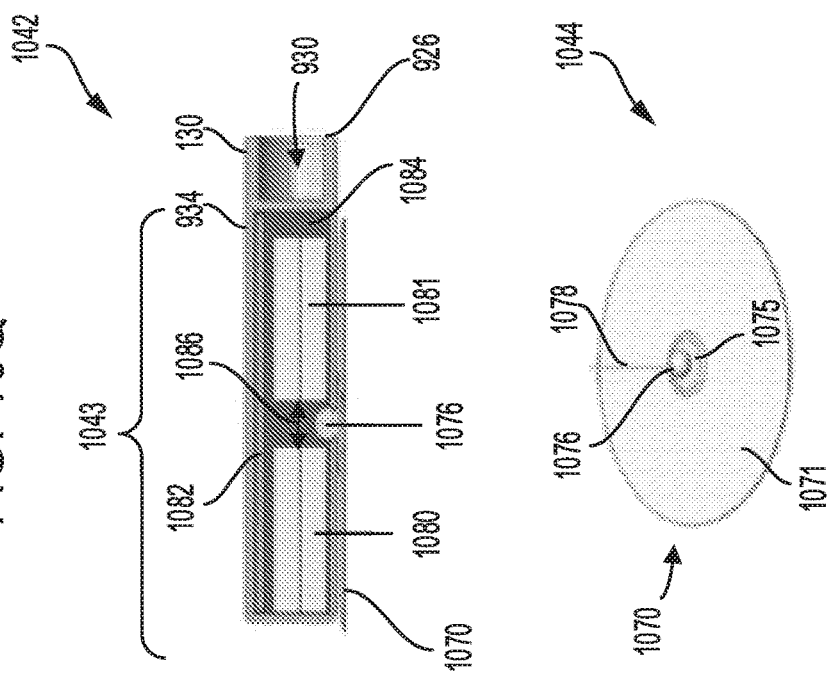

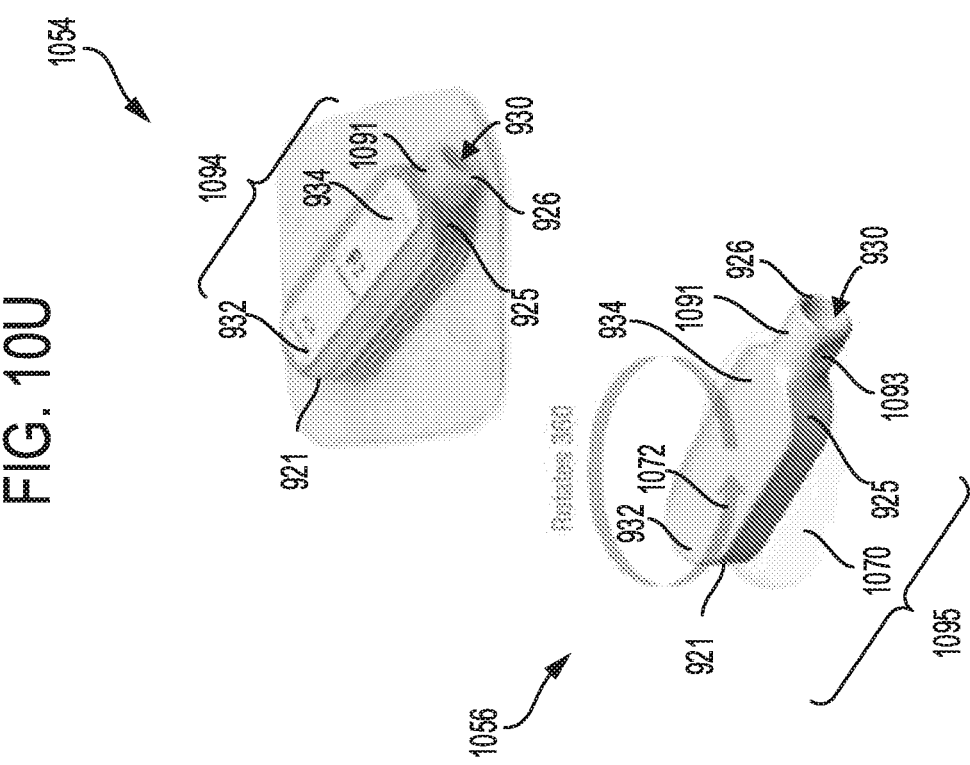
FIG. 10U
FIG. 10V
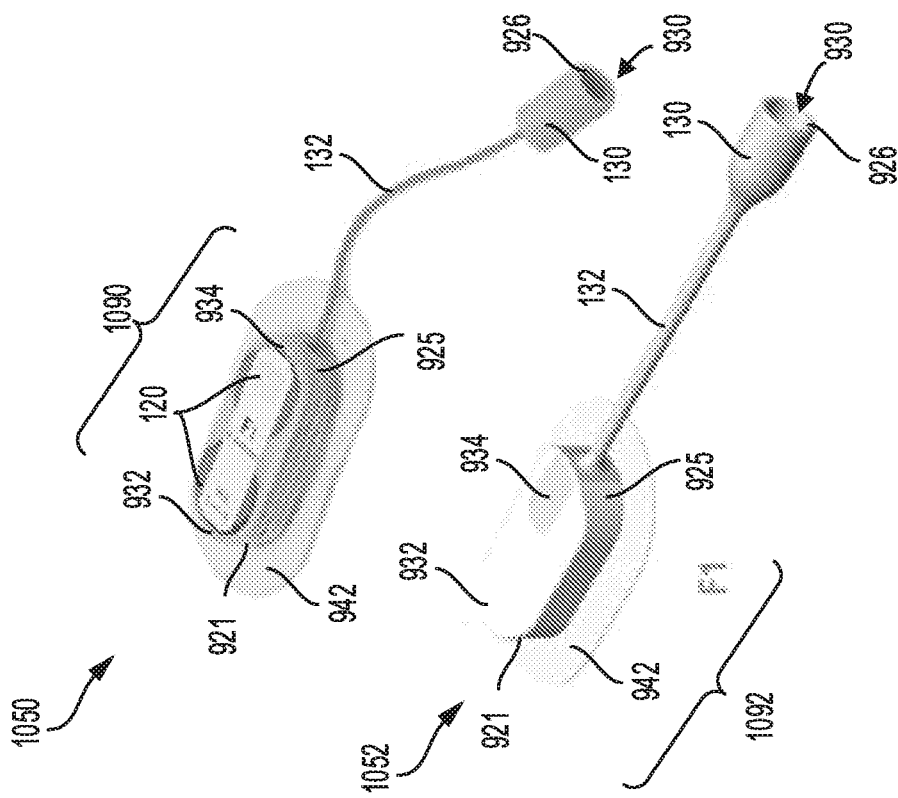
FIG. 10S
FIG. 10T

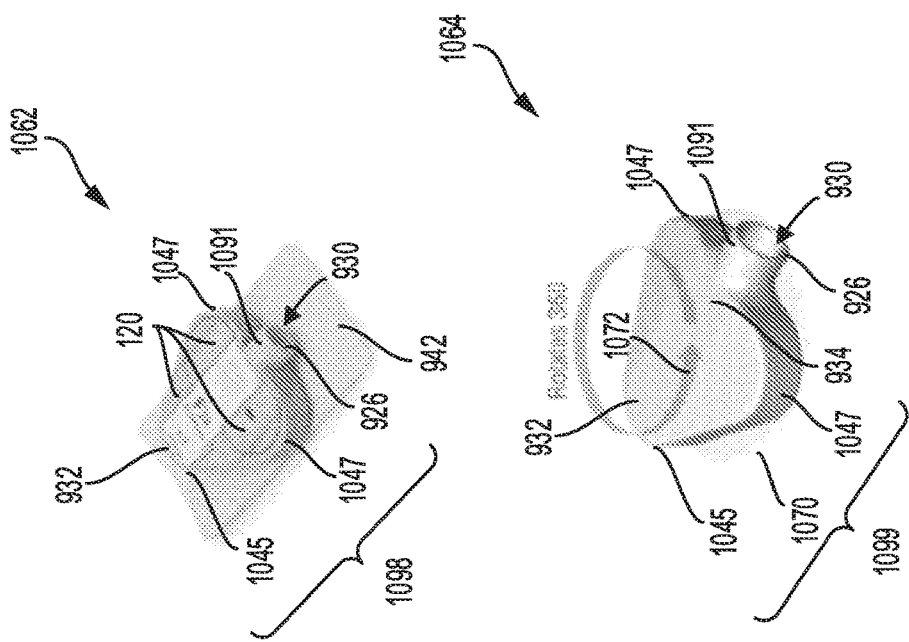
FIG. 10Y
FIG. 10Z
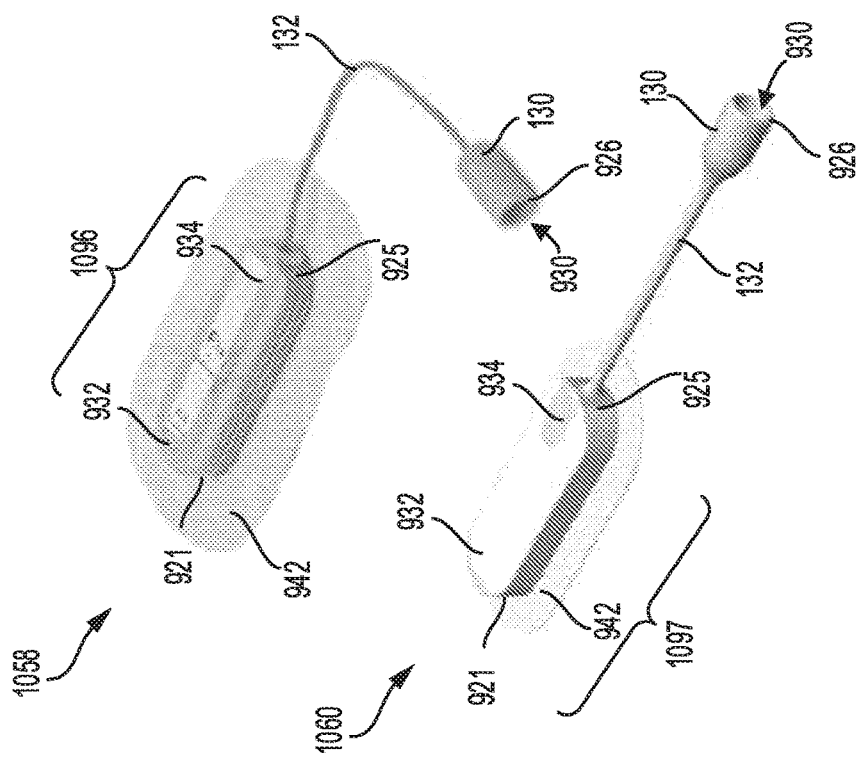
FIG. 10W
FIG. 10X

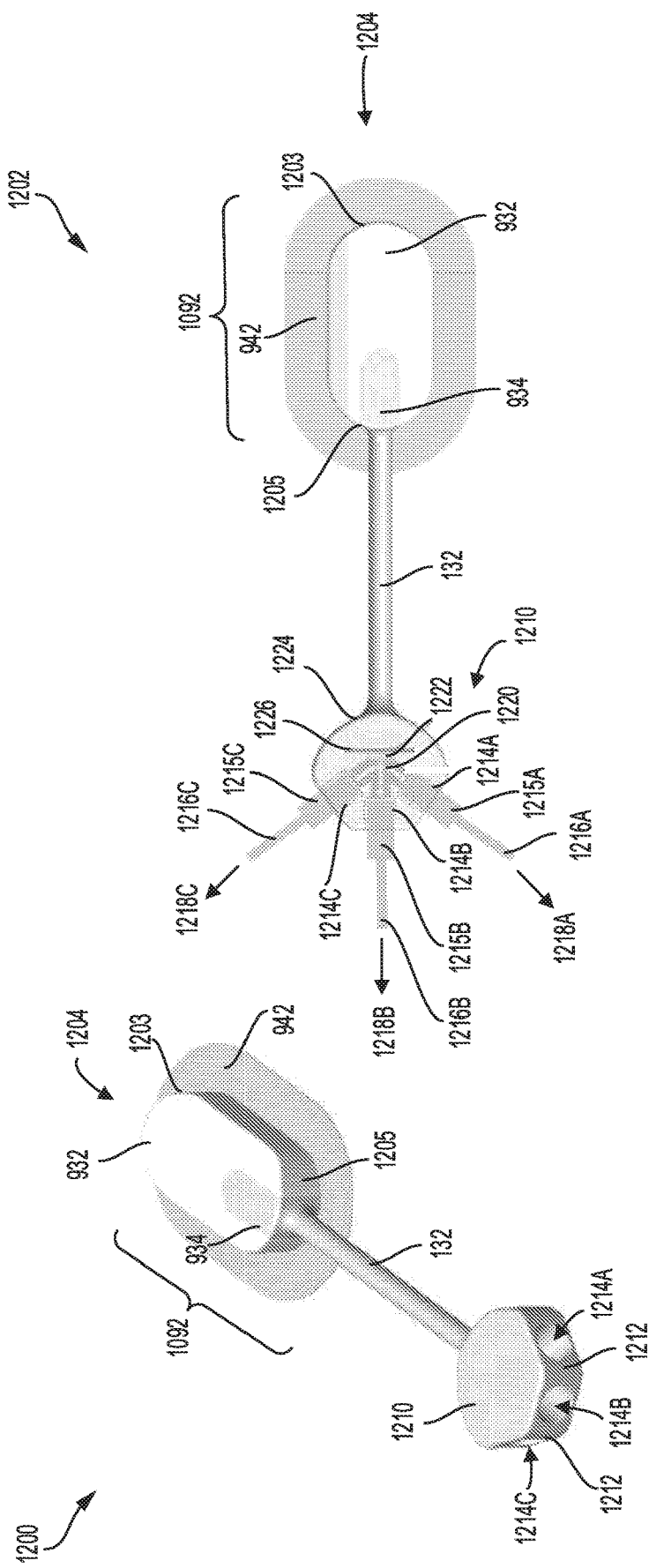

DEVICE AND METHOD FOR STERILIZING A CATHETER SYSTEM

CROSS REFERENCE TO RELATED APPLICATIONS

The present application claims priority to U.S. Provisional Application No. 62/646,201, entitled "DEVICE AND METHOD FOR STERILIZING A CATHETER SYSTEM", and filed on Mar. 21, 2018. The entire contents of the above-listed application are hereby incorporated by reference for all purposes.

TECHNICAL FIELD

The present description relates generally to methods and systems for a medical device for delivering and sampling of fluids and administration of medications to a patient during intravenous therapy.

BACKGROUND AND SUMMARY

Interfacing medical devices such as catheters may be used to administer fluids and medications to patients. For example, a dialysis catheter may be used during intravenous therapy to deliver electrolytes or blood to a patient. Also, catheters may be used to extract fluid samples from the patient for detailed analysis. Interior regions of the catheter device and access sites for catheter installation on the patient may be sterilized to reduce risk of infection and minimize potential for contamination. Various methods including ultra-violet (UV) radiation and alcohol based sterilization are typically used for sterilizing catheters and access sites on patients.

An example catheter is presented by Sikora in US 2008/0306454 A1. Therein, an intravenous port includes an access head and a flexible tube having a lumen. The access head comprises a septum and fluid well to receive fluids or medications. Further, the access head has a signal receptor that is electrically connected to an ultraviolet light source. Also, a transmitter is provided to deliver electrical signals from a power source to the UV light source. During operation, a saline solution may be injected into the intravenous port to transmit the UV radiation through the flexible tube.

However, the inventors have recognized potential issues with such an intravenous port design. For example, the saline solution injected into the fluid well during sterilization, is needed to transmit the UV radiation through the catheter as well as detach microorganisms from internal walls of the lumen. The use of the saline solution may cause unnecessary burden and increased operating costs. Also, since the intravenous unit is not configured to be connected to another battery source if the existing power source is depleted, the unit may be rendered inoperable if the power source in the unit is exhausted.

The inventors herein have developed a catheter design to address some of issues noted above. In one example, a catheter access port cleaning, disinfection or sterilization device, comprising: a first housing comprising a power source and control circuit; a second housing shaped to mate with a catheter and having a first ultra-violet light source that is non-visible to a human eye mounted therein, the first housing wired to the second housing to power the light source; wherein the light source is configured to emit ultraviolet light of a predetermined wavelength of 100-280 nm that is directed to disinfect the catheter access port for a duration of 1 second to 10 minutes; further wherein a visible light indicator is mounted to the access port to indicate status of the device by flashing a visible color when the ultraviolet light is emitted from the light source. In this way, one design of the catheter device may be used to clean, disinfect or sterilize the catheter access port using ultra-violet radiation from the UV light source mounted inside a luer port coupled to a luer device. For example, the UV light source may be activated when the luer device is inserted into the luer port, and connected to an electrical power source inside one or more catheter head units. When activated, the UV light source emits ultra-violet C (UV-C) to sterilize interior areas of the catheter and access sites on a patient during intravenous therapy. In this way, the catheter device may be used to sterilize interior regions of the device and access sites on the patient to reduce occurrence of infections and contamination. The approach disclosed herein confers various advantages. For example, the sterilization procedure may be conducted automatically to provide an effective means of cleaning the catheter while minimizing patient infections. Further, the catheter system may comprise a plurality of stacked catheter head units to provide adequate electrical power and reduce disruptions in catheter operation.

It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

FIG. 1D shows a first view of a second embodiment of a catheter device.

FIG. 1E shows a second view of the second embodiment of the catheter device.

FIG. 1F shows a first view of a third embodiment of a catheter device.

FIG. 1G shows a second view of the third embodiment of the catheter device.

FIG. 2A shows a fourth embodiment of a catheter device having a plurality of luer ports for connecting to a luer device.

FIG. 2B shows a fifth embodiment of a catheter device having a plurality of luer ports.

FIG. 4A shows a seventh embodiment of a catheter device with a single luer port for connecting to a luer device and a portable power source.

FIG. 4B shows a shows an eighth embodiment of a catheter device with a single luer port for connecting to a luer device and a portable power source.

FIG. 5 shows an alternative embodiment of a single luer port to receive a luer device.

FIG. 6A shows a first view of a ninth embodiment of a catheter device with the single luer port configured with a main opening to receive a luer device.

FIG. 6B shows a second view of the ninth embodiment of the catheter device, with a retractable cover of the port adjusted to an open position and the luer device mounted in the main opening of the luer port.

FIG. 6C shows a third view of the ninth embodiment of the catheter device, with the retractable cover adjusted to a closed position.

FIG. 8A shows an eleventh embodiment of a catheter device, with the luer device mounted in a sterilization activation device that is coupleable to the sterilization port.

FIG. 8B shows a cross sectional view of the sterilization activation device of the eleventh embodiment of the catheter device.

FIGS. 9A-9B show a twelfth and a thirteenth embodiment, respectively of a sterilization device configured with a head unit having a plurality of batteries, and coupled to a luer port.

FIGS. 9C-9D show a fourteenth and a fifteenth embodiment, respectively of a sterilization device configured with a head unit having a plurality of batteries, and coupled to a luer port.

FIGS. 9E-9F show a sixteenth and seventeenth embodiment, respectively of a sterilization device configured with a head unit having a plurality of batteries and a luer port.

FIGS. 9G-9H show an eighteenth and a nineteenth embodiment, respectively of a sterilization device configured with a plurality of batteries and a luer port.

FIGS. 9I-9J show a twentieth and a twenty first embodiment, respectively of a sterilization device configured with a plurality of batteries and a luer port.

FIGS. 9K-9L show alternative embodiments of the sterilization device configured with a head unit having a plurality of batteries and a luer port.

FIGS. 9M-9N show a twenty second and a twenty third embodiment, respectively of a sterilization device configured with a head unit having a plurality of batteries, and coupled to a luer port.

FIG. 9O shows a first embodiment of a cap for sealing a luer port of the sterilization device.

FIG. 9P shows a second embodiment of a cap for sealing a luer port of the sterilization device.

FIG. 9Q shows a third embodiment of a cap for sealing a luer port of the sterilization device.

FIG. 10A shows a twenty fourth embodiment of a sterilization device configured with a head unit having a plurality of stacked batteries; the head unit is attached to an adhesive pad, and connected to a luer port.

FIG. 10B shows a twenty fifth embodiment of a sterilization device configured with a head unit with a plurality of stacked batteries, and connected to a luer port.

FIG. 10C shows a twenty sixth embodiment of a sterilization device configured with a head unit having a plurality of stacked batteries and a luer port; the head unit is attached to an adhesive pad.

FIG. 10D shows a twenty seventh embodiment of a sterilization device configured with a head unit having a plurality of stacked batteries and a luer port.

FIG. 10E shows a twenty eighth embodiment of a sterilization device configured with a head unit having a plurality of stacked batteries; the head unit is attached to an adhesive pad, and connected to a luer port.

FIG. 10F shows a twenty ninth embodiment of a sterilization device configured with a head unit having a plurality of stacked batteries; the head unit is attached to an adhesive pad, and connected to a luer port.

FIG. 10G shows a thirtieth embodiment of a sterilization device configured with a head unit having a plurality of stacked batteries, a first adhesive pad, and a plurality of luer ports connected to a splicer unit attached to a second adhesive pad.

FIG. 10H shows a thirty first embodiment of a sterilization device configured with a head unit having a plurality of stacked batteries; the head unit is attached to an adhesive pad, and connected to a luer port.

FIG. 10O shows a thirty eighth embodiment of a sterilization device with a head unit having a plurality of stacked batteries, and a luer port; the head unit is attached to an adhesive pad with a ball that allows the head unit to rotate.

FIG. 10P shows a thirty ninth embodiment of a sterilization device with a head unit having a plurality of stacked batteries, and a luer port; the head unit is attached to an adhesive pad with a ball that allows the head unit to rotate about a fixed location.

FIG. 10Q shows a cross sectional view through a sterilization head unit having stacked batteries, and a luer port; the head unit is attached to an adhesive pad with a ball that allows the head unit to rotate about a fixed point.

FIG. 10R shows a schematic view of the circular adhesive pad with the ball and a vertical rod for attaching to a sterilization head unit.

FIG. 10S shows a fortieth embodiment of a sterilization device having a head unit with a plurality of stacked batteries; the head unit attached to an adhesive pad, and connected to a luer port.

FIG. 10T shows a forty first embodiment of a sterilization device with a head unit having a plurality of stacked batteries, and a luer port; the head unit is attached to an adhesive pad with a ball that allows the head unit to rotate.

FIG. 10U shows a forty second embodiment of a sterilization device with a head unit having a plurality of stacked batteries, and a luer port.

FIG. 10V shows a forty third embodiment of a sterilization device having a head unit attached to an adhesive pad with a ball that allows the head unit to rotate about a fixed point.

FIG. 10W shows a forty fourth embodiment of a sterilization device with a head unit having a plurality of stacked batteries; the head unit attached to an adhesive pad, and connected to a luer port.

FIG. 10X shows a forty fifth embodiment of a sterilization device with a head unit having a plurality of stacked batteries, and a luer port; the head unit is attached to an adhesive pad with a ball that allows the head unit to rotate.

FIG. 10Y shows a forty sixth embodiment of a sterilization device with a head unit having a plurality of stacked batteries, and a luer port; the head unit is attached to an adhesive pad.

FIG. 10Z shows a forty seventh embodiment of a sterilization device with a head unit having a plurality of stacked batteries, and a luer port; the head unit is attached to an adhesive pad with a ball that allows the head unit to rotate about a fixed point.

FIG. 12A shows a fifty sixth embodiment of a catheter device with a head unit attached to an adhesive pad, and connected to a distribution unit having a plurality of ports.

FIG. 12B shows the catheter device with a plurality of catheter lines coupled to the distribution unit containing a UV light source.

FIGS. 1A-12B are shown to scale, although other relative dimensions may be used, if desired.

DETAILED DESCRIPTION

Figure 1A:
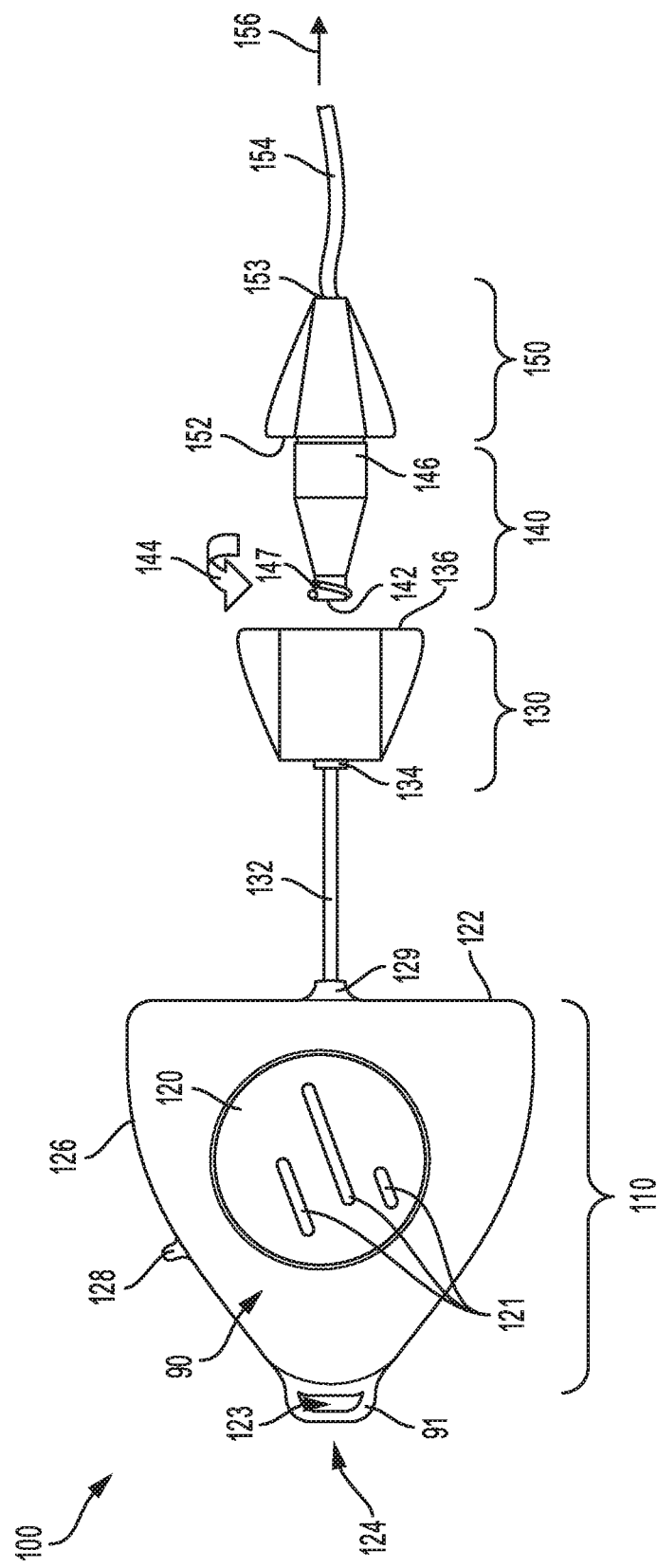
FIG. 1A shows a first embodiment of a catheter device used for intravenous therapy.
Figure 1B:
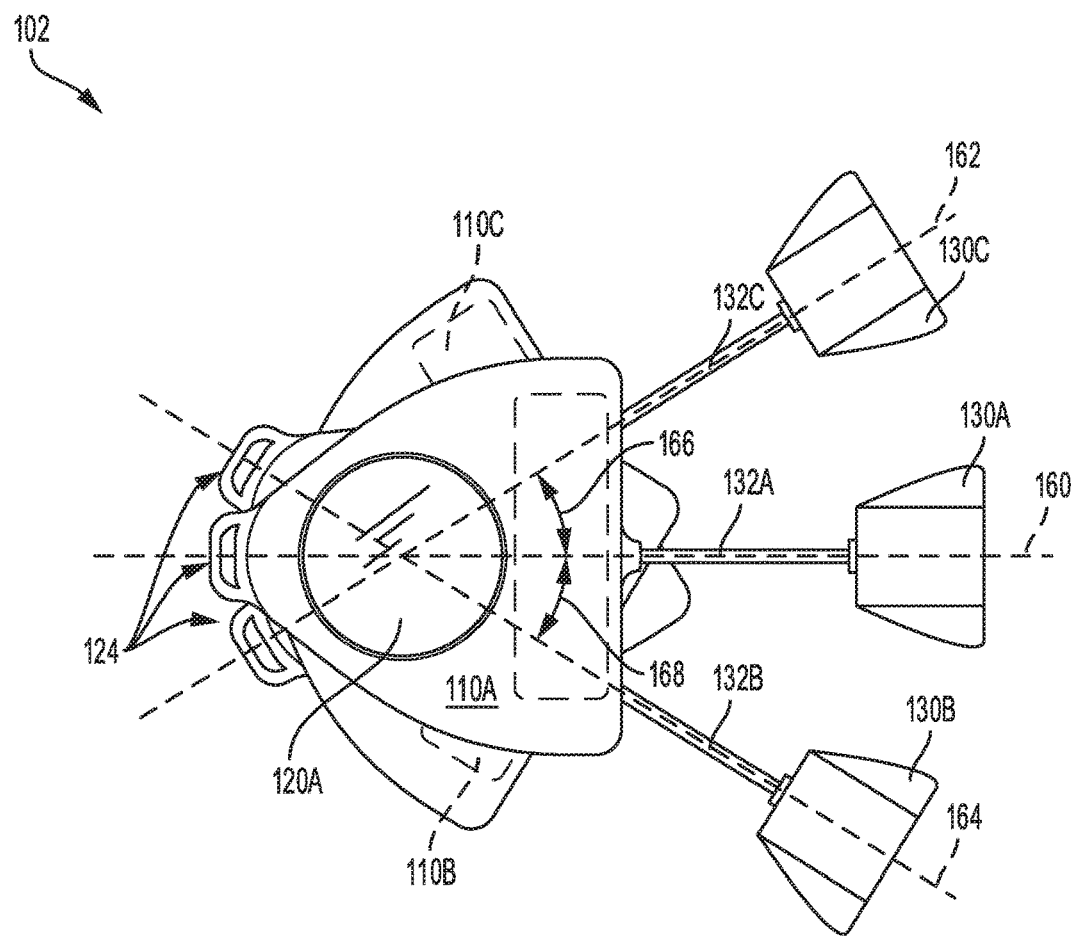
FIG. 1B shows a first view of a plurality of stacked catheter units of the first embodiment of the catheter device.
Figure 1C:
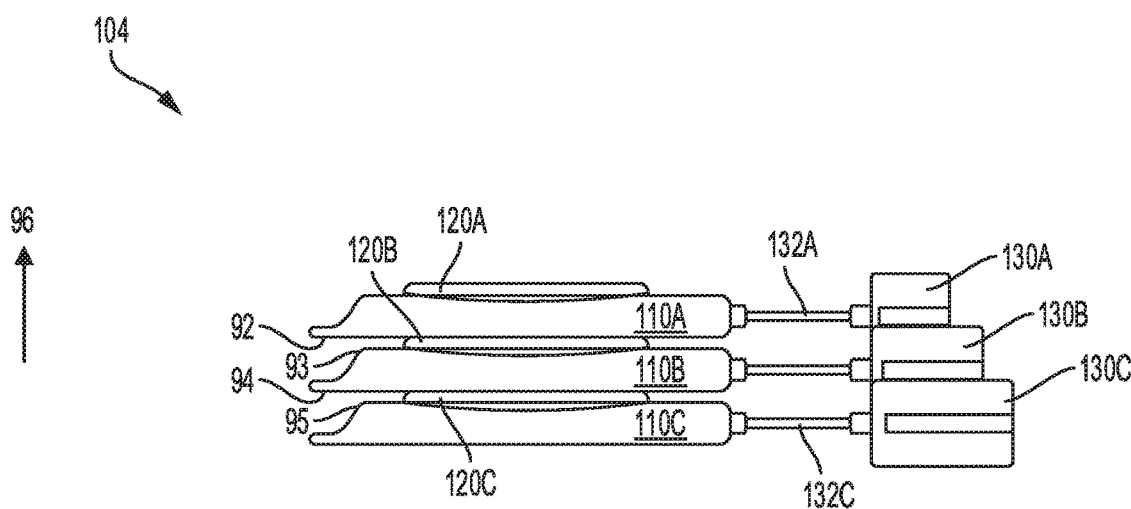
FIG. 1C shows a second view of the stacked catheter units of the first embodiment of the catheter device.

The following description relates to a catheter, such as the catheter device shown in FIG. 1A. The catheter device comprising various components, may be used for intravenous therapy. As shown in FIG. 1A, a first embodiment of a catheter device may comprise: a catheter head unit containing one or more batteries, a luer port coupled to the catheter head unit via a connection line, a luer device coupled to a distal end of the luer port, and a catheter line fluidly connected to the luer device and access sites on a patient. A plurality of catheter head units may be electrically connected by stacking two or more head units together to provide an adequate source of electrical power to operate the catheter device, as shown in FIGS. 1B-1C. A first and second view of a second embodiment of a catheter device configured with a head unit having a single luer port, are shown in FIGS. 1D-E, respectively. A first and second view of a third embodiment of a catheter device configured with a head unit having a single luer port, are shown in FIGS. 1F-1G, respectively. Each of the luer ports of the catheter devices shown in FIGS. 1D-1G, may be coupled to a luer device having a flexible tube connected to one or more access sites on the patient. A fourth and fifth embodiment of a catheter device configured with a head unit having a plurality of luer ports, are shown in FIGS. 2A-2B. In each of the fourth and fifth embodiment of the catheter device, each luer port may be coupled to a luer device, thereby allowing the catheter system to couple to a plurality of access sites on the patient.

Figure 3A:
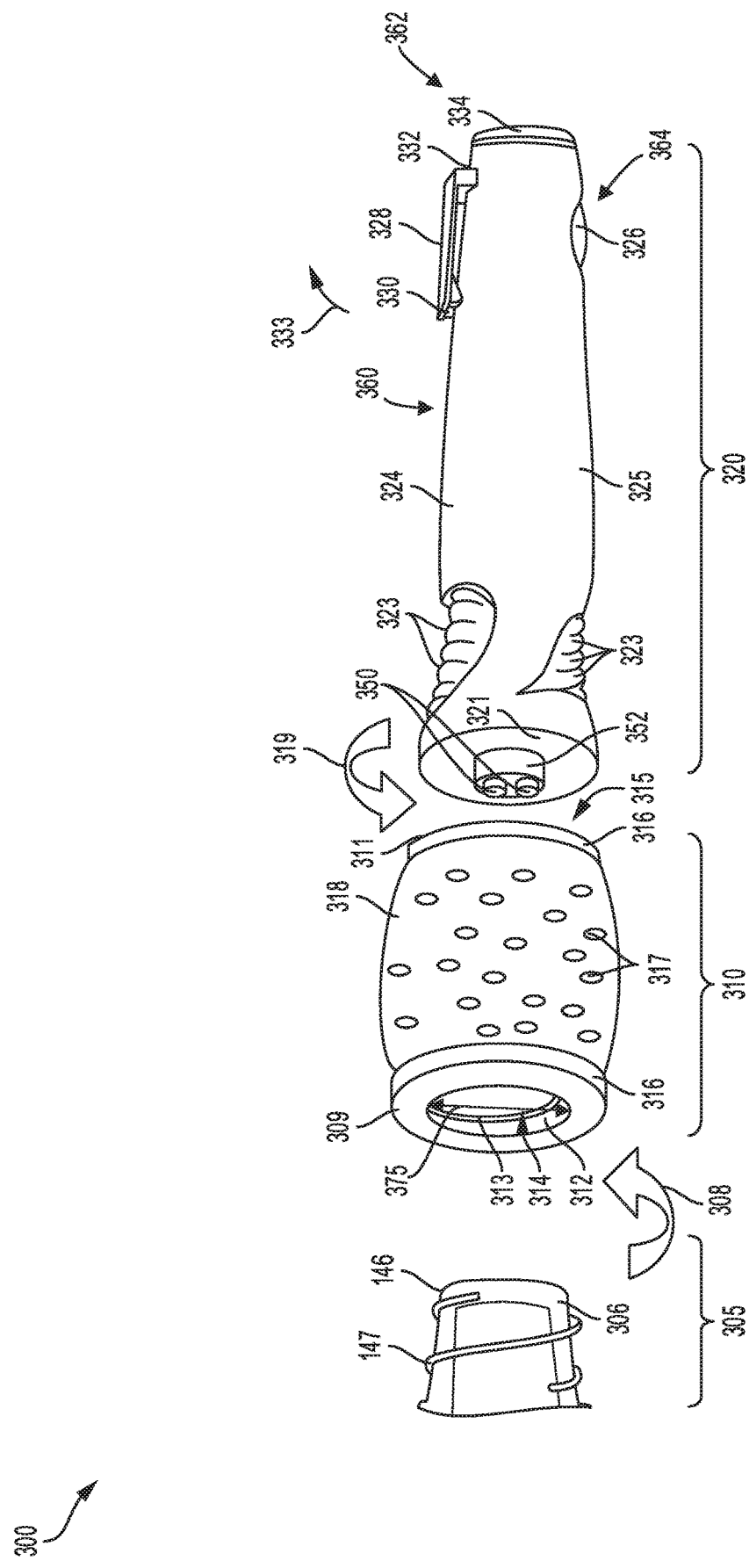
FIG. 3A shows a sixth embodiment of a catheter device configured with a luer device, a single luer port and a portable power source.
Figure 3C:
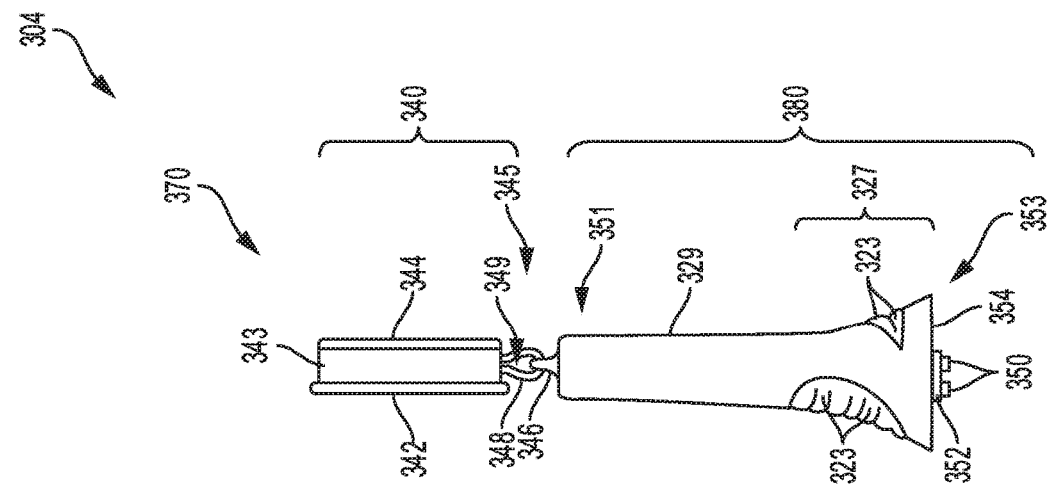
FIG. 3C shows a second view of the alternative embodiment of the portable power source.
Figure 3B:
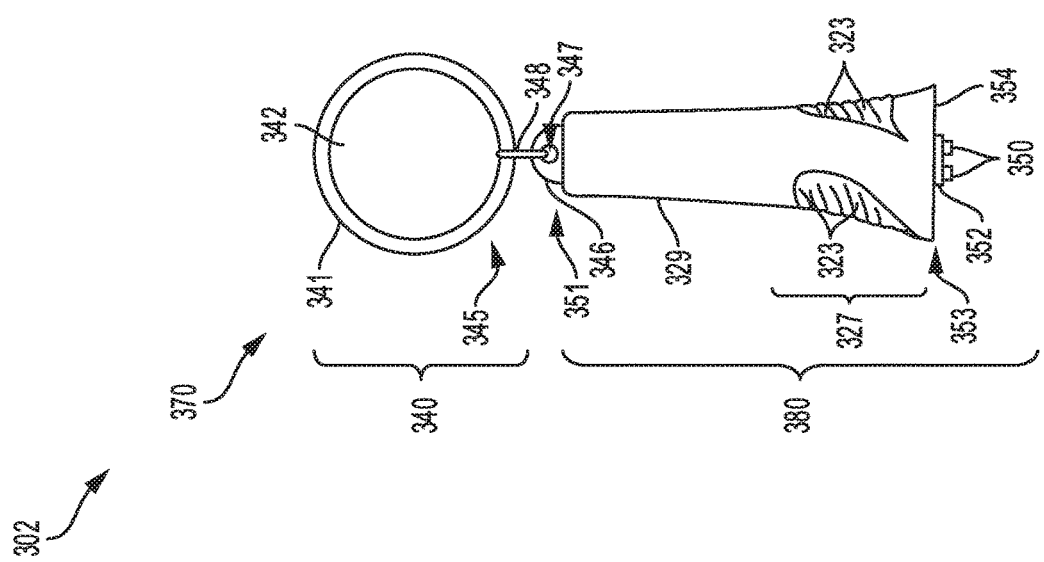
FIG. 3B shows a first view of an alternative embodiment of the portable power source.

FIG. 3A shows a sixth embodiment of a catheter device configured with a luer port and a high intensity power source, including a luer device that may be coupled to access sites on the patient. The high intensity power source may be configured to provide electrical power to activate a UV light source mounted in the luer port. A first and second view of an alternative embodiment of the high intensity power source is shown in FIGS. 3B-3C, respectively. FIGS. 4A-4B show a seventh and an eighth embodiment, respectively of a catheter device configured with a luer port and a power source. Each luer port of the seventh and an eighth embodiment of the catheter device includes a cylindrical annular body having a main opening which connects to an upstream end of the power source. Further, an upstream end of the main opening may be connected to a luer device coupled to access sites on the patient. FIG. 5 shows an alternative embodiment of a luer port that couples to a luer device that may be connected to an access site on the patient. An upstream end of the luer port includes an opening to receive the luer device, as shown in FIGS. 6A-6C where a ninth embodiment of a catheter device is depicted. A downstream end of the luer port may be coupled via a flexible cable to an electrical power source mounted in a catheter head unit, such as the head unit 110 disclosed with reference to FIG. 1A. An example procedure for installing the luer device into the luer port is disclosed in FIGS. 6A-6C.

Figure 7:
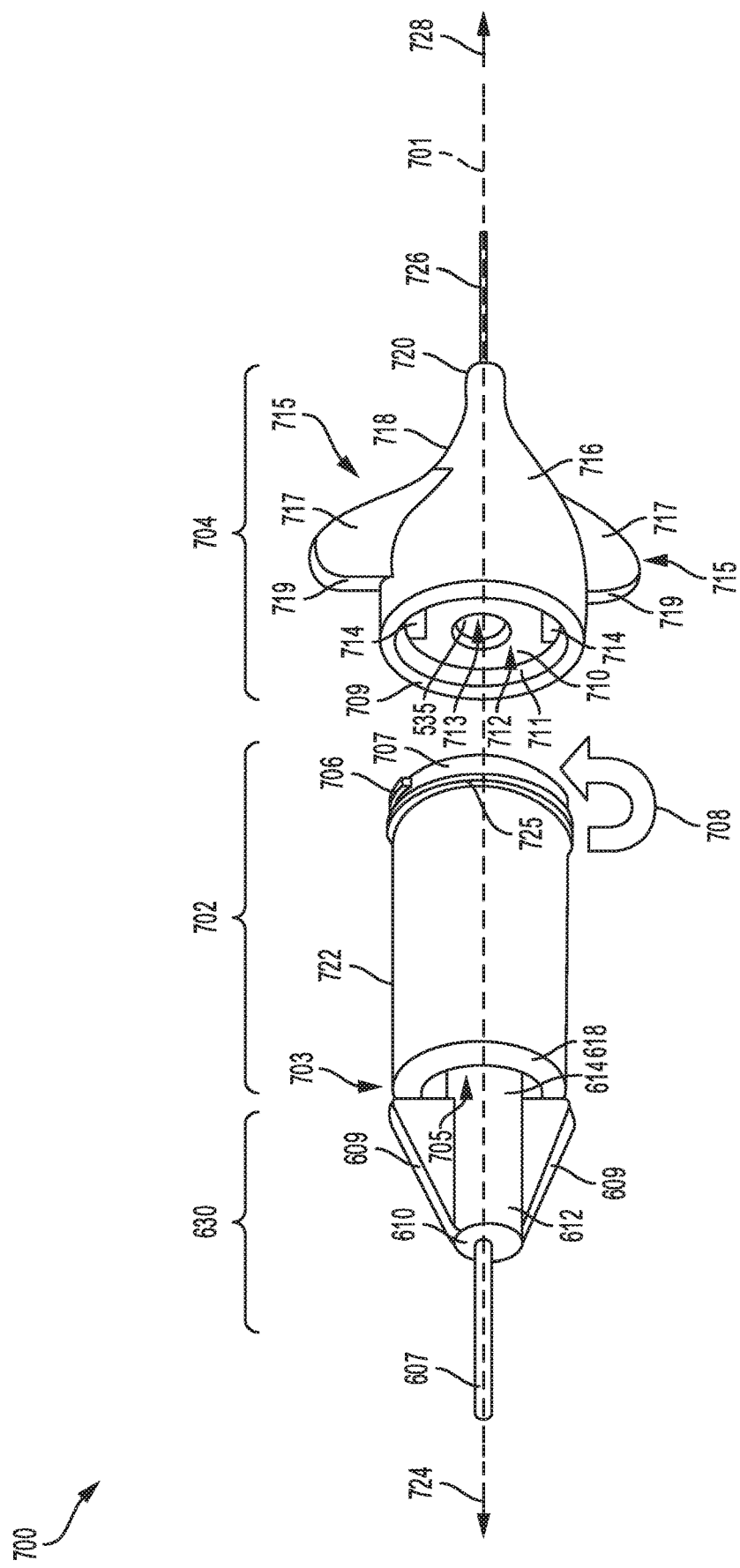
FIG. 7 shows a tenth embodiment of a catheter device, with a luer device mounted in a sterilization activation device that is coupleable to a sterilization port.

FIG. 7 shows a tenth embodiment of a catheter device comprising a luer device mounted to a sterilization activation unit that may be coupled to a sterilization port. A flexible tube, fluidly coupleable on a first end, to one or more access sites on the patient, may be connected on a second end, to the luer device coupleable to the activation device and the sterilization port. FIG. 8A shows an eleventh embodiment of a catheter device comprising a luer device mounted inside a sterilization activation device coupled to the sterilization port. A cross section through the activation device is depicted in FIG. 8B.

Alternative embodiments of the sterilization device having different shapes and sizes of the head unit, and various configurations of the luer port are disclosed in FIGS. 9A-M. Each of the sterilization devices shown in FIGS. 9A-M, may have various design of luer caps as depicted in FIGS. 9O-Q. Further embodiments of the sterilization device having different types of adhesive surfaces for attaching the sterilization device to the patient are illustrated in FIGS. 10A-10Z. The adhesive surfaces may be attached directly on a skin or clothing of the patient, for example. The adhesive surfaces may comprise a non-bacterial compound that minimizes patient infection and reduces skin irritation. Any of the sterilization devices disclosed in FIGS. 9A-M and FIGS. 10A-10Z, may be stacked together to provide sterilization systems including a plurality of stacked sterilization devices, as shown in FIGS. 11A-11H. By providing two or more sterilization devices within the sterilization system, disruptions due to malfunction of system components may be reduced while providing efficient means for sterilizing the luer port and access sites on the patient. An alternative embodiment of the catheter device configured with a luer port having multiple openings to receive multiple catheter lines coupled to the patient, is disclosed in FIGS. 12A-B.

Figure 13:
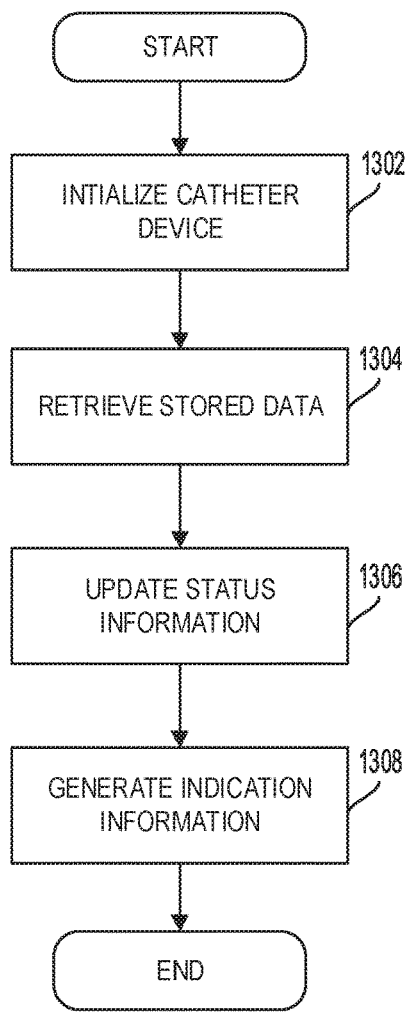
FIG. 13 shows an example method for operating the catheter device during a sterilization operation.
Figure 14:
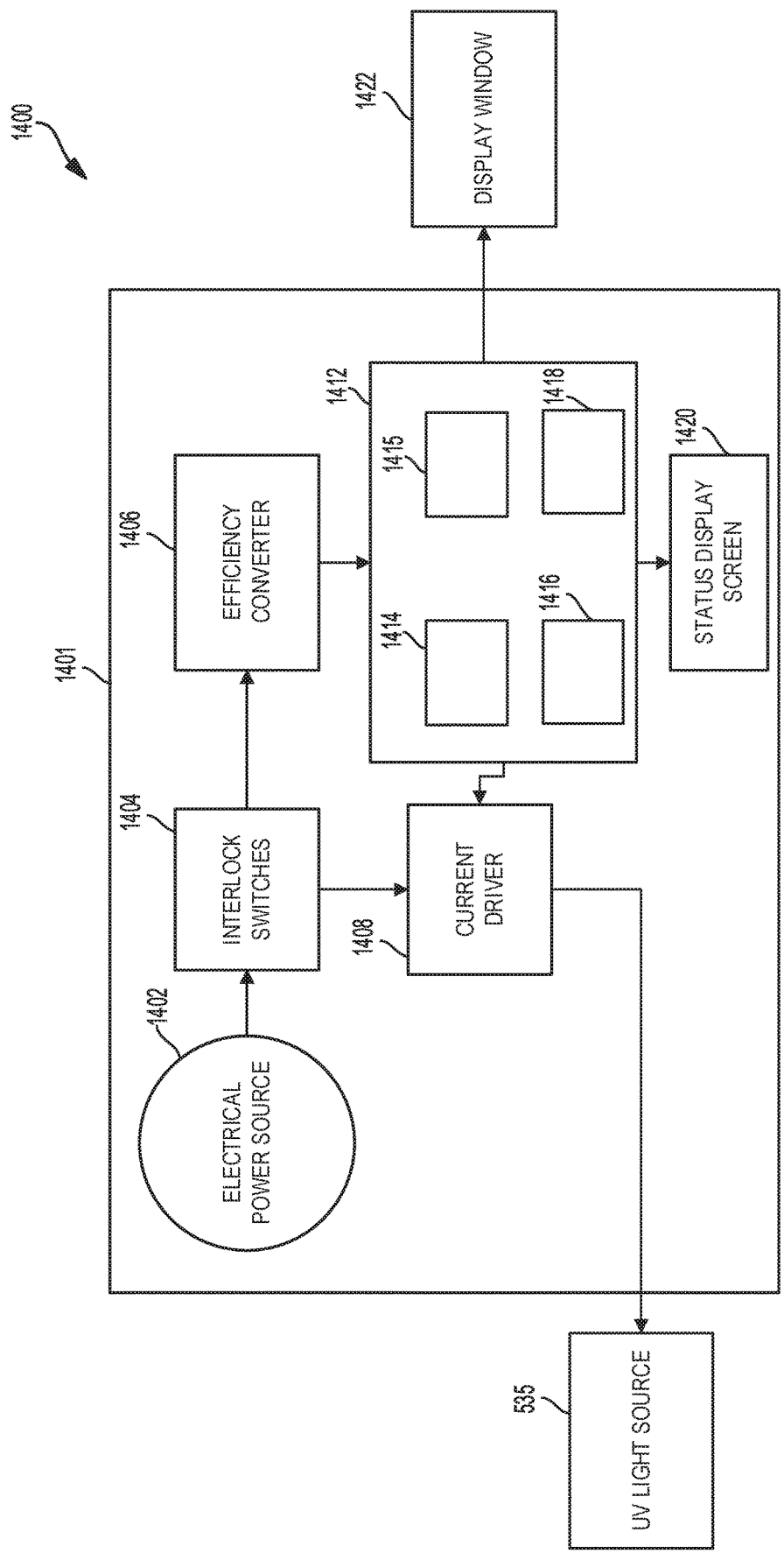
FIG. 14 shows an example electronic control system for controlling the catheter device.

The catheter devices or systems disclosed in FIGS. 1A-12B, may be operated using an example method disclosed in FIG. 13 using an electronic control system disclosed with reference to FIG. 14. The electronic control system may include an electrical power source connected to interlock switches coupled to a current driver. The interlock switches may be connected to an efficiency converter that is coupled to a microcontroller having a plurality of memory devices and a data bus. The UV light source mounted inside the luer port of the catheter device, shown in FIGS. 5-7, for example, may be activated by the current driver via the interlock switches or the microcontroller. The electronic control system may be mounted in a head unit of the catheter device, for example.

FIGS. 1A-12B show example configurations with relative positioning of the various components of a catheter device. If shown directly contacting each other, or directly coupled, then such elements may be referred to as directly contacting or directly coupled, respectively, at least in one example. Similarly, elements shown contiguous or adjacent to one another may be contiguous or adjacent to each other, respectively, at least in one example. As an example, components laying in face-sharing contact with each other may be referred to as in face-sharing contact. As another example, elements positioned apart from each other with only a space there-between and no other components may be referred to as such, in at least one example. As yet another example, elements shown above/below one another, at opposite sides to one another, or to the left/right of one another may be referred to as such, relative to one another. Further, as shown in the figures, a topmost element or point of element may be referred to as a "top" of the component and a bottommost element or point of the element may be referred to as a "bottom" of the component, in at least one example. As used herein, top/bottom, upper/lower, above/below, may be relative to a vertical axis of the figures and used to describe positioning of elements of the figures relative to one another. As such, elements shown above other elements are positioned vertically above the other elements, in one example. As yet another example, shapes of the elements depicted within the figures may be referred to as having those shapes (e.g., such as being circular, straight, planar, curved, rounded, chamfered, angled, or the like). Further, elements shown intersecting one another may be referred to as intersecting elements or intersecting one another, in at least one example. Further still, an element shown within another element or shown outside of another element may be referred as such, in one example.

Referring to FIG. 1A, a schematic depiction is shown of a first embodiment of a catheter device 100 for use in patient intravenous therapy. The catheter device 100 comprises catheter head unit 110 coupled via a connection line 132 to a luer port 130 with an ultra violet (UV) light source, and luer device 140 mounted axially to the luer port 130, and coupled to an extension component 150 with a catheter line 154. The catheter device 100 may be connected via the catheter line 154 to one or more access sites on a patient, as shown by the arrow 156.

As shown in FIG. 1A, the catheter head unit 110 includes a battery 120, mounted in a center region of the head unit 110. As an example, the battery 120 may comprise one or more rechargeable batteries mounted inside an interior region of the catheter head unit 110. The battery 120 may include one or more recesses and/or protrusions 121, for example. In one example, the recesses and/or protrusions 121 may connect to another catheter head unit, thereby connecting two or more head units together with respective side walls of each head unit in face-sharing contact and respective recesses mating with protrusions in a snap-fit connection to removeably couple two or more devices together as disclosed with reference to FIGS. 1B-C. As an example, three recesses/protrusions 121 may be provided, each being elongate and vertically positioned with respect to the top and bottom of the catheter device with vertical positioning disclosed herein merely to enable description of the components, as the device in use may be positioned in any orientation (e.g., the device may be upside down as it hangs on a patient's line). Of the three recesses/protrusions 121, a central line may be a longest, with two side lines symmetrically positioned, each being shorter in length. Any number of recesses and protrusions may be integrated. In one example, top surface 90 has protrusions 121, while bottom surface (not shown) has recesses (not shown but physically positioned symmetric and opposite the protrusions 121).

A socket 124, formed on a frontal portion of the head unit, allows the catheter device to be attached to the patient. As an example, an adhesive surface may be inserted through aperture 123 of the socket and wrapped around strap 91 of the socket to secure the catheter device 100 on the patient. An adhesive tab 128, mounted to side wall 126 of the catheter device 100, may attach to clothing or skin of the patient, thereby providing an additional means of securely attaching the catheter device to the patient.

The catheter head unit 110 may be connected to an upstream end 134 of the luer port 130 via the connection line 132 coupled to a distal element 129 formed on sidewall 122 of the head unit 110. As an example, the luer port 130 may be detachable from the catheter head unit 110 when the catheter device 100 is disassembled. In another example, the luer port 130 may be permanently attached to the catheter head unit 110. The luer port 130 contains a ultra-violet (UV) light source that produces UV radiation. As an example, the UV light source may be a UV light emitting diode (LED) that emits light with wavelengths in a range of 100 nm to 280 nm. When assembled, an upstream end 142 of the luer device 140 may be inserted axially into an opening formed in a distal end 136 of the luer port 130. Once inside the luer port 130, the luer device 140 may be turned anticlockwise, as shown by arrow 144, to secure the luer device 140 inside the luer port. For example, threads 147 wrapped around the upstream end 142 of the luer device 140, may be used to securely fastening the luer device 140 to corresponding threaded grooves inside the luer port.

An extension component 150 may be coupled to a distal portion 146 of the luer device 140 forming a tight coupling at joint interface 152. As an example, the extension component 150, may form part of the catheter port, once the luer device 140 is coupled to the luer port 130. The catheter line 154, attached to a distal end 153 of the extension component 150, may connect to one or more access sites on the patient. The catheter line 154 may be configured with an internal opening with a suitable diameter, to allow flow of UV radiation, fluids and other substances to the access sites on the patient. As an example, the access site on the patient may include blood vessels and other portions of the patient. The catheter device 100 may be externally mounted to the patient during intravenous therapy, for example. In this way, the catheter device 100 may comprise a first housing 110 having the power source 120 and a control circuit, a second housing 130 shaped to mate with the catheter 154 and having a first ultra-violet light source mounted therein, and a connection 132 for connecting the first housing 110 to the second housing 130. As an example, the connection 132 may be permanently affixed to one of the first and second housings of the catheter device 100.

When the catheter device 100 is assembled and attached to the patient, an electronic control system mounted in the catheter head unit 110 may be adjusted to activate the UV light source in the luer port 130 to emit UV radiation through an opening in the luer device 140. Subsequently, the UV radiation is transmitted through the luer device 140 and extension component 150, and travels through the catheter line 154 to disinfect access sites on the patient. For example, when the UV light source is activated, UV light of a predetermined wave length and lethal dosage, may be emitted in the luer port and transmitted through the catheter line 154 to disinfect interior passages of the catheter and access sites on the patient. In one example, the specific wave length of the UV light transmitted through the catheter line 154, acts as a germicidal irradiant that sterilizes interior areas of the catheter device 100 and access sites on the patient by destroying disease causing micro-organisms. In other examples, the specific wave length of the UV light emitted from the UV light source may range from 100 nm to 280 nm, comprising short wave radiation referred to as ultra-violet C (UV-C). Exposure to UV-C radiation may deactivate DNA of any microbes residing inside the catheter device 100 and patient access sites, reducing occurrences of patient infections.

The duration of exposure to UV radiation needed to sterilize the catheter device 100 and access sites on the patient may vary depending on various factors such as intensity of the light source, size of catheter device, and other factors. For example, the exposure duration to UV radiation during sterilization of the catheter device may range from 1 second to 10 minutes. The sterilization process may be conducted repeatedly if necessary, especially when the catheter device is operated for extended time duration.

In this way, the catheter device 100 may be used to sterilize interior areas of the device and multiple access sites on the patient to reduce the occurrence of patient infections. The sterilization method may be conducted automatically, providing an effective means of cleaning the catheter device while minimizing patient infections.

Referring to FIGS. 1B-C, a first view 102 and a second view 104, respectively of stacked catheter devices of the first embodiment are shown. The first view 102 shows a plan view of a plurality of catheter head units 110A-110C electrically connected together, each head unit 110A-C connected to each luer port 130A-130C via each connection line 132A-132C. The luer ports 130A-C may be positioned at different angles to allow for easy coupling with a luer device (such as luer device 140 shown in FIG. 1A). For example, a first head unit 110A may be positioned along a central axis 160, a second head unit 110B may be placed along axis 162, with axes 160 and 162 forming a first angle 166. Similarly, a third head unit 110C may be positioned along axis 164 to form a second angle 168 between axes 160 and 164. Attachment sockets 124 of each head unit 110 A-C may be positioned such that each unit 110A-C may be simultaneously attached to the patient. Each catheter head unit 110A-C may be stacked on top of each other, with battery 120A facing upwards as shown by arrow 96 in FIG. 1C.

As shown in FIG. 1C, a bottom portion 92 of the first head unit 110A is placed in face-sharing contact with a top portion 93 of the second head unit 110B, such that battery 120B touches the bottom portion 92 of the first head unit 110A. Similarly, a bottom portion 94 of the second head unit 110B is placed in face-sharing contact with a top portion 95 of the third head unit 110C, with battery 120C touching the bottom portion 94 of the second head unit 110A. As an example, two or more catheter head units may be electrically connected by stacking the head units together, to provide adequate electrical power to operate one or more catheter devices, while minimizing system disruptions due to malfunction of one or more system components. In this way, multiple catheter devices may be stacked together to provide a reliable source of electrical power needed to operate the catheter device while minimizing system failure during patient intravenous therapy.

Referring to FIGS. 1D-E, a first view 106 and second view 107, respectively of a second embodiment of a catheter device 105 is shown. The catheter device 105 includes a head unit 110 connected to a luer port 130 via a connection line 132. The head unit 110 includes a battery 120 centrally mounted in an interior region of the head unit. Although not shown, the head unit 110 may include an electronic control system for activating an ultra-violet (UV) light source mounted inside the luer port 130. The catheter device 105 may have an upstream end 170 and a downstream end 174.

The battery 120 may include one or more rechargeable batteries to power the catheter device 105. The battery 120 may be surrounded by elongated circular discs 115 and 116 disposed on either side of central axis 160. In addition, the battery 120 is surrounded by an oblate disc 114 having a curved section 148 formed at the upstream end 170 of the catheter device 105, and a geometric portion 112 formed at a middle portion 172. The elongated circular discs 115 may be connected to the geometric portion 112 and oblate disc 114 to form a continuous disc having a side wall 113. For example, each elongated circular disc may have a first curved section 125 that transitions to the oblate disc 114 at a second curved section 127. The edges of the geometric portion 112 are defined by side walls 119. As an example, the continuous disc may be formed on flat surface 118 having an elongated shape at the upstream end 170, and curved sections 117 at a middle portion 172. A socket 124, formed on the upstream end 170 of the head unit 110, includes a C-shaped strap 91 attached to the continuous disc at joint locations 165.

The luer port 130 includes a cylindrical body 131 having a distal end 136, and an opening 138 formed in an annular tube 149, the opening extending through a central interior region of the luer port 130. Further, the luer port 130 includes a plurality of fins 133 formed externally on the cylindrical body 131 of the luer port 130. As an example, each fin 133 may have an outer surface 139, including a side surface 141. The main opening 138 in the luer port 130 may have an adequate diameter 175 to receive a luer device, such as the luer device 140 disclosed with reference to FIG. 1A. In one example, the diameter 175 of the main opening 138 may be larger than the luer device, thereby allowing the luer device to fit inside the luer port 130. Closed surface 135 may define a closed end of the luer port 130. The luer port 130 may be coupled to the connection line 132 which transmits electrical power from the head unit 110 to activate the ultra-violet light source mounted inside the luer port 130. In this case, the UV light source may be activated by the electronic control system in the head unit 110 to emit UV radiation which is transmitted to the luer device coupled to the luer port 130, where the radiation is further transmitted to sterilize a catheter line coupled to the luer device and access sites on a patient. In this way, the catheter device 105 may be used to sterilize the catheter line while minimizing patient infections. Details on the luer device and catheter line are disclosed further below with reference to FIG. 2A.

Referring to FIGS. 1F-G, a first view 108 and second view 109, respectively of a third embodiment of a catheter device 111 is shown. The catheter device 111 includes a head unit 110 connected to a luer port 130 via a connection line 132. The head unit 110 includes a battery 120 centrally mounted in an interior region of the head unit. Although not shown, the head unit 110 may include an electronic control system for activating a ultra-violet light source mounted inside the luer port 130. The catheter device 111 may have an upstream end 170 and a downstream end 174.

As shown in FIGS. 1F-G, the battery 120 may be mounted on a circular disc 157 formed on a flat surface 118 of the catheter head unit 110. As an example, the battery 120 of catheter device 111 may comprise rechargeable batteries smaller in diameter compared to the battery of catheter device 105 disclosed with references to FIGS. 1D-E. In one example, the battery 120 may include one or more rechargeable batteries stacked together to power the catheter device 111. The battery 120 may be surrounded by circular discs 155 and 158 formed on flat surface 118, on either side of a central axis 160 of the catheter device 111. Further, a geometric portion 112 may be formed at a middle portion 172 adjacent to the circular discs 155-158, with curved edges 127 of the circular discs define a recessed slot 159. For example, the circular discs 155-158 may be connected to form a continuous disc, with the side wall 113 defining a boundary of the recessed slot 159. In one example, the side wall 113 may be include the first and second curved sections 125 and 127, wherein the first curved section 125 may be convexly shaped while the second curved section 127 may be concavely shaped. The continuous disc formed by circular discs 155-158 may be formed on flat surface 118 having an ovoid front shape and curved edge 117 forming a distal portion of the continuous disc.

A socket 124, formed on the upstream end 170 of the head unit 110, includes a D-shaped strap 91 attached to a front portion of flat surface 118. The luer port 130 coupled at the middle portion 172 of the head unit 110, receives electrical power via the connection 132 to activate the ultra-violet (UV) light source mounted inside the luer port 130. As an example, the UV light source may be activated by the electronic control system in the catheter head unit 110 to emit UV radiation that travels to a catheter line coupled on a first end to a luer device mounted inside the luer port, and coupled to access sites on the patient via a second end. In one example, the UV radiation may sterilize components of the catheter device 111, including the catheter line and access sites on the patient. The luer port 130 of the catheter device 111 has similar features as those of the access port of the catheter device 105, except for features on the cylindrical body 131. As shown in FIG. 1F, the cylindrical body 131 has no extending annular feature at its distal end. Also, a diameter 180 of an opening 138 in the luer port 130, may be smaller or larger than the diameter 175 of the access port of the catheter device 105.

In this way, the catheter device 111 may include a first housing 110 comprising the power source 120 and a control circuit; a second housing 130 shaped to mate with a catheter and having a first ultra-violet light source mounted therein, the first housing 110 wired to the second housing 130 to power the light source. In one example, the first housing 110 is substantially flat as compared to the second housing 130.

Referring to FIGS. 2A-2B, a fourth embodiment of a catheter device 200 and a fifth embodiment of a catheter device 202, respectively for use in patient intravenous therapy are shown. Each catheter device 200 and 202 includes a catheter head unit 210 having a plurality of batteries 208, and luer ports 130A-C coupled to the head unit 210 via connection lines 132A-C, respectively. Any of the luer ports 130A-C may be coupled to a luer device 140 connected to a catheter line 154 coupled to access sites on the patient, as shown by arrow 156. Further, each luer port 130A-C includes a pair of fins 133 formed on external surfaces of each luer port. Although not shown, the catheter head unit 210 of each catheter device 200 and 202 may include an electronic control system for activating a ultra-violet (UV) light source mounted inside each luer port 130A-C. The catheter head unit 210 of each catheter device 200 and 202 may also include a central opening 225 formed in a middle region of the head unit. For example, the central opening 225 may lead to reduced mass of the catheter head unit 210 without reducing structural integrity of the head unit.

As shown in FIG. 2A, the catheter head unit 210 of catheter device 200 may have a circular shape, although other shapes may be used. An attachment socket 124, having a strap 91 formed on a side portion of the catheter head unit 210, may have an aperture 123 for receiving an adhesive tape that may attached to the patient. An adhesive tab 128, formed on a perimeter of the catheter head unit 210, may be used as additional means of securing the catheter device 200 to the patient. The batteries 208 mounted to the catheter head unit 210, to provide electrical power to operate the catheter device 200, may be comprised of rechargeable batteries. As an example the rechargeable batteries may be recharged electrically when battery life reaches a level lower than 40-60 percent of battery capacity, thereby ensuring that the catheter device 200 has adequate electrical power to operate. Each luer port 130A-C connected to the catheter head unit 210 via each connection line 132A-C may receive electrical power from the batteries 208 to activate the UV light source mounted inside each port 130A-C. The luer device 140 may be coupled to any of the luer ports 130A-C by extending an upstream end 142 of the luer device 140, in a direction of arrow 144, and inserting the device into an opening 138 in the luer ports 130A-C. When inserted into any of the luer ports 130A-C, tapered section 143 of the luer device 140 may be disposed inside the opening 138 in each luer port 130A-C while cylindrical section 145 may extend out of the luer ports 130A-C.

When mounted inside any of the luer ports 130A-C, the luer device 140 may be secured in place, with the upstream end 142 of the luer device 140 disposed in the opening 138 of any of the luer ports 130A-C in a sterilization position. As an example, threads 147 may secure the luer device 140 in the sterilization position, within any of the luer ports 130A-C. In one example, each luer port 130A-C may be configured with mating threads (not shown) that closely match or are nominally larger than threads 147 on the luer device. In this case, the threads 147 on the luer device 140 may mate with the mating threads inside any of the luer ports 130A-C to secure the luer device in the sterilization position. In another example, a stop placed inside each luer port 130A-C may be provided to prevent insertion of the luer device 140 in any of the luer ports 130A-C beyond the sterilization position, thereby preventing the luer device 140 from being inserted too far into any of the luer ports 130A-C where it may damage the UV light source or other components. Once in the sterilization position, operation of the UV light source may commence such that UV light is directed at the central interior region of the luer device 140 for sterilization. Operation of the UV light source may require one or more switches to be activated as disclosed further with reference to FIG. 13. The switches may be engaged based on position of the luer device 140 within each luer port 130A-C, user-buttons, etc. In some examples, an indicator may provide a signal, such as a visible light signal to a user indicating operation of the UV light source. An upstream end 240 of the catheter line 154 may be coupled to a distal portion 146 of the luer device 140, and a downstream end 250 of the catheter line 154 may be connected to an access site on the patient, as shown by arrow 156.

As shown in FIG. 2B, the catheter head unit 210 of the catheter device 202 includes a plurality of batteries 208 formed on a flat surface 213. Each pair of batteries 208 are connected to each other via a bridge element 212. Each battery 208 has a circular side section 216 that extends to the flat surface 213. A compartment 218, formed at a downstream end 207 of the head unit 210, may be connected to a pair of batteries 208 via the bridge elements 212. A distal end 209 of the compartment 218 includes a plurality of apertures 214 with a recessed section 217 to receive a locking element 220, whose distal end 221 is coupled the connection line 132. A luer port assembly 204 shows details of the locking element 220 including a locking key 222. When inserted into the aperture 214, the locking element 220 snaps fit into the aperture 214, with the locking key 222 sliding into the recessed section 217, to connect the catheter head unit 210 to any of the luer ports 130A-B. Each luer port 130A-B has a cylindrical body 131 with an opening 138 formed at a distal end 136 and extending through a central interior region of each luer port 130A-B. The opening 138 is configured to receive a luer device (e.g., luer device 140 shown in FIG. 2A), which may be inserted in any of the luer ports 130A-B. As an example, the main opening 138 of each luer port 130A-B may have a diameter 230, larger than the luer device. In one example, the diameter 230 of the main opening 138 may range from 2.0 mm to 15 mm. In further examples, the main opening 138 in each luer port 130A-B may be configured with mating threads that closely match or are nominally larger than threads (e.g., threads 147 shown in FIG. 2A) on the luer device. In alternative examples, the main opening 138 of each luer port 130A-B may have no threads. The luer device mounted to any of the luer ports 130A-B, may be coupled to a catheter line connected to access sites of the patient. In this way, the UV light source in any of the luer ports 130A-B, may be activated by the electronic control system in the catheter head unit 210, to emit UV radiation which is transmitted through the luer device, thereby sterilizing the luer port and access sites on the patient.

In this way, the catheter device 202 may comprise, a first housing 210 comprising a power source 208 and a control circuit; a second housing 130A shaped to mate with a catheter and having a first ultra-violet light source mounted therein, the first housing 210 wired to the second housing 130A to power the light source. In one example, the first housing 210 is substantially flat as compared to the second housing 130A. In other examples, the catheter device 201 may include a third housing 130B shaped to mate with the catheter and having a second ultra-violet light source, the third housing 130B wired to the first housing and separate and freely-movable from the second housing 130B.

Referring to FIG. 3A, a sixth embodiment of a catheter device 300 having a luer port 310 and power device 320 including a luer device 305 is shown. The luer port 310 has an annular body 318 and circular annular elements 316 formed at a front end 309 and distal end 311 of the luer port. The annular body 318, configured with a bulging portion along a middle section, has a plurality of indentions 317 formed on the body. As an example, the indentations on the annular body 318 may provide a means of gripping the luer port 310 during assembly.

The luer port 310 includes a main opening 314 formed at the front end of 309 of the luer port to receive the luer device 305. A distal portion 146 of the luer device 305 may be extended in direction 308 and inserted into the main opening 314 of the luer port 310. As an example, the main opening 314 of the luer port 310 may have a diameter 375, larger than the luer device. In one example, the diameter 375 of the main opening 314 may range from 2.0 mm to 15 mm. The main opening 314 of the luer port may be configured with mating threads 313 that closely match or are nominally larger than threads 147 on the luer device. In alternative examples, the main opening 314 of the luer port may have no mating threads. When mounted inside the luer port 310, external surface 306 of the luer device 305 may be in face-sharing contact with the internal wall 312 of the luer port, with threads 147 mating with the mating threads 313 formed in the internal walls 312 of the luer port 310.

The power source 320 may be inserted into an open end 315 of the luer port 310, thereby activating a ultra-violet light source mounted inside the luer port. As an example, an upstream end 321 of the power device 320 may be extended along direction 319, and inserted into the open end 315 of the luer port 310. When mounted inside the luer port 310, luer keys 350 formed on a cylindrical disc 352, may mount in corresponding key slots in the luer port 310. In this way, the power source may be engaged in a lock position, thereby activating the UV light source which may emits UV radiation for sterilizing a catheter line coupled to the luer device 305, and access sites on a patient.

Serrated elements 323 formed on a front external surface at a top section 324 and bottom section 325 of the power device 320, provide ergonomic grip for handling the device. A utility clip 328, attached to the top section 324 at a downstream end of the power device 320, provides a means for attaching the assembled catheter device 300 to an operator's garments. For example, a distal end 332 of the utility clip 328 may be permanently fixed to a cylindrical body 360 of the power device, while an upstream end 330 may be unhinged to allow the clip to flex in direction 333 during attachment. A flash light 334 is attached to a downstream end 362 of the cylindrical body 360 to provide light, if desired. For example, the flash light may be operated by depressing a button 326, attached to a distal bottom portion 364 of the cylindrical body 360.

In this way, the catheter device 300 may comprise a handle having a power supply and a tamper-proof luer lock keyed to mate with the handle, the tamper-proof luer lock comprising a UV-C LED luer port 310 shaped to connect to the luer device 305 of the catheter device 300. As an example, the handle or power device 320 may include a visible light source 334, and further comprise a current connection at one end with a key 350 to mate with the luer lock. In other examples, the luer key 350 mates with the luer lock at an opposite end 315 from an opening 314 having the UV-C port shaped to connect to the catheter luer device 305.

Referring to FIGS. 3B-C, a first view 302 and second view 304, respectively of an alternative embodiment of a portable power source 370 is shown. The portable power source 370 may be coupled to a luer port, such as a luer port 310 in FIG. 3A. As shown, the portable power source 370 includes a body 380 and cord housing 340. The body 380 is comprised of an enlarged front section 327 which tapers into uniform cylinder 329 at a middle and rear sections. The luer keys 350, formed on a front end 354 of the body 380, have rod like ends that fit into corresponding slots in the luer port as disclosed further with reference to FIG. 4A. Serrated elements 323 formed on a front external surface of the body 380 provide ergonomic grip when inserting the power source 370 into the luer port during assembly, for example.

The body 380 has a curved element 346 formed at a downstream end 345 of the body 380. The curved element 346 has an aperture 347 formed centrally to receive a circular retractable cord 348 with an opening 349 larger than the aperture 347. The retractable cord 348 is disposed in an interior region of the cord housing 340, and extended through the aperture 347 formed on the curved element 346. The cord housing includes a first plate 342 and a second plate 344 mounted to a circular rim 341 with a side surface 343. As an example, the first and second plates of the cord housing 340 may be connected together by the side surface 343 to define the interior region of the housing 340 that contains the retractable cord 348. In one example, the retractable cord 348 may be extendable, thereby allowing the power source 370 to be handled easily.

Referring to FIGS. 4A-B, a seventh embodiment of a catheter device 400 and an eighth embodiment a catheter device 402, respectively are shown. Each catheter device 400 and 402 includes a first luer port 410 and a second luer port 420, respectively, and a power source 430. Each of the first and second luer ports 410 and 420 includes a cylindrical annular body 318 and circular annular elements 316 formed at a front end 309 and distal end 311 of each luer port. The cylindrical body 318 of each of the first and second luer ports 410 and 420 is configured with a smooth bulging portion along a middle section, which tapers towards the annular elements 316 at the front and distal ends of each luer port.

The front end 309 of each luer port 410 and 420 includes a main opening 314 to receive a luer device (such as luer device 140 shown in FIG. 3A). For example, the main opening 314 may have a diameter 435, larger than the luer device. In one example, the diameter 435 may be in a range of 3.0 mm to 15 mm. When mounted inside any of the luer ports 410 and 420, the luer device may be in face-sharing contact with an internal wall 312 of each luer port 410 and 420 as disclosed earlier with reference to FIG. 3A. The power source 430 includes an enlarged front section 405 which tapers into a uniform cylindrical section 408 at a middle portion, and a rounded distal portion 416. Recessed features 406 formed at the front section 405 of the power source 430, provide ergonomic grip for handling the power source 430 during assembly. The power source 430 may also include have a flat end 411 where a flash light may be mounted, as shown in FIG. 4B. A pair of luer keys 350, formed on disc element 352 fused to a front end 354 of the power source, have rod like elements that fit into corresponding key slots 415 in an open end 315 with an internal wall 412 forming a portion of any of the luer ports 410 and 420. As an example, an upstream end 321 of the power source 430 may be inserted into the open end 315 of the any of the luer ports 410 and 420, with the front end 354 of the power source 430 making face contact with the distal end 311 of the luer ports 410 and 420. When mounted inside the luer ports 410 and 420, the luer keys 350 of the power source 430 snap into corresponding key slots 415 in the open end 315 of each luer port.

Turning to FIG. 5, a schematic of alternative embodiment of a luer port 500 of a catheter device is shown. An upstream end 501 of the luer port 500 includes a main opening 511 to receive a luer device (e.g., luer device 140 shown in FIG. 1A), while a downstream end 531 is electrically coupled via a connection line 534 to a power source, such as battery 120 mounted to the catheter head unit 110 at FIG. 1A. The luer port 500 further includes an ultra-violet (UV) light source 535 mounted inside the luer port. A retractable cover 508 formed on a cylindrical body 506 of the luer port 500, provides a means of adjusting a side opening 537 for mounting and removing a luer device from the luer port. The retractable cover 508 and cylindrical body 506, may be tucked into an opening 509 formed inside a slotted annular body 510.

As shown in FIG. 5, the retractable cover 508 of the luer port 500 may be adjusted to open by retracting the retractable cover along direction 536, thereby adjusting the side opening 537 to an open position. Specifically, the retractable cover 508 may be adjusted to open by pulling closure dial 526 in the direction 536, thereby allowing a vertical arm 529 of the dial to slide along a slot 525. In one example, the closure dial 526 has vane elements 528 formed on a top portion of the dial to provide ergonomic grip. In another example, the closure dial 526 may be by pulling closure dial in a direction 538, thereby allowing the retractable cover 508 to close and seal the side opening 537.

A first grip element 512 and a second grip element 514 may be mounted inside the main opening 511. As an example, the first grip element 512 may be mounted to a first internal wall 560 while the second grip element 514 mounted to a second internal wall 562 of the luer port 500. The first and second internal wall may form a portion of an internal wall 533 of the luer port 500. Each of the first and second grip elements 512 and 514 may be in face-sharing contact with each first and second internal walls, respectively along contact interfaces 515 and 524. In another example, the first and second grip elements 512 and 514 are mounted inside the luer port with the flat surface 520 of each grip element facing the bottom internal wall while the corresponding surface of the second grip element faces the upper internal wall. In other examples, the first and second grip elements 512 and 514 may be comprised of silicone material or other suitable material such as thermoplastic elastomer (TPE) and other plastic-rubber derivative materials.

Each grip element 512 and 514 may include a cubic portion 565 having a planar surface 518, and a cylindrical portion 566 having a flat surface 520 and side planar surface 522. As an example, the first and second grip elements 512 and 514 may be space apart forming a first distance 545 and a second distance 550. Each of the first and second distances of the luer port 500 may be sized to receive the luer device. As an example, the first and second distances 550 may be larger than the diameter of the luer device. For example, the first distance 545 and the second distance 550 may both range from 3.0 mm to 15 mm. In other examples, the second distance 550 may range from 5.0 mm to 15 mm. In this way, the luer port 500 may be adequately sized to receive the luer device, with the retractable cover 508 adjusted to a close the side opening 537 once the luer device is mounted to the luer port. Details of mounting the luer device to the luer port 500 are disclosed further with reference to FIGS. 6A-C.

The UV light source 535 in the luer port 500, may be retained inside an aperture 519 formed inside an annular element 521 having a circular surface 517. The annular element 521 may be formed on a back internal wall 523 of the luer port. As an example, the UV light source 535 may be retained in the annular element 521, with the UV source partially embedded inside the aperture 519. The UV light source 535 may emit light with a wave length in a range of 100-280 nm, for example. In other examples, the UV light source may be axially mounted to direct UV radiation into an interior passage of the luer device, thereby allowing the UV radiation to travel through the luer device to sterilize interior areas of the catheter device and access sites on a patient.

Turning to FIGS. 6A-C, a first view 600, a second view 602 and a third view 604, respectively of an example procedure for installing a luer device 630 into a luer port 500 of a ninth embodiment of a catheter device 601 is shown. The first view 600 shows mounting the luer device 630 into the luer port 500. The luer device 630 comprises an extension component 605 coupled to an access port 606. A second view 602 shows the luer device 630 inside the luer port 500, with retractable cover 508 adjusted to a first position to reveal side opening 537. A third view 604 shows the luer device 630 mounted inside the luer port 500, with retractable cover 508 adjusted to a second position to close the side opening 537.

As shown in FIG. 6A, the luer device 630 may be mounted into the luer port 500 by inserting the luer device 630 through the side opening 537 of the luer port. Specifically, the luer device 630 may be mounted in a main opening 511 of the luer port 500, such that an upstream end 624 of the luer device 630 may be axially aligned with a ultra-violet (UV) light source 535 centrally mounted to an annular element 521 formed on a back internal wall 523 of the luer port 500. When mounted inside the luer port 500, a tapered portion 620 and a rear cylindrical portion 618 of the access port 606 of the luer device 630 may be disposed between a first and second grip elements 512 and 514 mounted to an internal wall 533 of the luer port 500, with vane features 622 touching the planar surfaces of the grip elements. The extension component 605 of the luer device 630 includes fins 609 formed on a cylindrical section 612. A distal portion 614 of the cylindrical section 612 may be mounted through an opening 616, while a downstream end 610 may be connected to a catheter line 607 coupled to the patient. For example, the catheter line 607 may be optically connected to the light source via an internal passage formed inside the luer device 630.

FIG. 6B shows the luer device 630 mounted in the interior opening of the luer port 500. In this case, the upstream end 624 of the luer device 630 may be touching a circular surface 517, such that a ultra-violet (UV) light source 535 is axially aligned with the internal opening in the luer body 630. The external surfaces of the luer device 630 to make face contact with the planar surfaces of grip elements 512 and 513, allowing the luer device 630 to be securely mounted inside the luer port 500. The catheter line 607, mounted to the extension component 605 of the luer device 630, may be fluidly coupled to the access sites on the patient, thereby allowing UV radiation emit from the UV light source to travel through the catheter line 607 to sterilize the catheter device 601 while minimizing patient infections.

The luer device 630 may be mounted inside the luer port 500, with the retracted cover 508 adjusted to the second position as shown in FIG. 6C. As an example, a closure dial 526 may be adjusted from the first position to the second position along direction 632, such that the retractable cover 508 closes, enclosing the luer device 630 inside the luer port 500. Once in the closed luer port position, the UV light source 535 mounted inside the luer port 500 may be activated by the electric power source, allowing the light source to emit ultra-violet radiation that is transmitted via the interior region of the luer device 630 to the catheter line 607. As an example, the catheter line 607 may be coupled to access sites on the patient, as shown by arrow 626. The transmitted UV light destroys micro-organisms attached to interior regions of the catheter line 607, providing an effective means of sterilizing the access port 606. In this way, the catheter device 601 provides an effective method for sterilizing the access port while minimizing occurrences of patient infections.

Referring to FIG. 7, a schematic view of a tenth embodiment of a catheter device 700 is shown. The catheter device 700 may include a luer device 630 mounted inside a sterilization activation device 702 coupled to a sterilization port 704 having fins 715 formed on an external surface 716. The luer device 630 may be coupled to a downstream end 703 of the activation device 702 by inserting a distal portion 614 of the luer device 630 into a main opening 705 formed inside a cylindrical body 722. The luer device 630 includes a pair of fins 609 formed on a cylindrical section 612, and a catheter line 607 routed through a downstream portion 610 of luer device 630 and fluidly connected to access sites on the patient, as shown by arrow 724. The catheter line 607 may extend through an internal region of the luer device 630 and connect to the main opening 705 in the activation device 702.

The activation device 702 may be coupled to the sterilization port 704 by inserting an upstream end 707 of the cylindrical body 730 into an opening 712 of the sterilization port 704. As an example, the upstream end 707 may be screwed into the sterilization port 704 by turning the activation device 702 along direction 708 to secure the cylindrical body 730 to the sterilization port 704. When coupled together, an external surface of the upstream end 707 of the activation device 702 may touch an internal wall 711 of the sterilization port 704 such that protrusions 714 formed on a back wall 710 of the sterilization port 704 lock into corresponding apertures in the activation device 702. As an example, a circular surface 709 of the sterilization port 704 may abut against circular ribs 725 formed on the upstream portion of the activation device 702, when the sterilization port 704 is securely attached to the activation device 702. Further, a ultra-violet (UV) light source 535 mounted in an aperture 713, formed in the back wall 710 of the sterilization port 704, may be axially aligned along central port axis 701. In one example, the UV light source 535 may be a ultra-violet (UV) source that produces light having a specific wave length in a range of 100-280 nm. In some examples, an indicator 706, formed on the external wall of the sterilization port 704, may provide a signal, such as a visible light signal to a user indicating operation of the catheter device and/or the UV light source 535.

The fins 715 formed on the external surface 716 of the sterilization port 704, have a vertical portion 717 and side portion 719 that provide ergonomic grip when mounting the sterilization port 704 to the activation device 702. Further, the sterilization port 704 includes a tapered section 718 that extends to an upstream end 720 coupled to connection line 726 coupled to a power source (placed upstream of the port, as shown by arrow 728) to operate the catheter device 700.

As an example, the power source may include a plurality of rechargeable batteries to provide adequate power to operate the catheter device 700.

In this way, the catheter device 700 may comprise the luer device 630 mounted to the activation device 702 coupled to the sterilization port 704 having the UV light source 535. By coupling the activation device 702 to the sterilization port 704, the UV light source 535 may be activated to emit UV radiation to disinfect the catheter device 700 and access sites on the patient.

Turning to FIGS. 8A-B, a schematic view of an eleventh embodiment of a catheter device 800 is shown. The catheter device 800 may include a luer device 630 mounted to an activation device 804 coupled to a sterilization port 704 along a central port axis 820. The sterilization port 704 may include fins 715 formed on an external surface 716 of the port. FIG. 8B shows a cross section 801 of the activation device 804. The luer device 630 and the sterilization port 704 have similar components as those disclosed with reference to the luer device and port of catheter device 700 shown in FIG. 7, and will not be disclosed again herein.

The activation device 804 includes a top section 802 and a bottom section 803 having a cylindrical body 824. The top section 802 has circular rings 808 and grooves 811 formed on an external surface of the top section. The bottom section 803 may be coupled to the top section 802 by inserting a top portion of the bottom section 803 into a bottom-most groove formed on the top section 802, for example. In another example, the top and bottom sections of the activation device 804 may be connected together using a suitable adhesive. Alternatively, the bottom section 803 may be coupled to the top section 802 by inserting a top protruding element 813 (formed as part of wall section 815) on the bottom section 803 into a bottom-most groove formed on the top section 802, as shown in FIG. 8B. For example, the top section 802 may be mounted inside cylindrical body 824 such that a distal end 814 extends into a main opening 816 formed inside the cylindrical body 824. As an example, internal opening 812 formed inside the top section 802 may be axially aligned with the main opening 816 when the top section 802 is mounted inside the cylindrical body 824. The top section 802 may include a slot 805 to receive a bottom portion of the luer device 630.

As shown in FIG. 8A, the luer device 630 may be coupled to an upstream end 809 of the activation device 804 by inserting a distal portion 614 of the luer device 630 into a main opening 705 formed inside the top section 802. The luer device 630 includes an upstream end 834 coupled to a catheter line 822 that may be fluidly connected to a patient access site as shown by arrow 830. The catheter line 822 may extend through an internal region of the luer device and connect to the main opening 705 in the activation device 804.

The bottom section 803 of activation device 804 may be coupled to the sterilization port 704 by inserting distal end 818 of the cylindrical body 824 into an opening 712 of the sterilization port 704. For example, the distal end 818 of the cylindrical body 824 may be screwed into the sterilization port 704 by turning the activation device 804 along direction 826 to secure the bottom section 803 to the sterilization port 704. When coupled together, the distal end 818 of the activation device 804 may touch an internal wall 711 of the sterilization port 704, such that protrusions 714 formed on a back wall 710 of the port lock into corresponding apertures in the activation device 804. As shown in FIG. 8B, the bottom section 803 of the activation device 804 may be coupled to the sterilization port such that the circular surface 709 of the sterilization port makes contact with the distal end 818 of the activation device 804.

The sterilization port 704 may include a ultra-violet (UV) light source 535 mounted in an aperture 713 formed in the back wall 710 of the port, may be axially aligned along central port axis 820. As an example, the UV light source 535 may be a UV LED device that produces light having a specific wave length in a range of 100-280 nm. Further, the sterilization port 704 may have a connection line 832 coupled to a power source to operate the catheter device 800. As an example, the power source may include a plurality of rechargeable batteries or other suitable electrical power source to operate the catheter device 800. In this way, the catheter device 800 may be operated using rechargeable power. By coupling the activation device 804 to the sterilization port 702, the UV light source mounted inside the port may be activated to emit UV radiation to sterilize the catheter device 800 to minimize patient infections.

Referring to FIGS. 9A-9B, a schematic depiction showing a twelfth embodiment of a sterilization device 900 and a thirteenth embodiment of a sterilization device 901, respectively is shown. Each of the sterilization devices 900 and 901 are configured with a head unit 940 having a plurality of batteries 120, and connected to a luer port 130 via a connection line 132. The head unit 940 may be a square shape unit containing a housing 922 and the batteries 120. Each sterilization device 900 and 901 may be coupled to a luer device (e.g., luer device 140 shown in FIG. 2A) connected to a catheter line, such as catheter line 154 shown in FIG. 2A.

As shown in FIGS. 9A-B, each head unit 940 of each of sterilization device 900 and 901 includes multiple batteries 120 mounted on either side of the housing 922, and an outer plate 924. As an example, the batteries 120 and the housing 922 may be mounted to the outer plate 924 during manufacture of the catheter devices 900 and 901. In one example, the batteries 120 may be rechargeable batteries that may be charged once the batteries reach a threshold depletion level below a battery capacity. As an example, the batteries 120 may be recharged when the battery level reaches a level lower than 40-50 percent of the battery capacity.

In another example, the batteries 120 mounted on each head unit 940, may comprise four or more batteries to provide adequate electrical power to operate each sterilization device 900 and 901. The housing 922 may contain an electronic control system for controlling each sterilization device 900 and 901, as disclosed further with reference to FIG. 14. Although not shown in FIG. 9A, sterilization device 900 may include an adhesive surface that attaches to the patient. The sterilization device 901 may be mounted to the patient using adhesive surface 928 attached to the head unit 940, as shown in FIG. 9B. As an example, the adhesive surface 928 may be a sticky surface that attaches to clothing or skin of the patient. In other examples, the adhesive surface 928 may be mounted underneath the outer plate 924 of the head unit 940, to provide a larger surface area for attachment.

The connection line 132 mounted through a side wall 925 of the housing 922 of each sterilization device 901 and 902, may be connected to the luer port 130. As an example, the connection line 132 may include a plurality of cables for transmitting electrical power and instructions from each head unit 940 of the sterilization devices 900 and 901 to each luer port 130 and other components of each sterilization device 900 and 901. As an example, the connection line 132 may be a flexible line containing one or more secondary cables for transmitting electrical power from the batteries 120, and transmitting instructions to the luer port 130 and other components of each sterilization device 900 and 901. In another example, the connection line 132 may be a rigid tube containing multiple cables for transmitting electrical power and instructions to the luer port 130 and other components of each sterilization device 900 and 901. The luer port 130 includes an opening 930 formed at a distal end 926 of the luer port 130 of each sterilization device 900 and 901. As an example, the opening 930 may have a suitable diameter to receive the luer device (such as luer device 140 shown in FIG. 1A) that may be connected to one or more access sites on the patient. In one example, an ultra-violet (UV) light source (e.g., UV light source 535 shown in FIG. 7) may be mounted inside the opening 930 to produce UV-C radiation to sterilize the catheter access port.

Referring to FIGS. 9C-9D, a schematic depiction showing a fourteenth embodiment of a sterilization device 902 and a fifteenth embodiment of a sterilization device 903, respectively is shown. Each of the sterilization devices 902 and 903 are configured with a head unit 950 having a plurality of batteries 120, and connected to a luer port 130 via a connection line 132. Each head unit 950 of the sterilization devices 902 and 903 may be a linearly shaped unit containing the batteries 120, with a housing 922 mounted at a downstream end of each sterilization device 902 and 903.

As shown in FIGS. 9C-D, the head unit 950 in each sterilization device 902 and 903 includes multiple batteries 120 mounted upstream of the housing 922, and an outer plate 924. The batteries 120 and the housing 922 may be mounted to the outer plate 924 during assembly of each sterilization device 902 and 903, for example. The batteries 120 may be rechargeable batteries that are charged once the batteries reach a threshold level below a battery capacity. As an example, the batteries 120 may be recharged when the battery level reaches a level lower than 40 percent of the battery capacity. In another example, the batteries 120 mounted on the head unit 950 on each sterilization device 902 and 903, may comprise four or more batteries to provide adequate electrical power to operate each sterilization device. The housing 922 may contain an electronic control system for controlling each sterilization device 902 and 903 as disclosed further with reference to FIG. 14. Although not shown in FIG. 9C, sterilization device 902 may include an adhesive surface that attaches to the patient. The sterilization device 903 may be mounted to the patient using an adhesive surface 928 attached to the head unit 950, shown in FIG. 9D. As an example, the adhesive surface 928 may be a sticky surface that attaches to a clothing or skin of the patient. In other examples, the adhesive surface 928 may be mounted underneath the outer plate 924 of each head unit 950, to provide a larger attachment surface.

The housing 922 on each sterilization device 902 and 903, may be connected to the luer port 130 via the connection line 132, routed through a side wall 925 of each housing 922. As an example, the connection line 132 may include a plurality of cables for transmitting electrical power from the batteries 120, and instructions to the luer port 130 and other components of each sterilization device. In one example, the connection line 132 may be a flexible or rigid line containing one or more secondary cables for transmitting electrical power and instructions to the luer port 130 and other catheter components. The luer port 130 on each sterilization device 902 and 903 includes an opening 930. The opening 930 may be formed at a distal end 926 of each sterilization device 902 and 903. For example, the opening 930 may have a suitable diameter to receive a luer device (such as luer device 140 shown in FIG. 2A) that may be connected to one or more access sites on a patient. In one example, a ultra-violet (UV) light source (e.g., UV light source 535 shown in FIG. 7) may be mounted inside the opening 930 to produce UV-C radiation to sterilize the catheter access port.

Referring to FIGS. 9E-9F, a schematic depiction showing a sixteenth embodiment of a sterilization device 904 and a seventeenth embodiment of a sterilization device 905, respectively is shown. Each sterilization device 904 and 905 may be configured with a head unit 960 having a plurality of batteries 120, and connected to a luer port 130. The head unit 960 may be a linearly shaped unit containing the batteries 120, with a housing 922 mounted adjacent the luer port 130, at a downstream end of each sterilization device.

As shown in FIGS. 9E-9F, the head unit 960 in each of the sterilization devices 904 and 905 include multiple batteries 120 mounted upstream of the housing 922. The batteries 120 and the housing 922 may be mounted to an outer plate 924 during device assembly, for example. The batteries 120 may be rechargeable batteries that may be charged once the batteries reach a threshold level below a battery capacity. As an example, the batteries 120 may be recharged when the battery level reaches a level lower than 40 percent of the battery capacity. In another example, the batteries 120 mounted on the head unit 960, may comprise four or more batteries to provide adequate electrical power to operate the sterilization devices 904 and 905. The housing 922 of each sterilization device 904 and 905 may contain an electronic control system for controlling the sterilization device as disclosed further with reference to FIG. 14. Although not shown in FIG. 9E, sterilization device 904 may have an adhesive surface that attaches to the patient. The sterilization device 905 may be secured to the patient using adhesive surface 928 attached to the head unit 960, shown in FIG. 9F. As an example, the adhesive surface 928 may be a sticky surface that attaches to a clothing or skin of the patient. In other examples, the adhesive surface 928 may be attached underneath the outer plate 924 of the head unit 960, to provide a larger attachment surface area.

The housing 922 on each sterilization device 904 and 905, positioned adjacent to the luer port 130, may include the electronic system that controls transmission of electrical power, and instructions to the luer port 130 and other components of each sterilization device 904 and 905. The luer port 130 of each sterilization device 904 and 905 includes an opening 930, which has a suitable diameter to receive a luer device (such as luer device 140 shown in FIG. 1A) that may couple to a catheter line coupled to the patient. In one example, a ultra-violet (UV) light source (e.g., UV light source 535 shown in FIG. 7) may be mounted inside the opening 930 to produce UV-C radiation which may be transmitted through the catheter access port. In this way, each sterilization device 904 and 905 may be activated to sterilize the catheter access port using UV radiation emitted from the UV light source.

Referring to FIGS. 9G-9H, a schematic depiction showing an eighteenth embodiment of a sterilization device 906 and a nineteenth embodiment of a sterilization device 907, respectively is shown. The sterilization devices 906 and 907 are configured with head units 970 and 980, respectively. Each heat unit 970 and 980 has a plurality of batteries 120, and is connected to a luer port 130 via a connection line 132. The head unit 970 may be a linearly shaped unit containing the batteries (not shown) and other components of the sterilization device 906. Similarly, head unit 980 is a linearly shaped unit with an interior region for mounting a plurality of batteries 120 to the of the sterilization device 907. As an example, each head unit 970 and 980 has an upstream end 932 and a downstream end 934.

The luer port 130 of each of the sterilization device 906 and 907 may be connected to each head unit 970 and 980 by routing the connection line 132 through a side wall 925 of each sterilization device 906 and 907. As an example, the connection line 132 may include a plurality of cables for transmitting electrical power from the batteries in each head unit 970 and 980, and instructions to the luer port 130 and other components of each sterilization device 906 and 907. In one example, the connection line 132 may be a flexible or a non-flexible line containing one or more secondary cables for transmitting electrical power, and instructions to the luer port 130 and other components of each sterilization device 906 and 907. The luer port 130 of each sterilization device 906 and 907 includes an opening 930 formed on the distal end 926 of the luer port 130. For example, the opening 930 on each sterilization device 906 and 907 may have a suitable diameter to receive a luer device (such as luer device 140 shown in FIG. 1A) that may be connected to a catheter line coupled to one or more access sites on a patient. In one example, an ultra-violet (UV) light source (e.g., UV light source 535 shown in FIG. 7) may be mounted inside the opening 930 to produce UV-C radiation to sterilize the catheter access port.

Referring to FIGS. 9I-J, a schematic depiction showing a twentieth embodiment of a sterilization device 908 and a twenty first embodiment of a sterilization device 909, respectively is shown. The sterilization devices 908 and 909 are configured with head units 984 and 985, respectively. Each head unit 984 and 985, comprises an upstream end 932 and a downstream end 934. Although not shown, head unit 984 of the sterilization device 908 has a plurality of batteries mounted in an interior region within the head unit 984. Similarly, head unit 985 of the sterilization device 909 has a plurality of batteries 120, and is connected to a luer port 130. Each of the head units 984 and 985 may be linearly shaped units containing four or more batteries, with the luer port 130 mounted at the downstream end 934 of each sterilization device 908 and 909.

Each sterilization device 908 and 909 may include an electronic system that controls transmission of electrical power from the batteries inside each head unit 984 and 985, and transmission of instructions to the luer port 130 and other components of each sterilization device 907 and 908. The luer port 130 of each sterilization device 908 and 909, includes an opening 930, which has a suitable diameter to receive a luer device (such as luer device 140 shown in FIG. 1A) that may be couple to a patient. In one example, a ultra-violet (UV) light source (e.g., UV light source 535 shown in FIG. 7) may be mounted inside the opening 930 to produce UV-C radiation which may be transmitted to access sites on the patient via a catheter line coupled to the luer device of each sterilization device 907 and 908. In this way, each sterilization device 907 and 908 may be sterilized using radiation from the UV light source, thereby reducing occurrence of patient infections.

Referring to FIGS. 9K-9L, a schematic depiction showing a first alternative embodiment of a sterilization device 910 and a second alternative embodiment of a sterilization device 911, respectively is disclosed. Each of the sterilization devices 910 and 911 are configured with head units 984 and 985, respectively. Each head unit 984 and 985, comprises an upstream end 932 and a downstream end 934. Although not shown, head unit 984 has a plurality of batteries mounted in an interior region of the sterilization device 910. Similarly, head unit 985 of the sterilization device 911 has a plurality of batteries 120, and a luer port 130. Each of the head units 984 and 985 may be linearly shaped units containing five or more batteries, with the luer port 130 mounted adjacent to the downstream end 934 of each sterilization device 910 and 911. The features and operation details of sterilization devices 910 and 911 are similar to those of sterilization devices 908 and 909 disclosed with reference to FIGS. 9I-9J.

Referring to FIGS. 9M-9N, a schematic depiction showing a twenty second embodiment of a sterilization device 912 and a twenty third embodiment of a sterilization device 913, respectively is shown. Each of the sterilization devices 912 and 913 are configured with a head unit 990 having a plurality of batteries 120, and connected to a luer port 130 via a connection line 132. The head unit 990 may be a pentagon shape unit containing five or more batteries 120 and a housing 922.

As shown in FIGS. 9M-9N, the head unit 990 in each of the sterilization devices 912 and 913 includes multiple batteries 120 mounted around the housing 922. The batteries 120 and the housing 922 of each sterilization device 912 and 913 may be mounted to an outer plate 924 during manufacture. The batteries 120 may be rechargeable batteries that may be charged once the batteries reach a threshold level below a battery capacity. As an example, the batteries 120 may be recharged when a battery level reaches a level lower than 40 percent of the battery capacity. In another example, the batteries 120 mounted on the head unit 990, may comprise five or more batteries to provide adequate electrical power to operate each sterilization device 912 and 913. The housing 922 may contain an electronic control system for controlling each sterilization device 912 and 913, as disclosed further below with reference to FIG. 14. The sterilization device 912 may be secured to the patient using an adhesive surface 928 attached to the head unit 990, shown in FIG. 9M. As an example, the adhesive surface 928 may be a sticky surface that attaches to a clothing or skin of the patient. In other examples, the adhesive surface 928 may be attached underneath the outer plate 924 of the head unit 990, to provide a larger attachment surface area.

The connection line 132 routed through a side wall 925 of the head unit 990 of each sterilization device 912 and 913, may include a plurality of cables for transmitting electrical power and instructions from the head unit 990 to the luer port 130 and other components of each sterilization device 912 and 913. In one example, the connection line 132 may be a flexible or a rigid line containing multiple secondary cables for transmitting electrical power, and instructions to the luer port 130 and other components of the sterilization devices 912 and 913. The luer port 130 of each sterilization device 912 and 913 may include an opening 930 formed on a distal end 926 of the luer port 130. For example, the opening 930 may have a suitable diameter to receive a luer device (such as luer device 140 shown in FIG. 1A) that may be connected a sterilization line couple to one or more access sites on the patient. In one example, a ultra-violet (UV) light source (e.g., UV light source 535 shown in FIG. 7) may be mounted inside the opening 930 to produce UV-C radiation to sterilize the catheter access port.

Referring to FIGS. 9O-9Q, a schematic depiction showing various embodiments of a luer port of a sterilization device (such as sterilization device 901 shown in FIG. 9B) is shown. A first embodiment 914 of a luer port 991 includes an end cap 938 strapped to a distal end 926 of an annular tube 927 via a flexible strap 936. A second embodiment 916 of a luer port 993 includes a depressable portion 929 at a downstream end 931 of an annular tube 937 of the luer port 993. A third embodiment 918 of a luer port 995 includes an annular tube 947 with a closed end 939.

The annular tubes 927-947 of the luer ports 991-993, respectively may be configured with a tapered portion 923 which couples to a connection line 132. As an example, the connection line 132 in each luer port 991-993 may be coupled to a head unit (e.g., head unit 940 shown in FIG. 9B) of the sterilization device, positioned in direction shown by arrow 915. As shown in FIG. 9O, the luer port 991 is adjusted to a closed position, with the end cap 938 sealing the distal end 926 of the luer port 991. When adjusted to the closed luer port position, a ultra-violet (UV) light source mounted inside an opening (e.g., opening 930 shown in FIG. 9B) in the luer port 991, may be protected from external elements while minimizing accident leakage of UV radiation to the external environment. The luer port 991 may be opened by adjusting the end cap 938 in a direction 933, thereby allowing the flexible strap 936 to flex outward, as shown by arrow 935. When the luer port 991 is adjusted to the open position, a luer device (e.g., luer device 140 shown in FIG. 1A) may be inserted into the opening in the luer port 991 to operate the sterilization device.

As shown in FIG. 9P, the luer port 993 is depicted with the depressable portion 929 in a closed position. When in the closed luer port position, the UV light source mounted inside an opening the luer port 993 may be protected from external elements while minimizing accident leakage of UV radiation to the external environment. The depressable portion 929 may be adjusted by squeezing ends 941 of the depressed portion in a direction 943 to open the luer port 993. When adjusted to the open luer port position, the luer device may be mounted into an opening in the luer port 993 during catheter operation. Although shown in a closed position, the luer port 995 may be adjusted to open. As an example, the closed end 939 may be configured with a plurality of slits (not shown) that allow a luer device to be inserted into the luer port. The closed end 939 may act as a light occluding cover that protects an interior region of the luer port from external elements. In this way, each luer ports 991-995 may be configured with a mechanism for opening and closing each luer port during operation of the sterilization device. By closing the luer ports 991-995, the UV light source mounted inside each luer port 991-995 may be protected from external elements while minimizing accident leakage of UV radiation to the external environment.

Referring to FIGS. 10A-10B, a schematic depiction showing a twenty fourth embodiment of a sterilization device 1000 and a twenty fifth embodiment of a sterilization device 1002, respectively is shown. Each of the sterilization devices 1000 and 1002 are configured with head units 970 and 980, respectively. Each head unit 970 and 980, comprises an upstream end 932 and a downstream end 934. Although not shown, head unit 970 has a plurality of batteries mounted in an interior region within the head unit 970 of the sterilization device 1000. Similarly, head unit 980 has a plurality of batteries 120 mounted to the upstream end 932 of the sterilization device 1002. Each of the head units 970 and 980 may be linearly shaped units containing multiple batteries, and coupled to a luer port 130 via connection line 132 routed through a sidewall 925 of each sterilization device 1000 and 1002. The luer port 130 in each sterilization device 1000 and 1002 may include an opening 930 formed at a distal end 926 of the luer port.

The sterilization device 1000 may be attached to a patient using an adhesive surface 942 mounted to a first surface 944 of the head unit 990, as shown in FIG. 10A. As an example, the adhesive surface 942 may be mounted to the head unit such that the adhesive surface forms a first overlapping portion 1012 and a second overlapping portion 1014, the first and second overlapping portions separated by a central port axis 1015. In one example, the adhesive surface 942 may be a sticky surface that attaches to a skin of the patient. In other examples, the adhesive surface 942 may be coated with non-bacterial compounds such as silver (and variations thereof), chlorhexidine, antibiotic compounds, antimicrobial peptide etc., to minimize skin infection and irritation. Although not shown in FIG. 10B, the head unit 980 may include an adhesive surface (similar to adhesive surface 942 shown in FIG. 10A) that attaches to the patient's skin. Alternatively, medical tape may be used to attach the sterilization device 1002 to the patient. As an example, the medical tape may be wrapped around the head unit 980 of the sterilization device 1002, and securely attached to the patient's skin.

Referring to FIGS. 10C-10D, a schematic depiction showing a twenty sixth embodiment of a sterilization device 1003 and a twenty seventh embodiment of a sterilization device 1004, respectively is shown. The sterilization devices 1003 and 1004 are configured with head units 984 and 985, respectively. Each head unit 984 and 985, comprises an upstream end 932 and a downstream end 934. Although not shown, head unit 984 of the sterilization device 1003 includes a plurality of batteries mounted in an interior region of the head unit 984. Similarly, head unit 985 includes a plurality of batteries 120 mounted to the upstream end 932 of the sterilization device 1002. Each of the head units 984 and 985 may be linearly shaped units containing multiple batteries, and connected to a luer port 130. The luer port 130 in each sterilization device 1003 and 1004, may include an opening 930 formed at a distal end 926 of the luer port.

The sterilization device 1003 may be attached to a patient using an adhesive surface 942 mounted to a first surface 944 of the head unit 990, as shown in FIG. 10C. As an example, the adhesive surface 942 may be mounted to the head unit 984 such that the adhesive surface 942 forms a first overlapping portion 1012 and a second overlapping portion 1014, the first and second overlapping portions separated by a central port axis 1015. In one example, the adhesive surface 942 may be a sticky surface that attaches to a skin of the patient. In other examples, the adhesive surface 942 may be coated with non-bacterial compounds such as silver (and variations thereof), chlorhexidine, antibiotic compounds, antimicrobial peptide etc., to minimize skin infection and irritation. Similarly, although not shown in FIG. 10D, the head unit 985 may include an adhesive surface (such as adhesive surface 942 shown in FIG. 10C) which attaches to the patient's skin. In an alternative example, medical tape may be used to attach the sterilization device 1004 to the patient. As an example, the medical tape may be wrapped around the head unit 985 to securely attach the sterilization device 1004 to the patient.

Referring to FIGS. 10E-10F, a schematic depiction showing a twenty eighth embodiment of a sterilization device 1006 and a twenty ninth embodiment of a sterilization device 1008, respectively is shown. The sterilization devices 1006 and 1008 are configured with head units 980 and 970, respectively. Each head unit 970 and 980, comprises an upstream end 932 and a downstream end 934. The head unit 980 has a plurality of stacked batteries 120 mounted to the upstream end 932 of the sterilization device 1006. Although not shown, head unit 970 has a plurality of stacked batteries mounted in an interior region within the head unit 970 of the sterilization device 1008. As an example, the stacked batteries in each sterilization device 1006 and 1008, may comprises four or more rechargeable batteries stacked together to provide adequate electrical power to operate each sterilization device.

As shown in FIGS. 10E-F, each of the head units 970 and 980 may be linearly shaped units coupled to a luer port 130 via a connection line 132 routed through a sidewall 925 of each sterilization device 1006 and 1008. The luer port 130 in each sterilization device 1006 and 1008, may include an opening 930 formed at a distal end 926 of each sterilization device 1006 and 1008, to receive a luer device (e.g., luer device 140 shown in FIG. 1A). Each sterilization device 1006 and 1008, may include an adhesive surface 942, which attaches to a patient's skin, for example. The adhesive surface 942 may be coated with a non-bacterial compound that minimizes skin infection and reduces patient discomfort.

The sterilization device 1008 may include a catheter channel 965 to receive a catheter tube 917, as shown in FIG. 10F. As an example, the catheter channel 965 may be formed between a first plate 962 and a second plate 964, the first and second plate mounted in an interior region 963 in the head unit 970. The catheter channel 965 may have a height 967 larger than a diameter of the catheter tube 917. For example, the diameter of the catheter tube 917 may range from 2.0 to 7.0 mm, while the height 967 of the catheter channel 965 may range from 1.0 to 15 mm. In this way, the sterilization device 1008 may be configured with the catheter channel 965 adequately sized to receive the catheter tube 917 that may be coupled to one or more access sites on the patient.

Referring to FIG. 10G, a schematic depiction showing a thirtieth embodiment of a sterilization device 1009 configured with a head unit 994 having a first head portion 1019 and a second head portion 1021, and a channel 965 formed in between the first and second head portions. The sterilization device 1009 also includes a connection line 132 coupled to the head unit 994 and a luer port 130. A position of the luer port 130, may be adjusted by tilting the luer port along a direction 919. An opening 930 formed on a distal end 926 of the luer port 130, may be coupled to a luer device (e.g., luer device 140 shown in FIG. 1A) during operation of the sterilization device 1009. The head unit 994 may be attached to a patient using an adhesive surface 942 secured to the head unit 994.

As shown in FIG. 10G, a catheter tube 917 may be mounted inside the catheter channel 965 on the head unit 994, and connected to an access site on the patient, as shown by arrow 955. As an example, the catheter channel 965 may be formed between the first head portion 1019 and second head portion 1021. The catheter channel 965 may have a width 1023 larger than a diameter of the catheter tube 917. For example, the diameter of the catheter tube 917 may range from 2.0 to 7.0 mm, while the width 1065 of the catheter channel 965 may range from 1.0 to 15 mm. In this way, the sterilization device 1009 may be configured with the catheter channel 965 adequately sized to receive the catheter tube 917 that may be attached to one or more access sites on the patient.

Referring to FIG. 10H, a schematic depiction showing a thirty first embodiment of a catheter device 1010 is shown. The catheter device 1010 may be configured with a head unit 980 having a plurality of stacked batteries 120, a first adhesive pad 942, and a plurality of luer devices 951A-C connected to a splicer unit 954 attached to a second adhesive pad 945. Any of the luer devices 951A-C may be coupled to a luer port 130 connected to the head unit 980 of the catheter device 1010 via a connection line 132.

As shown in FIG. 10H, the head unit 980 is coupled to the luer port 130, which is connected to a first catheter line 1016 having the luer device 951A with a communication line 952A leading to one or more access sites on a patient, as shown by arrow 955. The catheter device 1010 also includes a second catheter line 1017 and a third catheter line 1018, each second and third catheter lines having luer devices 951B-C with communication lines 952B and 952C, respectively. The communication lines 952A-C of the first, second and third catheter lines, respectively may be routed through openings in a distal end 957 of the splicer unit 954, and extended to an upstream end 959 of the splicer unit, where each line 952A-C may be coupled to a plurality of access sites on the patient, shown by arrow 955. The catheter device 1010 may be controlled using an electronic system (e.g., control system 1400 shown in FIG. 14) mounted inside the housing 980.

The head unit 980 may be uncoupled from the luer device 951A of the first catheter line 1016, and coupled to the luer device 951B of the second catheter line 1017, when the first catheter line 1016 malfunctions, for example. Alternatively, the head unit 980 may be uncoupled from the luer device 951A of the first catheter line 1016, and coupled to the luer device 951C of the third catheter line 1018. In another example, although not shown, each of the luer devices 951B-C, may be coupled to different catheter head units, similar to the head unit 980 coupled to the luer device 951A, thereby forming a catheter system having a plurality of catheter devices. In other examples, the luer devices 951B-C, may be coupled to a first and second catheter head unit, respectively, each of the first and second catheter head units different from the head unit 980 coupled to the luer device 951A. In this way, the catheter device may comprises one or more head units, connected to a plurality of luer devices coupled to multiple access sites on the patient.

Figure 10J:
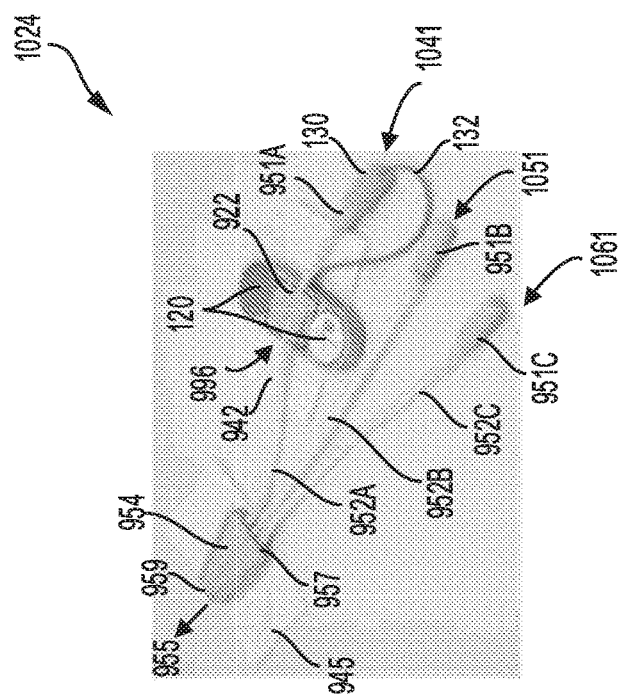
FIG. 10J shows a thirty third embodiment of a sterilization device configured with a head unit having a plurality of stacked batteries; the head unit is attached to an adhesive pad, and connected to a luer port.
Figure 10I:
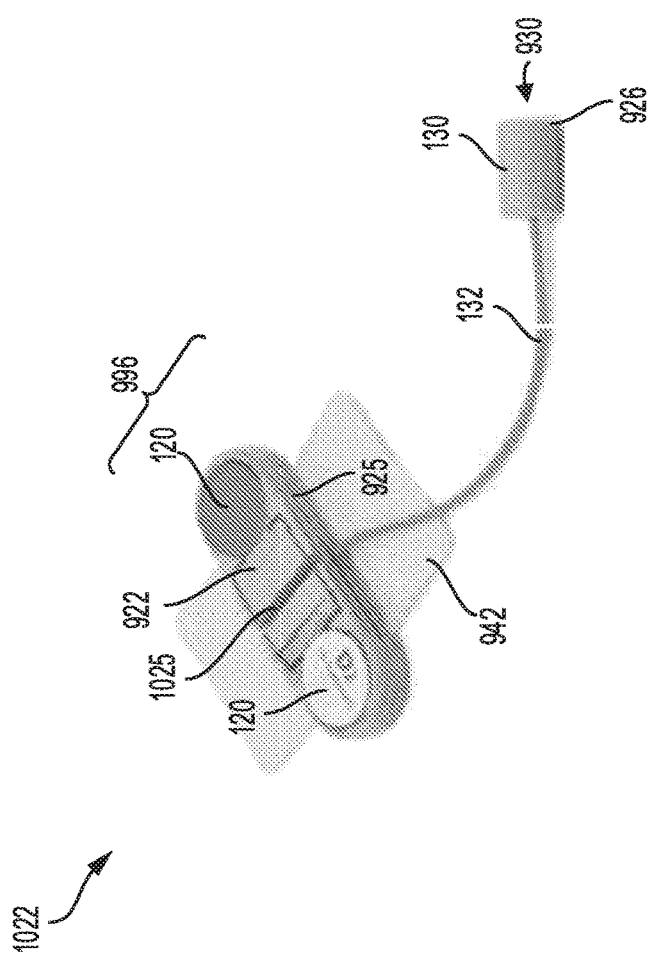
FIG. 10I shows a thirty second embodiment of a sterilization device configured with a head unit having a plurality of stacked batteries, a first adhesive pad, and a plurality of luer ports connected to splicer unit attached to a second adhesive pad.

Referring to FIG. 10I, a schematic depiction showing a thirty second embodiment of a sterilization device 1022 is shown. The sterilization device 1022 may be configured with head unit 996 comprising housing 922 with a channel 1025, and plurality of stacked batteries 120 mounted on either side of the housing 922. As an example, the stacked batteries on the sterilization device 1022, may comprise four or more rechargeable batteries stacked together to provide adequate electrical power to operate the catheter device. The head unit 996 may be a linearly shaped unit coupled to a luer port 130 via a connection line 132 routed through a sidewall 925 of the head unit 996. The luer port 130 of the sterilization device 1022, may include an opening 930 formed at a distal end 926 of the luer port 130, to receive a luer device, such as luer device 951A-C disclosed further below with reference to FIG. 10J. The sterilization device 1022, may include an adhesive surface 942, which attaches to a patient's skin, for example.

Referring to FIG. 10J, a schematic depiction showing a thirty third embodiment of a catheter device 1024 configured with the head unit 996 having multiple stacked batteries 120, a first adhesive pad 942, and a plurality of luer devices 951A-C connected to a splicer unit 954 attached to a second adhesive pad 945. The luer devices 951A-C may be coupled to the luer port 130 connected to the head unit 996 of the catheter device 1024 via the connection line 132.

The head unit 996 may be coupled to the luer port 130, which is connected to a first catheter line 1041 having the luer device 951A with a communication line 952A leading to one or more access sites on a patient, as shown by arrow 955. The catheter device 1024 also includes a second catheter line 1051 and a third catheter line 1061, each second and third catheter lines having luer devices 951B-C with communication lines 952B and 952C, respectively. The communication lines 952A-C of the first, second and third catheter lines, respectively are routed through openings in a distal end 957 of the splicer unit 954, and extended to an upstream end 959 of the splicer unit, where each line 952A-C may be coupled to access sites on the patient, as shown by arrow 955.

The head unit 996 may be uncoupled from the luer device 951A of the first catheter line 1041, and coupled to the luer device 951B of the second catheter line 1051, when the first catheter line 1041 malfunctions, for example. In an alternative example, the head unit 996 may be uncoupled from the luer device 951A of the first catheter line 1041, and coupled to the luer device 951C of the third catheter line 1061. In another example, although not shown, each of the luer devices 951B and 951C, may be coupled to different catheter head units, similar to the head unit 996 coupled to the luer device 951A, forming a catheter system with a plurality of catheter devices. In further examples, each of the luer devices 951B and 951C, may be coupled to a first and second head unit, respectively, each of the first and second head units different from the head unit 996 coupled to the luer device 951A. In this way, the catheter device may comprise a plurality of head units, coupled to a plurality of luer devices that are fluidly coupled to multiple access sites on the patient. The catheter device 1024 may be controlled using an electronic system (e.g., control system 1400 shown in FIG. 14) mounted inside the housing 922. Details on controlling the catheter device are disclosed further below, with reference to FIG. 14.

Figures 10M, 10N:
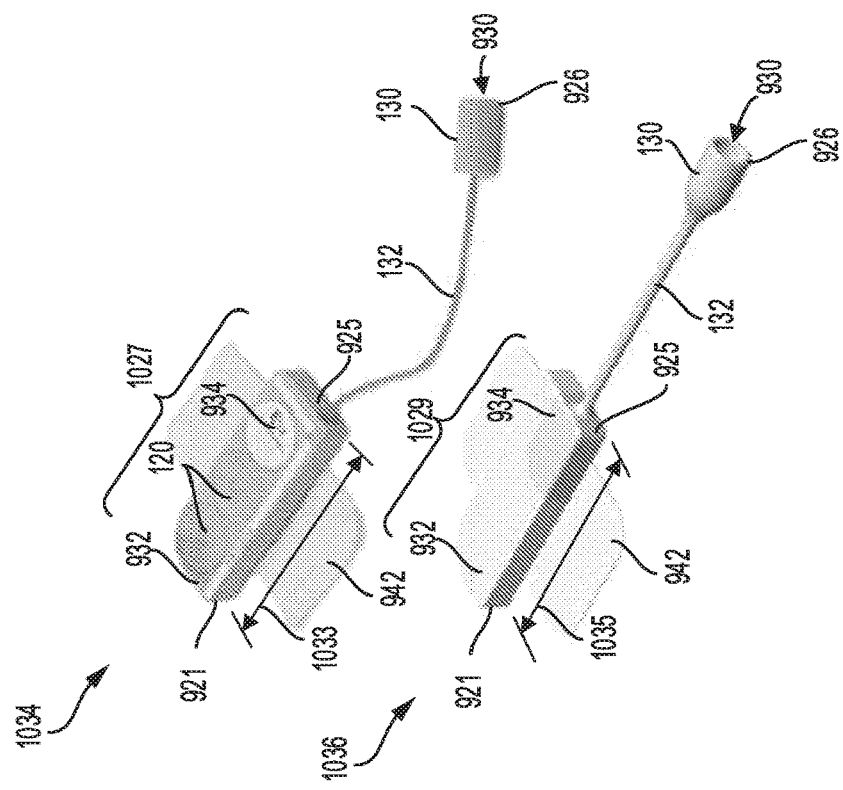
FIG. 10M shows a thirty sixth embodiment of a sterilization device having head unit with a plurality of stacked batteries; the head unit attached to an adhesive pad, includes a luer port.
FIG. 10N shows a thirty seventh embodiment of a sterilization device with a head unit having a plurality of stacked batteries, and a luer port; the head unit is attached to a circular adhesive pad with a ball that allows the head unit to rotate about a fixed axis.
Figures 10K, 10L:
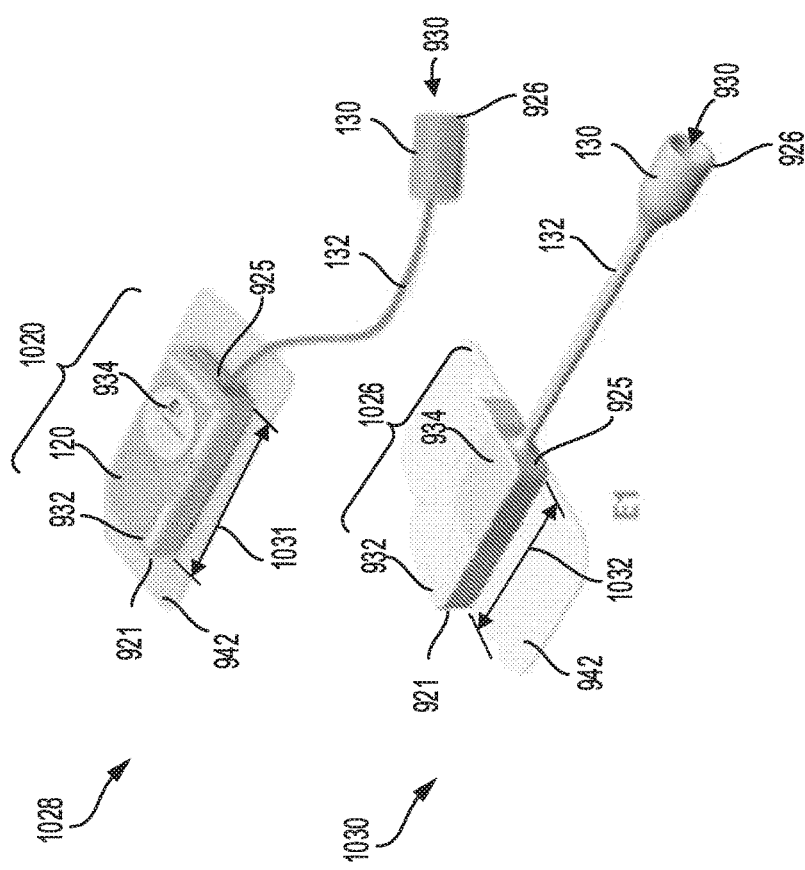
FIG. 10K shows a thirty fourth embodiment of a sterilization device having head unit with a plurality of stacked batteries; the head unit is attached to an adhesive pad, and connected to a luer port.
FIG. 10L shows a thirty fifth embodiment of a sterilization device with head unit having a plurality of stacked batteries; the head unit is attached to an adhesive pad, and connected to a luer port.

Referring to FIGS. 10K-L, a schematic depiction showing a thirty fourth embodiment of a sterilization device 1028 and a thirty fifth embodiment of a sterilization device 1030, respectively is shown. Each of the sterilization devices 1028 and 1030 are configured with head units 1020 and 1026, respectively. Each head unit 1020 and 1026, comprises an upstream end 932 and a downstream end 934. A plurality of stacked batteries 120, may be mounted to the upstream end 932 of the sterilization device 1028. Although not shown, multiple stacked batteries may be mounted in an interior region within the head unit 1026 of the sterilization device 1030. As an example, the stacked batteries in each sterilization device 1028 and 1030, may comprise four or more rechargeable batteries stacked together to provide adequate electrical power to operate each sterilization device.

Each of the head units 1020 and 1026, may be linearly shaped units coupled to a luer port 130 via a connection line 132 routed through a sidewall 925 of each sterilization device 1028 and 1030. Each head unit 1020 and 1026 may include an upstream curved side wall 921. The head units 1020 and 1026 may have a first length 1031 and a second length 1032, respectively. As an example, the first length 1031 of the head unit 1020, may be similar to the second length 1032 of the head unit 1026. In another example, the first length 1031 of the head unit 1020 and second length 1032 of the head unit 1026, may be different (e.g., the first length 1031 may be smaller or larger than the second length 1032).

The luer port 130 in each sterilization device 1028 and 1030, may include an opening 930 formed at a distal end 926 of the luer port, to receive a luer device (e.g., luer device 140 shown in FIG. 1A). The sterilization devices 1028 and 1030, may include an adhesive surface 942, which attaches to the patient's skin. As an example, the adhesive surface 942 of each sterilization device 1028 and 1030, may be coated with a non-bacterial compound such as silver (and variations thereof), chlorhexidine, antibiotic compounds, antimicrobial peptide etc., to reduce occurrence of patient infections and minimize skin irritation. In another example, the adhesive surface 942 of each sterilization device 1028 and 1030, may be comprised of adhesive materials such as pressure sensitive acrylates, latex, hydrocolloids, polyurethane, and silicone based adhesives, that readily attach to the patient's skin without causing skin irritation.

Referring to FIGS. 10M-N, a schematic depiction showing a thirty sixth embodiment of a sterilization device 1034 and a thirty seventh embodiment of a sterilization device 1036, respectively is shown. Each of the sterilization devices 1034 and 1036 are configured with head units 1027 and 1029, respectively. Each head unit 1027 and 1029, comprises an upstream end 932 and a downstream end 934. A plurality of stacked batteries 120, may be mounted to the upstream end 932 of the sterilization device 1034. Although not shown, a plurality of stacked batteries may be mounted in an interior region of the head unit 1029 of the sterilization device 1036. As an example, the stacked batteries of each sterilization device 1034 and 1036, may comprise four or more rechargeable batteries stacked together to provide adequate electrical power to operate each sterilization device.

Each of the head units 1027 and 1029, may be linearly shaped units coupled to a luer port 130 via a connection line 132 routed through a sidewall 925 of each sterilization device 1034 and 1036. Each head unit 1027 and 1029 may include an upstream curved side wall 921. The luer port 130 in each sterilization device 1034 and 1036, may include an opening 930 formed at a distal end 926 of the luer port, to receive a luer device (e.g., luer device 140 shown in FIG. 1A).

As shown in FIGS. 10M-N, the head units 1027 and 1029 may have a first length 1033 and a second length 1035, respectively. As an example, the first length 1033 of the head unit 1027, may be similar to the second length 1035 of the head unit 1029. In another example, the first length 1033 of the head unit 1027 and second length 1035 of the head unit 1029, may be different (e.g., the first length 1033 may be smaller or larger than the second length 1035). In other examples, the first length 1033 and second length 1035 may range from 10 to 200 mm.

The sterilization devices 1034 and 1036, may include an adhesive surface 942, which attaches to the patient's skin. As an example, the adhesive surface 942 on each sterilization device 1034 and 1036 may be coated with a non-bacterial compounds to reduce occurrence of patient infections and minimize skin irritation. In other examples, the adhesive surface 942 on each sterilization device 1034 and 1036, may be comprised of adhesive materials that readily attach to the patient's skin without causing skin irritation.

Referring to FIGS. 10O-P, a schematic depiction showing a thirty eighth embodiment of a sterilization device 1038 and a thirty ninth embodiment of a sterilization device 1040, respectively is shown. The sterilization devices 1038 and 1040 may be configured with head units 1037 and 1039, respectively. Each head unit 1037 and 1039, comprises an upstream end 932 and a downstream end 934. A plurality of stacked batteries 120 may be mounted to the upstream end 932 of the sterilization device 1038. Although not shown, multiple stacked batteries may be mounted in an interior region of the head unit 1039 of the sterilization device 1040. As an example, the stacked batteries in each sterilization device 1038 and 1040, may comprises four or more rechargeable batteries stacked together to provide adequate electrical power to operate each sterilization device.

Each of the head units 1037 and 1039, may be linearly shaped units configured with an upstream curved wall 921 and a recessed slot 1073. The head units 1037 and 1039, also include a luer port 130 having an opening 930 formed at a distal end 926 of each sterilization device 1038 and 1040, to receive a luer device (e.g., luer device 140 shown in FIG. 1A). The sterilization devices 1038 and 1040, may include adhesive surfaces 942 and 1070, respectively, which attach to the patient's skin. As an example, the adhesive surfaces 942 and 1070, may have various shapes including rectangular, circular and other suitable shapes. In one example, the adhesive surface 1070 is a circular shaped surface with a ball and pin assembly that allows the sterilization device 1040 to rotate about a fixed point, as shown by arrow 1072. Details of the ball and pin assembly are disclosed further below with reference to FIG. 10R. In other examples, the adhesive surfaces 942 and 1070 may be coated with a non-bacterial compounds to minimize skin irritation, and reduce occurrence of patient infections.

Referring to FIG. 10Q, a schematic depiction showing an alternative embodiment of a sterilization device 1042 is shown. The sterilization device 1042 may be configured with head unit 1043, similar to head unit 1039 of sterilization device 1040. The head unit 1043, may include an upstream end 932 and a downstream end 934. A first and a second stack 1080 and 1081, respectively of batteries may be mounted in an interior region 1084, upstream of a luer port 130 with an opening 930. The head unit 1043 is mounted to a ball 1076 attached to an adhesive surface 1070.

Each of first and second stack 1080 and 1081 of batteries, may be of rechargeable batteries, mounted below a plate 1082 inside the interior space 1084. The first and second stack of batteries, may be stacked together to provide adequate electrical power to operate the sterilization device 1042, for example. The first and second stack of batteries may be mounted in the interior space 1084, such that a gap 1086 formed between the first and second stack of batteries is larger enough to receive the ball 1076 and a vertical pin, such as vertical pin 1078 shown in FIG. 10R.

Referring now to FIG. 10R, a schematic view 1044 of the adhesive surface 1070 having the ball 1076 and vertical pin 1078 assembly is shown. The ball 1076 may be mounted to a circular disc 1075 attached to an outer surface 1071 of the adhesive surface 1070. The vertical pin 1078 may be attached to the ball 1076 in a manner that allows for easy mounting of the head unit 1043, shown in FIG. 10Q. The adhesive surface 1070 may be comprised of an adhesive material that attaches to the patient's skin without causing skin irritation while minimizing bacterial infection on the patient.

Turning back to FIG. 10Q, the ball 1076 and vertical pin 1078 of the adhesive surface 1070 may be mounted through an opening 1083 in the head unit 1043. When mounted to the adhesive surface 1070, the head unit 1043 may rotate about the ball 1076 and vertical pin 1078, thereby allowing for easy orientation and handling of the sterilization device 1042. In this way, the sterilization device 1042, may be easily oriented in a direction of a catheter line coupled to access sites on the patient.

Referring to FIGS. 10S-T, a schematic depiction showing a fortieth embodiment of a sterilization device 1050 and a forty first embodiment of a sterilization device 1052, respectively is shown. The sterilization devices 1050 and 1052 may be configured with head units 1090 and 1092, respectively. Each head unit 1090 and 1092, comprises an upstream end 932 and a downstream end 934. A plurality of stacked batteries 120, are mounted to the sterilization device 1050. Although not shown, a plurality of stacked batteries may be mounted in an interior region (e.g., interior space 1084 shown in FIG. 10Q) within the head unit 1092 of the sterilization device 1050. As an example, the stacked batteries in each sterilization device 1050 and 1052, may comprises four or more rechargeable batteries, stacked together to provide adequate electrical power to operate each sterilization device.

Each head unit 1090 and 1092 includes an upstream curved wall 921 and a curved side wall 925. The head units 1090 and 1092, may be linearly shaped units coupled to a luer port 130 via a connection line 132 routed through the curved side wall 925 of each sterilization device 1050 and 1052. The luer port 130 in each sterilization device 1050 and 1052, includes an opening 930 formed at a distal end 926 of each sterilization device 1050 and 1052, to receive a luer device (e.g., luer device 951A-C shown in FIG. 10J). The sterilization devices 1050 and 1052, may include an adhesive surface 942, which attaches to the patient's skin. As an example, the adhesive surface 942 on each sterilization device 1050 and 1052 may be coated with non-bacterial compounds to reduce occurrence of patient infections and minimize skin irritation. In another example, the adhesive surface 942 on each sterilization device 1050 and 1052, may be comprised of adhesive materials that readily attach to the patient's skin without causing skin irritation.

Referring to FIGS. 10U-10V, a schematic depiction showing a forty second embodiment of a sterilization device 1054 and a forty third embodiment of a sterilization device 1056, respectively is shown. The sterilization devices 1054 and 1056 are configured with head units 1094 and 1095, respectively. Each head unit 1094 and 1095, comprises an upstream end 932 and a downstream end 934. Although not shown, multiple stacked batteries may be mounted in an interior region (e.g., interior space 1084 shown in FIG. 10Q) of each head unit 1094 and 1095. As an example, the stacked batteries in each head unit 1094 and 1095, may comprises four or more rechargeable batteries stacked together to provide adequate electrical power to operate each sterilization device 1054 and 1056.

Each of the head units 1094 and 1095, may be linearly shaped units configured with an upstream curved wall 921 and curved side wall 925. The head units 1090 and 1092, also include a luer port 1091 having an opening 930 formed at a distal end 926 of each sterilization device 1054 and 1056, to receive a luer device (e.g., luer device 140 shown in FIG. 1A). The luer port 1091 of the sterilization device 1056 may have a recessed slot 1093 that enables easy coupling with a luer device. The sterilization devices 1054 and 1056, may include adhesive surfaces 942 and 1070, respectively, which attach to the patient's skin. As an example, the adhesive surfaces 942 and 1070, may have various shapes including rectangular, circular and other suitable shapes. In one example, the adhesive surface 1070 is a circular shaped surface with a ball and pin (e.g., ball 1076 and vertical pin 1078 shown in FIG. 10R) assembly that allows the sterilization device 1056 to rotate about a fixed point, as shown by arrow 1072. In other examples, the adhesive surfaces 942 and 1070 may be coated with a non-bacterial compounds to minimize skin irritation, and reduce occurrence of patient infections.

Referring to FIGS. 10W-10X, a schematic depiction showing a forty fourth embodiment of a sterilization device 1058 and a forty fifth embodiment of a sterilization device 1060, respectively is shown. The sterilization devices 1058 and 1060 are configured with head units 1096 and 1097, respectively. Each head unit 1096 and 1097, may comprise an upstream end 932 and a downstream end 934. Although not shown, a plurality of stacked batteries (e.g. battery stacks 1080 and 1081 shown in FIG. 10Q) may be mounted in an interior region (e.g., interior space 1084 shown in FIG. 10Q) within each head unit 1096 and 1097. As an example, the stacked batteries in each head unit 1096 and 1097, may comprises four or more rechargeable batteries, stacked together to provide adequate electrical power to operate each sterilization device 1058 and 1060.

Each head unit 1096 and 1097, includes an upstream curved wall 921 and a downstream curved wall 925. The head units 1096 and 1097, may be linearly shaped units coupled to a luer port 130 via a connection line 132 routed through the downstream curved wall 925 of each sterilization device 1058 and 1060. The luer port 130 in each sterilization device 1058 and 1060, includes an opening 930 formed at a distal end 926 of the luer port, to receive a luer device (e.g., luer device 951A-C shown in FIG. 10J). The sterilization devices 1058 and 1060, may include an adhesive surface 942, which attaches to the patient's skin. As an example, the adhesive surface 942 on each sterilization device 1058 and 1060 may be coated with non-bacterial compounds to reduce occurrence of patient infections and minimize skin irritation. In another example, the adhesive surface 942 on each sterilization device 1058 and 1060, may be comprised of adhesive materials that readily attach to the patient's skin without causing skin irritation.

Referring to FIGS. 10Y-Z, a schematic depiction showing a forty sixth embodiment of a sterilization device 1062 and a forty seventh embodiment of a sterilization device 1064, respectively is shown. The sterilization devices 1062 and 1064 are configured with head units 1098 and 1099, respectively. Each head unit 1098 and 1099, comprises an upstream end 932 and a downstream end 934. Although not shown, a plurality of stacked batteries are mounted in an interior region (e.g., interior space 1084 shown in FIG. 10Q) of each head unit 1098 and 1099. As an example, the stacked batteries in each head unit 1098 and 1099, may comprises four or more rechargeable batteries stacked together to provide adequate electrical power to operate each sterilization device 1062 and 1064.

Each of the head units 1098 and 1099, may be triangularly shaped units configured with an upstream curved wall 1045 and downstream curved sidewalls 1047. The head units 1098 and 1099, also include a luer port 1091 having an opening 930 formed at a distal end 926 of the luer port, to receive a luer device (e.g., luer device 140 shown in FIG. 1A). The sterilization devices 1062 and 1064, may include adhesive surfaces 942 and 1070, respectively. As an example, the adhesive surfaces 942 and 1070, may be comprised of adhesive materials that may be used to attach each sterilization device 1062 and 1064 to the patient's skin. In another example, the adhesive surfaces 942 and 1070, may have various shapes including rectangular, circular and other suitable shapes. In one example, the adhesive surface 1070 is a circular shaped surface with a ball and pin (e.g., ball 1076 and vertical pin 1078 shown in FIG. 10R) assembly that allows the sterilization device 1062 to rotate about a fixed point, as shown by arrow 1072. In other examples, the adhesive surfaces 942 and 1070 may be coated with a non-bacterial compounds to minimize skin irritation, and reduce occurrence of patient infections.

Figure 11B:
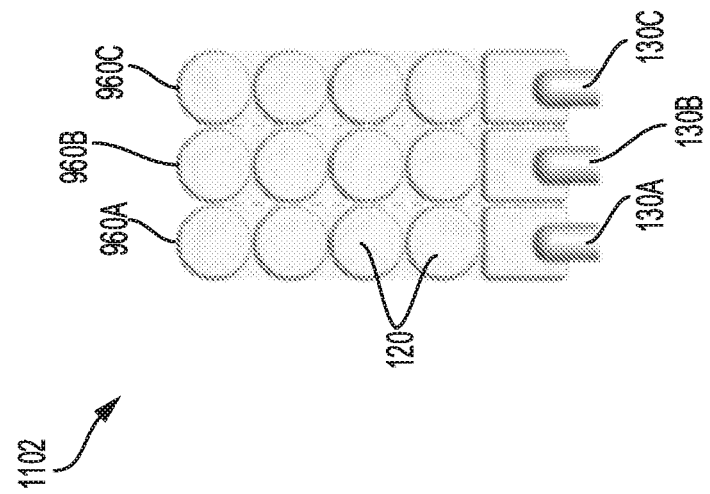
FIG. 11B shows a forty ninth embodiment of a sterilization device with a plurality of head units grouped together; each head unit connected to a luer port.
Figure 11A:
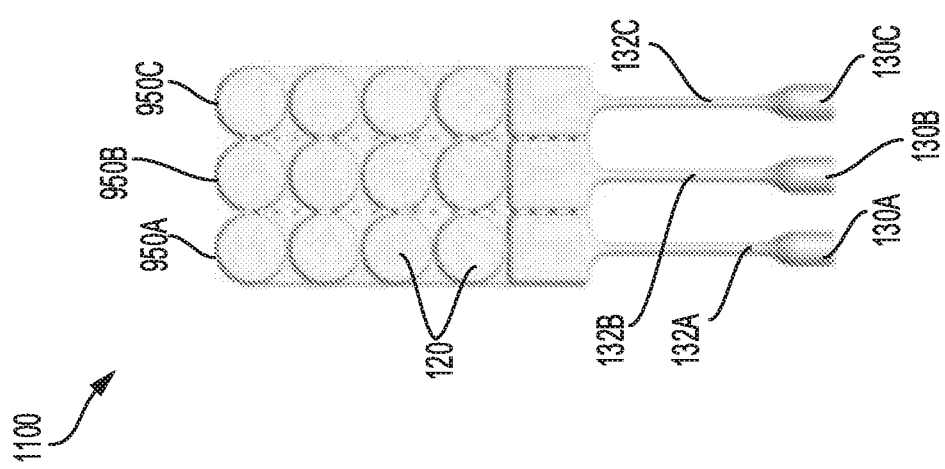
FIG. 11A shows a forty sixth eighth embodiment of a sterilization device with a plurality of head units grouped together; each head unit connected to a luer port.

Referring to FIGS. 11A-11B, a schematic depiction showing a forty eighth embodiment of a sterilization system 1100 and a forty ninth embodiment of a sterilization system 1102, respectively is shown. The sterilization systems 1100 and 1102 have a plurality of head units 950A-C and 960A-C, respectively.

The head units 950A-C of the sterilization system 1100, may be coupled to luer ports 130A-C via connection lines 132A-C, respectively. Each head unit 950A-C includes a plurality of batteries 120 that provide electrical power to operate the sterilization system 1100. As an example, the sterilization system 1100 may comprise multiple sterilization devices, such as sterilization devices 903 disclosed with reference to FIG. 9D. As an example, one or more head unit 950A-C of the sterilization system 1100, may connect to a luer device, such as luer device 140 shown in FIG. 1A, coupled to one or more access sites on the patient.

As shown in FIG. 11B, the head units 960A-C, may be coupled to luer ports 130A-C via connection lines 132A-C, respectively. Each head unit 960A-C includes a plurality of batteries 120 that provide electrical power to operate the sterilization system 1102. The sterilization system 1102 may comprise a plurality of sterilization devices, such as sterilization devices 905 disclosed with reference to FIG. 9F. As an example, one or more head unit 960A-C of the sterilization system 1102, may connect to the luer device coupled to access sites on the patient.

Although not shown, each sterilization system 1100 and 1102, may have an adhesive surface (such as adhesive surface 928 shown in FIGS. 9D-F) that attaches a skin of the patient during sterilization operation. In this way, each sterilization system 1100 and 1102, may comprise one or more sterilization devices coupled to one or more access sites on the patient.

Figure 11C:
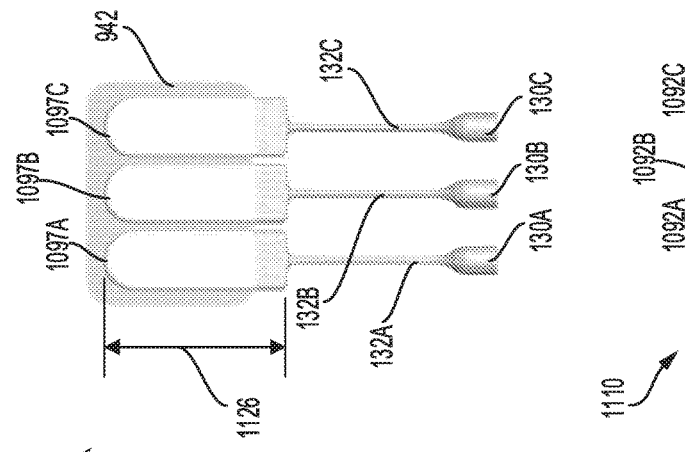
FIG. 11C shows a fiftieth embodiment of a sterilization device with a plurality of head units grouped together; each head unit connected to a luer port and attached to an adhesive pad.
Figure 11D:
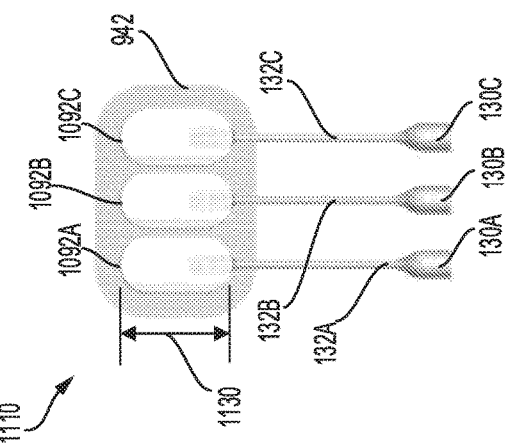
FIGS. 11D-11H show a fifty first to fifty fifth embodiment, respectively of a sterilization device with a plurality of head units grouped together; each head unit connected to a luer port and attached to an adhesive pad.

Referring to FIGS. 11C-D, a schematic depiction showing a fiftieth embodiment of a sterilization system 1104 and a fifty first embodiment of a sterilization system 1106, respectively is shown. Although not shown, each sterilization system 1104 and 1106 may include a plurality of batteries (e.g., battery stacks 1080 and 1081 shown in FIG. 0.10Q) that provide electrical power to the sterilization systems 1104 and 1106.

As shown in FIG. 11C, the sterilization system 1104 includes a plurality of sterilization head units 970A-C, connected to luer ports 130A-C via connection lines 132A-C, respectively. As an example, the sterilization system 1104 may comprise multiple sterilization devices, such as sterilization devices 906 disclosed with reference to FIG. 9G. As an example, one or more head units 970A-C of the sterilization system 1104, may connect to a luer device (e.g., luer device 140 shown in FIG. 1A) coupled to one or more access sites on the patient. Each head unit 970A-C of the sterilization system 1104 has a first length 1124. As an example, the first length 1124 may range from 5.0 to 100 mm.

As shown in FIG. 11D, sterilization system 1106 includes a plurality of head units 1097A-C, connected to luer ports 130A-C via connection lines 132A-C, respectively. Although not shown, each head unit 1097A-C may include a plurality of batteries that provide electrical power to operate the sterilization system 1106. The sterilization system 1106 may comprise a plurality of sterilization devices, such as sterilization devices 1060 disclosed with reference to FIG. 10X. As an example, one or more head units 1097A-C of the sterilization system 1106, may connect to the luer device coupled to multiple access sites on the patient. Each head unit 1097A-C may have a second length 1126, smaller than the first length 1124 of each head unit 970A-C of sterilization system 1104. As an example, the second length 1126 may range from 5.0 to 100 mm.

Each sterilization system 1104 and 1106, may have an adhesive surface 942, which attaches to the patient skin during sterilization operation. The sterilization system 1104, may include a connection loop 1122 for strapping each head unit 970A-C to the adhesive surface 942. As an example, the connection loops 1122 may enable each individual head unit 970A-C to be securely strapped to the adhesive pad 942 during sterilization operation.

In this way, each sterilization system 1104 and 1106, may comprise one or more sterilization devices coupled to a plurality of access sites on the patient. Since an individual sterilization device or a group of sterilization devices of each sterilization system 1104 and 1106 may be operated, system failure attributed to malfunction of a component of any of the sterilization devices may not significantly impact sterilization operation. By operating one or more sterilization devices of each sterilization system 1104 and 1106, system disruptions due to component malfunction may be reduced while minimizing occurrence of patient infections.

Figure 11E:
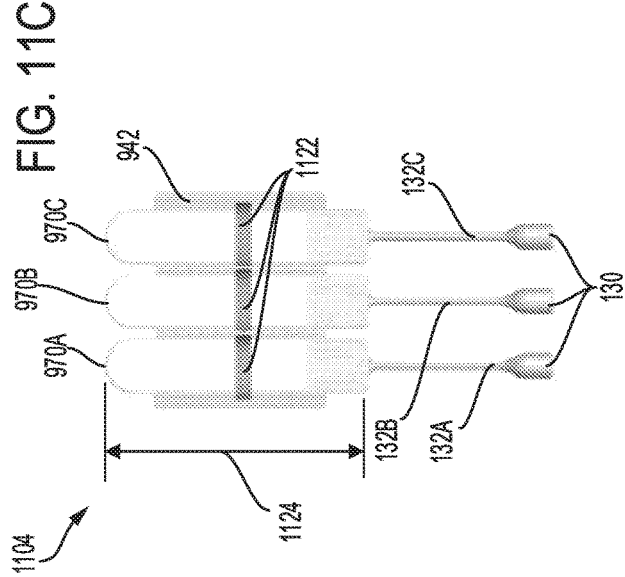
Figure 11F:
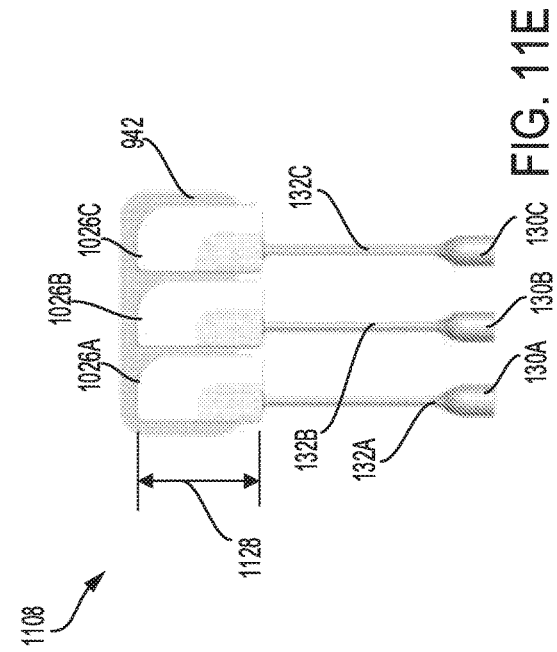

Referring to FIGS. 11E-F, a schematic depiction showing a fifty second embodiment of a sterilization system 1108 and a fifty third embodiment of a sterilization system 1110, respectively is shown. Although not shown, each sterilization system 1108 and 1110 may include a plurality of rechargeable batteries which provide electrical power to the sterilization systems 1108 and 1110. Each sterilization system 1108 and 1110 has an adhesive surface 942, which attaches to the patient skin during sterilization operation.

The sterilization system 1108 may include head units 1026A-C, connected to luer ports 130A-C via connection lines 132A-C, respectively, as shown in FIG. 11E. The sterilization system 1108 may comprise multiple sterilization devices, such as sterilization devices 1030 disclosed with reference to FIG. 10L. As an example, one or more head unit 1026A-C of the sterilization system 1108, may connect to a luer device (e.g., luer device 140 shown in FIG. 1) coupled to one or more access sites on the patient. Each head unit 1026A-C may have a third length 1128. As an example, the third length 1128 may range from 5.0 to 100 mm.

As shown in FIG. 11F, sterilization system 1110 includes a plurality of head units 1092A-C, connected to luer ports 130A-C via connection lines 132A-C, respectively. The sterilization system 1110 may comprise a plurality of sterilization devices, such as sterilization devices 1052 disclosed with reference to FIG. 10T. As an example, any of the head units 1026A-C of the sterilization system 1110, may connect to the luer device coupled to multiple access sites on the patient. Each of the head units 1026A-C of the sterilization system 1110 may have a fourth length 1130, smaller or larger than the third length 1128 of each of the head units 1026A-C. As an example, the fourth length 1130 may range from 5 to 100 mm.

In this way, each sterilization system 1108 and 1110, may comprise one or more sterilization devices coupled to a plurality of access sites on the patient. Individual sterilization devices or a group of sterilization devices in each sterilization system 1108 and 1110, may be operated to minimize system disruptions. By operating one or more sterilization devices of each sterilization system 1108 and 1110, system disruptions due to component malfunction may be reduced while minimizing occurrence of patient infections.

Figure 11H:
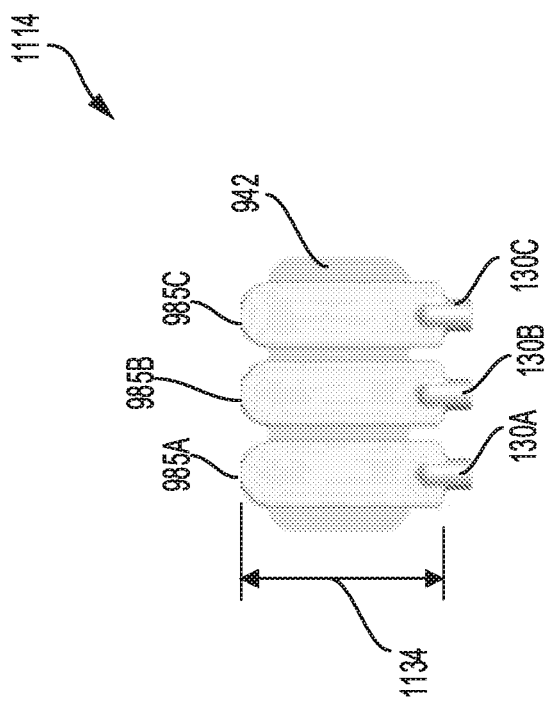
Figure 11G:
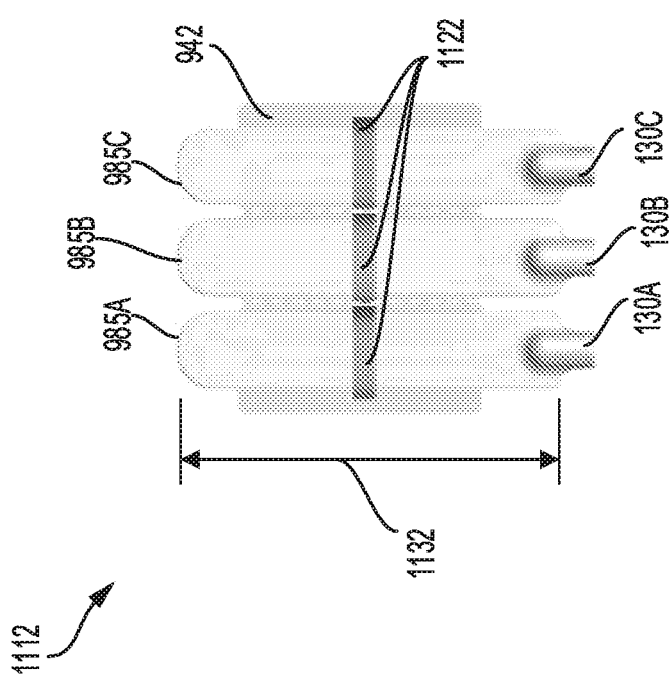

Referring to FIGS. 11G-H, a schematic depiction showing a fifty fourth embodiment of a sterilization system 1112 and a fifty fifth embodiment of a sterilization system 1114, respectively is shown. Although not shown, each sterilization system 1112 and 1114 includes a plurality of rechargeable batteries which provide electrical power to the sterilization systems. Each sterilization system 1112 and 1114 has an adhesive surface 942, which attaches to the patient skin during sterilization operation.

As shown in FIGS. 11G-H, each sterilization system 1112 and 1114, includes head units 984A-C, configured with luer ports 130A-C. The sterilization systems 1112 and 1114, may comprise multiple sterilization devices, such as sterilization devices 908 disclosed with reference to FIG. 9I. As an example, one or more head units 984A-C of each sterilization system 1112 and 1114, may connect to a luer device (e.g., luer device 140 shown in FIG. 1A), coupled to one or more access sites on the patient. Each head unit 984A-C of the sterilization system 1112 may have a fifth length 1132. Similarly, each head unit 984A-C of the sterilization system 1114 may have a sixth length 1134. As an example, the fifth length 1132 of each head unit 984A-C of the sterilization system 1112 may be greater than the sixth length 1134 of the head units in the sterilization system 1114. In one example, the fifth length 1132 of the head units 984A-C in sterilization system 1112 may range from 5 to 100 mm, and the sixth length 1134 of the head units in sterilization system 1112 may range from 5 to 100 mm.

In this way, each sterilization system 1112 and 1114, may comprise one or more sterilization devices coupled to a plurality of access sites on the patient. An individual sterilization device or a group of sterilization devices in each sterilization system 1112 and 1114, may be operated to minimize system disruptions. By operating one or more sterilization devices of each sterilization system 1112 and 1114, system disruptions due to component malfunction may be reduced to minimize patient infections.

Referring to FIGS. 12A-12B, a first view 1200 and a second view 1202, respectively of a fifty sixth embodiment of a catheter device 1204 is shown. The catheter device 1204 is configured with head unit 1092 having an upstream end 932 and a downstream end 934. Although not shown, a plurality of stacked batteries (e.g., battery stacks 1080 and 1081 shown in FIG. 10Q) may be mounted in an interior region (e.g., interior space 1084 shown in FIG. 10Q) of the head unit 1092. As an example, the stacked batteries in the head unit 1092, may comprise four or more rechargeable batteries stacked together to provide adequate electrical power to operate the catheter device 1204. The catheter device 1204, may include an adhesive surface 942, which attaches to a patient's skin during patient therapy.

As shown in FIGS. 12A-B, the head unit 1092, may be a linearly shaped unit, configured with an upstream curved wall 1203 and downstream curved sidewall 1205. The head unit 1092 is connected to a luer port 1210 via a connection line 132, routed through the curved sidewall 1205. An upstream end 1224 of the luer port 1210 is coupled to the connection line 132, which may transmit electrical power from the head unit 1092 to the luer port during operation of the catheter device 1204. The luer port 1210 has a plurality of openings 1214A-C separated by sidewalls 1212. As an example, each opening 1214A-C may be configured with a suitable diameter to receive each luer device 1215A-C, as shown in FIG. 12B. In one example, each luer device 1215A-C may be mounted in each of the openings 1214A-C of the luer port 1210. The luer devices 1215A-C may be coupled to catheter lines 1216A-C, respectively. Each of the catheter lines 1216A-C, may be coupled to a plurality of access sites on the patient, as shown by each arrow 1218A-C.

As shown in FIG. 12B, the luer port 1210 may include a ultra-violet (UV) light source 1222 mounted upstream of a disc 1226. As an example, the UV light source 1222 may be positioned between the disc 1226 and each of the openings 1214A-C, thereby allowing UV radiation released by the UV light source 1222 to travel through each catheter line 1216A-C via each luer device 1215A-C. In one example, the released UV radiation from the UV light source 1222, may be transmitted to the access sites 1218A-C on the patient via catheter lines 1216A-C, respectively. In other examples, the UV radiation released to sterilize catheter lines 1216A-C and access sites 1218A-C on the patient, may have wavelengths ranging from 100 nm to 280 nm. In further examples, the UV radiation may be discharged for a duration ranging from 1 second to 10 minutes, during a sterilization operation. In this way, the catheter device 1204 may be used to sterilize catheter lines 1216A-C and the access sites 1218A-C on the patient to minimize patient infections.

Turning to FIG. 13, an example routine for operating a catheter device, such as the catheter device shown in FIGS. 1A-12B is shown. The example routine may be stored as instructions in a control system of the catheter device, such as in a microprocessor described in more detailed with reference to FIG. 14. For example, instructions for carrying out method 1300 and the rest of the methods included herein may be executed by a microcontroller based on instructions stored on a memory of the microcontroller and in conjunction with signals received from sensors and/or signals sent to actuators of the catheter device.

At 1302, the method 1300 may include initializing the catheter device by turning on one or more limit switches of an electronic control system, such as the control system disclosed with reference to FIG. 14. As an example, the initialization may include reading whether the limit switches are activated. In one example, the initialization occurs only if multiple (e.g., two or more) limit switches are engaged, such as by proper insertion of a luer device into a luer port (e.g., luer device 140 into luer port 130 at FIG. 1A). Once the limit switches are engaged, a UV light source may be enabled and energized.

At 1304, the method 1300 includes retrieving previously saved data, such as battery life of batteries connected to the catheter device, operation hours of the UV light source, number of operation cycles, etc. The stored data may be retrieved from a memory of the microcontroller to check if battery level or UV light source has sufficient power for a preceding sterilization procedure, for example.

Next at 1306, the routine may include updating status information based on current operating conditions. As an example, communication between the catheter device and an external device may enable status information to be monitored. In one example, the status information may include battery life, hours of operation and a history of catheter operation. In some examples, transmission of information from the catheter device may provide real-time operation data of the device. In other examples, transmission of information from the catheter device may provide historical use and status information. For example, information regarding activated duration of the UV light source may be stored for transmission. In some examples, the catheter device may receive instructions from an external computing device. The external computing device may request information such as an operation condition of the catheter device, activated duration of the UV source or status information transmission. The routine may further provide operation instructions for controlling and powering the UV light source or for additional sterilization routines.

At 1308, the method 1300 includes generating indication information based on measured or estimated data. As an example, if only a first limit switch is engaged, but not a second limit switch, an error determination may be made by the microprocessor and an indication message generated. In one example, the indication message may indicate a malfunction in a catheter display light. As a result, an error code may be generated and stored in memory of the microcontroller, and/or communicating with an external device to determine a cause of degradation or malfunction via wireless or a suitable communication mode. Method 1300 proceeds to exit.

Note that the control system may receive signals from the various sensors of the catheter device and may employ various actuators of the device to adjust operation based on the received signals and/or internally generated data. Further, the control system may adjust operation of the catheter device based on instructions stored on a memory of the microcontroller. For example, the instructions may control activation, power, deactivation, operation, etc. of the UV light source responsive to a calculated sterilization duration, measured battery voltage, etc.

Referring to FIG. 14, an example electronic control system 1400 for the catheter device having a body component 1401 is shown. As an example, the electronic control system may be mounted to the body component 1401, such as a catheter head unit (e.g., catheter head unit 110 at FIGS. 1A-2B) or other suitable catheter components. The control system 1400 includes an electrical power source 1402 coupled with two interlocking switches 1404. As an example, the electrical power source may include one or more rechargeable batteries used to power the catheter device. In one example, a plurality of CR2032 batteries or other suitable batteries may be used. The interlock switches 1404 may be integrated within the electronic control system 1400 as depicted. In one example, the interlock switches 1404 may provide double fault failsafe operation.

Further, the electronic control system 1400 may include an efficiency converter 1406, connected to a microcontroller 1412, and current driver 1408. As an example, the efficiency converter may be a direct current converter. The microcontroller 1412 may be a conventional microcomputer including: microprocessor unit 1414, read-only memory (ROM) 1415 (e.g., non-transitory memory), random access memory (RAM) 1416, and a conventional data bus 1418. The microcontroller 1412 may receive various signals from sensors coupled or mounted to the catheter device, including signals received from sensors and/or signals sent to actuators of the catheter device. The microcontroller receives signals from the various sensors of the catheter device and employs the various actuators of the device to adjust catheter operation based on the received signals and instructions stored on a memory of the microcontroller. For example, based on input from a power signal sensor regarding power signal sent from the power source, the microcontroller may actuate UV light source 535 to provide UV light with a specific wavelength in a range of 100-280 nm to sterilize the catheter device.

During catheter operation, the UV light source may be powered by rechargeable batteries, and controlled by driver 1408 which is actuated via interlock switches 1404 and/or microcontroller 1412. As an example, the UV light source may be turned on via the driver 1408 based on feedback from one or more sensors including a photodiode and/or limit switches. Also shown, the catheter device may include an optional display window 1422 for observing operation of the UV light source. As an example, the display window 1422 may provide visible status information on operation of the UV light source. In another example, the display window 1422 be comprised of UV sensitive material generating visible light in a presence of UV energy. In one example, the UV sensitive material may comprise a fluorescing material that glows when radiated with UV radiation. In other examples, the display window 1422 may be positioned adjacent to the main opening in the luer port. Similarly, optional status display screen 1420 may be included to indicate power status, such as on/off status of the catheter device.

In this way, the catheter device may be controlled by the electronic control system to adjust operation of the catheter device based on instructions stored on the memory of the microcontroller. For example, the instructions may control activation and deactivation of the UV light source responsive to a calculated sterilization duration, measured battery voltage, and other system parameters.

Figure 15:
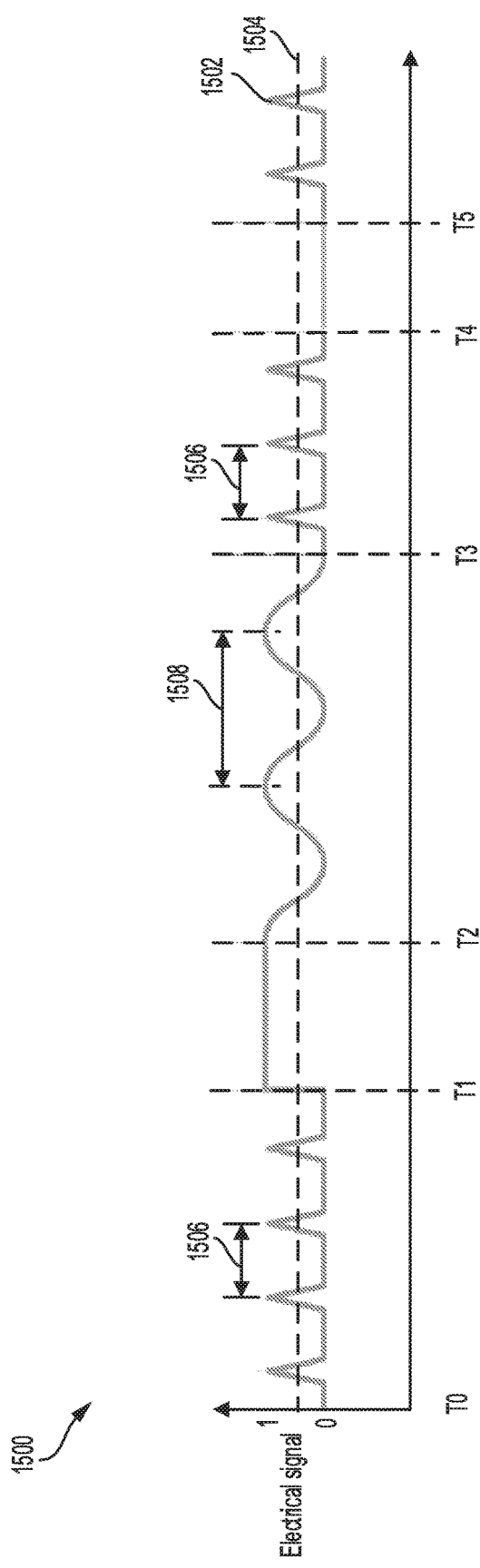
FIG. 15 shows an example graphical output from the catheter device before and during a sterilization operation.

Referring to FIG. 15, an example graphical output 1500 is depicted for a catheter device, such as the catheter device shown in FIGS. 1A-12B. The sequence of FIG. 15 may be provided by executing instructions in the system of FIGS. 1A-12B and FIG. 14 according to the method of FIG. 13.

Vertical markers at times T0-T5 represent times of interest during the sequence. In a plot depicting electrical signal versus time shown below, the horizontal axis represents time, and time increases from the left side of the plot to the right side of the plot. The vertical axis represents the electrical signal emitted by the catheter device and the electrical signal increases in the direction of the vertical axis. Trace 1502 represents the electrical signal, and horizontal line 1504 represents a threshold electrical signal level. A value "0" represents a condition when the electrical signal is at a minimum valve, and a value "1" represents a condition when the electrical signal is at a maximum valve above the threshold electrical signal level 1504.

Prior to T1, a luer device (e.g., luer device 140 shown in FIG. 1A) of the catheter device may be unattached from a luer port (e.g., luer port 130 shown in FIG. 1A) of the device, and the catheter device may be turned on. As a result, the catheter device may emit a pulsating electrical signal 1502 having pointed peaks and flat troughs. The pulsating electrical signal 1502 may fluctuate between the minimum and maximum value of the electrical signal. As an example, the peaks of the pulsating electrical signal may have a first spacing 1506, that defines a first wave length and period of the electrical signal 1502. In this case, the catheter device may be undergoing a warm up phase prior to insertion of the luer device into the luer port. A light display (such as indicator light 706 shown in FIG. 7) on the catheter device may be flashing, thereby indicating that the catheter device is in an operational mode.

At T1, the luer device is mounted into the luer port of the catheter device. As an example, mounting the luer device into the luer port involves inserting an upstream end of the luer device into an opening (such as opening 138 shown in FIG. 1E) in the luer port. Subsequently, a locking pin (e.g., threads 147 shown in FIG. 1A) on the luer device may be adjusted into a locking position within the luer port. As a result, the electrical signal may increase above the threshold electrical signal level 1504.

Between T1 and T2, the electrical signal 1502, may remain at a steady level above the threshold electrical signal level 1504. In this case, the catheter device may remain turned on until a ultra-violet (UV) light source (such as light source 535 shown in FIG. 5) in the luer port of the catheter device is activated. The light display on the catheter device may continue flashing, indicating that the catheter device is still in the operational mode.

At T2, the electrical signal 1502 remains at the steady level above threshold signal 1504. As a result, the ultraviolet light source in the luer port may be turned, and the catheter device may start sanitizing the luer device and luer access port. As an example, the UV light source in the luer port of the catheter device may be activated by turning on interlock switches (e.g., switches 1404 shown in FIG. 14) of an electronic control system, such as the control system disclosed with reference to FIG. 14. The UV light source may be controlled by a current driver (e.g., driver 1408) of the electronic control system, for example.

Between T2 and T3, the electrical signal 1502 may pulsate about the threshold electrical signal level 1504. As an example, the pulsating electrical signal may have broad peaks and shallow troughs. In one example, the pulsating electrical signal may have a second spacing 1508 that defines a second wave length and a second period of the electrical signal 1502. As an example, the second wave length of the pulsating electrical signal may range from 100-280 nm, thereby providing UV radiation in a ultra-violet C spectrum that may adequately sterilize luer device, luer access port including access sites on the patient. In this way, the UV light source may be used to adequately sterilize the luer device, luer access port and access sites on the patient while minimizing patient infections.

At T3, the electrical signal 1502 may decrease below the threshold electrical signal level 1504. Subsequently, the UV light source may be turned off, to stop the sterilization process. As an example, the sterilization process may be stopped after a predetermined duration programmed into the electronic control system of the catheter device. The luer device may remain mounted to the luer port of the catheter device.

Between T3 and T4, the electrical signal 1502 may again pulsate about the threshold signal level 1504, with the peaks of electrical signal spaced at the fast spacing 1506. The electrical signal 1502 may be pulsating at the first wave length and period, for example. At T4, the electrical signal 1502 decreases below the threshold electrical signal level 1504, and the luer device may be detached from the luer port. As an example, the locking pin of the luer device may be adjusted from the locking position to an unlocked position, thereby allowing the luer device to be removed from the luer port. As a result, the display light on the catheter device may be turned off.

Between T4 and T5, the electrical signal 1502 remains below the threshold electrical signal level 1504. The display light on the catheter device may remain turned off, thereby indicating that the catheter device is switched off.

At T5, the catheter device may be turned on again. As a result, the electrical signal 1502 may again begin pulsating about the threshold electrical signal level 1504. The electrical signal 1502 may have a similar characteristics as the pulsating signal shown between T0 and T1. In this case, the light display on the catheter device may begin flashing, indicating the device is in the operational mode, and another sterilization cycle may be initiated after the luer device is reinserted into the luer port. In this way, the catheter device may be controlled, using the electronic control system on the catheter device, to activate the UV light source during predetermined sterilization cycles of the catheter device. By operating the catheter device during the predetermined cycles, sterilization efficiency may improve while minimizing patient infections.

In one example, a catheter access port cleaning, disinfection or sterilization device, comprising: a first housing comprising a power source and control circuit; a second housing shaped to mate with a catheter and having a first ultra-violet light source that is non-visible to a human eye mounted therein, the first housing wired to the second housing to power the light source; wherein the light source is configured to emit ultraviolet light of a predetermined wavelength of 100-280 nm that is directed to disinfect the catheter access port for a duration of 1 second to 10 minutes; further wherein a visible light indicator is mounted to the access port to indicate status of the device by flashing a visible color when the ultraviolet light is emitted from the light source. In the preceding example additionally or optionally, the first housing is substantially flat as compared to the second housing. In any or all of the preceding examples, additionally or optionally, the second housing has a screw-on fitting. In any or all of the preceding examples, additionally or optionally, the catheter device may further comprise a third housing shaped to mate with a catheter and having a second ultra-violet light source, the third housing wired to the first housing and separate and freely-movable from the second housing.

Furthermore, in any or all of the preceding examples, additionally or optionally, the first housing includes a tab for attachment to garments of a patient in which the catheter is placed. In any or all of the preceding examples, additionally or optionally, the first housing is disc-shaped. In any or all of the preceding examples, additionally or optionally, the first housing includes a plurality of ports for receiving a plurality of connectors of the wires from the second and third housings, respectively. In any or all of the preceding examples, additionally or optionally, the second housing includes a plurality of flat fins oppositely extending along an exterior surface of the second housing.

In another example, a catheter cleaning kit may comprise a plurality of housings. Any or all of the preceding examples, may additionally or optionally comprise, a first housing having a power source and control circuit, a second housing shaped to mate with a catheter and having a first ultra-violet light source mounted therein, and a cable for connecting the first housing to the second housing. In any or all of the preceding examples, additionally or optionally, the cable is permanently affixed to one of the first and second housings. Any or all of the preceding examples, may additionally or optionally comprise, a handle having a power supply and a tamper-proof luer lock keyed to mate with the handle, the tamper-proof luer lock comprising a UV-C LED luer port shaped to connect to a luer of a catheter.

Furthermore, in any or all of the preceding examples, additionally or optionally, the handle includes a visible light source, and further comprises a male luer-lock fitting at one end with a key to mate with the luer lock. In any or all of the preceding examples, additionally or optionally, the male luer-lock fitting mates with the luer lock at an opposite end from an opening having the UV-C port shaped to connect to the catheter luer. In any or all of the preceding examples, additionally or optionally, the luer lock further comprises a retractable cover, thumb closure dial, and side-entrance with a silicone grip; wherein the retractable cover is comprised of a material that prevents accidental leakage of ultraviolet radiation from the kit. In any or all of the preceding examples, additionally or optionally, the material of the retractable cover is an opaque material. In any or all of the preceding examples, additionally or optionally, the UV-C LED luer port is configured with an internal reflective surface to direct ultraviolet light to disinfect the luer port.

Note that the example systems included herein can be used with various medical catheter system configurations. The control methods and routines disclosed herein may be stored as executable instructions in non-transitory memory and may be carried out by the control system including the microcontroller in combination with the various sensors, actuators, and other catheter hardware components. The specific routines described herein may represent one or more of any number of processing strategies such as event-driven, interrupt-driven, multi-tasking, multi-threading, and the like. As such, various actions, operations, and/or functions illustrated may be performed in the sequence illustrated, in parallel, or in some cases omitted. Likewise, the order of processing is not necessarily required to achieve the features and advantages of the example examples described herein, but is provided for ease of illustration and description. One or more of the illustrated actions, operations and/or functions may be repeatedly performed depending on the particular strategy being used. Further, the described actions, operations and/or functions may graphically represent code to be programmed into non-transitory memory of the computer readable storage medium in the catheter control system, where the described actions are carried out by executing the instructions in a system including the various catheter hardware components in combination with the electronic controller.

It will be appreciated that the configurations and routines disclosed herein are exemplary in nature, and that these specific embodiments are not to be considered in a limiting sense, because numerous variations are possible. For example, the above technology can be applied to a catheter system having different components that may assembled together to form a single functional catheter unit and other catheter systems. The subject matter of the present disclosure includes all novel and non-obvious combinations and sub-combinations of the various systems and configurations, and other features, functions, and/or properties disclosed herein.

The following claims particularly point out certain combinations and sub-combinations regarded as novel and non-obvious. These claims may refer to "an" element or "a first" element or the equivalent thereof. Such claims should be understood to include incorporation of one or more such elements, neither requiring nor excluding two or more such elements. Other combinations and sub-combinations of the disclosed features, functions, elements, and/or properties may be claimed through amendment of the present claims or through presentation of new claims in this or a related application. Such claims, whether broader, narrower, equal, or different in scope to the original claims, also are regarded as included within the subject matter of the present disclosure.

The invention claimed is:

1. A system for cleaning, disinfection or sterilization of catheter access ports, comprising:
   a plurality of cleaning, disinfection or sterilization devices, wherein each cleaning, disinfection or sterilization device of the plurality of cleaning, disinfection or sterilization devices comprises:
   a first housing comprising a power source and control circuit; and
   a second housing, wherein the first housing is substantially flat on both a top surface and a bottom surface as compared to a top surface and a bottom surface of the second housing;
   wherein the second housing is shaped to mate with a catheter and having a first ultra-violet light source that is non-visible to a human eye mounted therein, the first housing wired to the second housing to power the first ultra-violet light source; wherein the first ultra-violet light source is configured to emit ultraviolet light of a predetermined wavelength of 100-280 nm that is directed to disinfect a catheter access port of the catheter for a duration of 1 second to 10 minutes; further wherein a visible light indicator is mounted to the catheter access port to indicate status of one of the plurality of cleaning, disinfection or sterilization devices that is coupled to the catheter access port by flashing a visible color when the ultraviolet light is emitted from the first ultra-violet light source; and wherein each first housing of the plurality of cleaning, disinfection or sterilization devices is shaped identically, wherein the bottom surface of the first housing of each one of the of the plurality of cleaning, disinfection or sterilization devices is shaped to snap-fit with the top surface of the first housing of each one of the of the plurality of cleaning, disinfection or sterilization devices.

2. The system of claim 1, wherein the top surface of the first housing includes one of a recess and a protrusion, and the bottom surface of the first housing includes the other of the recess and the protrusion.

3. The system of claim 2, wherein the second housing has a luer lock.

4. The system of claim 3, wherein the second housing wired to the first housing with wires and separate and freely-movable from the first housing.

5. The system of claim 4, wherein the first housing includes a tab for attachment to the body or on a garments of a patient.

6. The system of claim 4, wherein the first housing is disc-shaped.

7. The system of claim 1, wherein the second housing includes a plurality of flat fins oppositely extending along an exterior surface of the second housing.

8. A catheter cleaning kit having a plurality of housings, including a first housing having a power source and control circuit, a second housing shaped to mate with a catheter and having a first ultra-violet light source mounted therein, and a cable for connecting the first housing to the second housing; the catheter cleaning kit further comprising a handle having a separate power supply and a tamper-proof luer lock keyed to mate with the handle, the tamper-proof luer lock comprising a UV-C LED luer port shaped to connect to a luer of a catheter.

9. The catheter cleaning kit of claim 8, wherein the cable is permanently affixed to one of the first and second housings.

10. The catheter cleaning kit of claim 8, wherein the handle includes a visible indicator light source, and further comprises a male luer-lock fitting to mate with the tamper-proof luer lock.

11. The catheter cleaning kit of claim 10, wherein the male luer-lock fitting mates with the tamper-proof luer lock at an opposite end from an opening having the UV-C LED luer port shaped to connect to the luer of the catheter.

12. The catheter cleaning kit of claim 10, wherein the tamper-proof luer lock further comprises a retractable cover, thumb closure dial, and side-entrance with a silicone grip; wherein the retractable cover is comprised of a material that prevents accidental leakage of ultraviolet radiation from the catheter cleaning kit.

13. The catheter cleaning kit of claim 12, wherein the material of the retractable cover is an opaque material.

14. The catheter cleaning kit of claim 10, wherein the UV-C LED luer port is configured with an internal reflective surface to direct ultraviolet light to disinfect the UV-C LED luer port.

* * * * *